US012539212B2

(12) United States Patent
Schwarcz et al.

(10) Patent No.: US 12,539,212 B2

(45) Date of Patent: Feb. 3, 2026

(54) FLEX SENSORS FOR MEASURING REAL-TIME VALVE DIAMETER DURING PROCEDURE

(71) Applicant: Edwards Lifesciences Corporation, Irvine, CA (US)

(72) Inventors: Elazar Levi Schwarcz, Netanya (IL); Oren Cohen, Kadima (IL); Anatoly Dvorsky, Haifa (IL); Natanel Simcha Sirote, Zikhron Ya'akov (IL)

(73) Assignee: Edwards Lifesciences Corporation, Irvine, CA (US)

( * ) Notice: Subject to any disclaimer, the term of this patent is extended or adjusted under 35 U.S.C. 154(b) by 777 days.

(21) Appl. No.: 17/826,751

(22) Filed: May 27, 2022

(65) Prior Publication Data

US 2022/0280298 A1 Sep. 8, 2022

Related U.S. Application Data

(63) Continuation of application No. PCT/US2020/062989, filed on Dec. 3, 2020.

(Continued)

(51) Int. Cl.

*A61F 2/24* (2006.01)

*A61F 2/95* (2013.01)

(52) U.S. Cl.

CPC .......... *A61F 2/2496* (2013.01); *A61F 2/2418* (2013.01); *A61F 2/2433* (2013.01);

(Continued)

(58) Field of Classification Search

CPC ........ A61F 2/24; A61F 2/2418; A61F 2/2409; A61F 2/2496; A61F 2/06; A61F 2/86;

(Continued)

(56) References Cited

U.S. PATENT DOCUMENTS 3,409,013 A 11/1968 Berry 3,548,417 A 12/1970 Kisher (Continued)

FOREIGN PATENT DOCUMENTS

CN 106618803 A 5/2017

DE 0144167 C 9/1903

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(Continued)

*Primary Examiner* — Seema Mathew

(74) *Attorney, Agent, or Firm* — Webb & Co.

(57) ABSTRACT

A delivery assembly constituted of: a prosthetic valve comprising a plurality of intersecting struts, and a delivery apparatus comprising: a handle; a delivery shaft extending distally from the handle; and a flex sensing assembly, comprising: at least one flex sensor coupled to at least one of the plurality of struts; and a control unit in communication with the at least one flex sensor, wherein the prosthetic valve is movable between a radially compressed configuration and a radially expanded configuration, and wherein, responsive to an output of the at least one flex sensor, the control unit is configured to generate a signal indicative of a diameter of the prosthetic valve.

20 Claims, 30 Drawing Sheets

Related U.S. Application Data

(60) Provisional application No. 62/945,010, filed on Dec. 6, 2019.

(52) U.S. Cl.
CPC ....... *A61F 2/9517* (2020.05); *A61F 2250/001* (2013.01); *A61F 2250/0096* (2013.01)

(58) Field of Classification Search
CPC ...... A61F 2/07; A61F 2/82; A61F 2250/0096; A61B 5/6862; A61B 5/6886
See application file for complete search history.

(56) References Cited

U.S. PATENT DOCUMENTS

| | | | |
|---|---|---|---|
| 3,587,115 | A | 6/1971 | Shiley |
| 3,657,744 | A | 4/1972 | Ersek |
| 3,671,979 | A | 6/1972 | Moulopoulos |
| 3,714,671 | A | 2/1973 | Edwards et al. |
| 3,755,823 | A | 9/1973 | Hancock |
| 4,035,849 | A | 7/1977 | Angell et al. |
| 4,056,854 | A | 11/1977 | Boretos et al. |
| 4,106,129 | A | 8/1978 | Carpentier et al. |
| 4,222,126 | A | 9/1980 | Boretos et al. |
| 4,265,694 | A | 5/1981 | Boretos et al. |
| 4,297,749 | A | 11/1981 | Davis et al. |
| 4,339,831 | A | 7/1982 | Johnson |
| 4,343,048 | A | 8/1982 | Ross et al. |
| 4,345,340 | A | 8/1982 | Rosen |
| 4,373,216 | A | 2/1983 | Klawitter |
| 4,406,022 | A | 9/1983 | Roy |
| 4,441,216 | A | 4/1984 | Ionescu et al. |
| 4,470,157 | A | 9/1984 | Love |
| 4,535,483 | A | 8/1985 | Klawitter et al. |
| 4,574,803 | A | 3/1986 | Storz |
| 4,592,340 | A | 6/1986 | Boyles |
| 4,605,407 | A | 8/1986 | Black et al. |
| 4,612,011 | A | 9/1986 | Kautzky |
| 4,643,732 | A | 2/1987 | Pietsch et al. |
| 4,655,771 | A | 4/1987 | Wallsten |
| 4,692,164 | A | 9/1987 | Dzemeshkevich et al. |
| 4,733,665 | A | 3/1988 | Palmaz |
| 4,759,758 | A | 7/1988 | Gabbay |
| 4,762,128 | A | 8/1988 | Rosenbluth |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,820,299 | A | 4/1989 | Philippe et al. |
| 4,829,990 | A | 5/1989 | Thuroff et al. |
| 4,851,001 | A | 7/1989 | Taheri |
| 4,856,516 | A | 8/1989 | Hillstead |
| 4,878,495 | A | 11/1989 | Grayzel |
| 4,878,906 | A | 11/1989 | Lindemann et al. |
| 4,883,458 | A | 11/1989 | Shiber |
| 4,922,905 | A | 5/1990 | Strecker |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,080,668 | A | 1/1992 | Bolz et al. |
| 5,085,635 | A | 2/1992 | Cragg |
| 5,089,015 | A | 2/1992 | Ross |
| 5,152,771 | A | 10/1992 | Sabbaghian et al. |
| 5,163,953 | A | 11/1992 | Vince |
| 5,167,628 | A | 12/1992 | Boyles |
| 5,192,297 | A | 3/1993 | Hull |
| 5,266,073 | A | 11/1993 | Wall |
| 5,282,847 | A | 2/1994 | Trescony et al. |
| 5,295,958 | A | 3/1994 | Shturman |
| 5,332,402 | A | 7/1994 | Teitelbaum |
| 5,360,444 | A | 11/1994 | Kusuhara |
| 5,370,685 | A | 12/1994 | Stevens |
| 5,397,351 | A | 3/1995 | Pavcnik et al. |
| 5,411,055 | A | 5/1995 | Kane |
| 5,411,552 | A | 5/1995 | Andersen et al. |
| 5,443,446 | A | 8/1995 | Shturman |
| 5,480,424 | A | 1/1996 | Cox |
| 5,500,014 | A | 3/1996 | Quijano et al. |
| 5,545,209 | A | 8/1996 | Roberts et al. |
| 5,545,214 | A | 8/1996 | Stevens |
| 5,549,665 | A | 8/1996 | Vesely et al. |
| 5,554,185 | A | 9/1996 | Block et al. |
| 5,558,644 | A | 9/1996 | Boyd et al. |
| 5,571,175 | A | 11/1996 | Vanney et al. |
| 5,584,803 | A | 12/1996 | Stevens et al. |
| 5,591,185 | A | 1/1997 | Kilmer et al. |
| 5,591,195 | A | 1/1997 | Taheri et al. |
| 5,607,464 | A | 3/1997 | Trescony et al. |
| 5,609,626 | A | 3/1997 | Quijano et al. |
| 5,628,792 | A | 5/1997 | Lentell |
| 5,639,274 | A | 6/1997 | Fischell et al. |
| 5,665,115 | A | 9/1997 | Cragg |
| 5,716,417 | A | 2/1998 | Girard et al. |
| 5,728,068 | A | 3/1998 | Leone et al. |
| 5,749,890 | A | 5/1998 | Shaknovich |
| 5,756,476 | A | 5/1998 | Epstein et al. |
| 5,769,812 | A | 6/1998 | Stevens et al. |
| 5,800,508 | A | 9/1998 | Goicoechea et al. |
| 5,840,081 | A | 11/1998 | Andersen et al. |
| 5,855,597 | A | 1/1999 | Jayaraman |
| 5,855,601 | A | 1/1999 | Bessler et al. |
| 5,855,602 | A | 1/1999 | Angell |
| 5,925,063 | A | 7/1999 | Khosravi |
| 5,957,949 | A | 9/1999 | Leonhardt et al. |
| 6,027,525 | A | 2/2000 | Suh et al. |
| 6,132,473 | A | 10/2000 | Williams et al. |
| 6,168,614 | B1 | 1/2001 | Andersen et al. |
| 6,171,335 | B1 | 1/2001 | Wheatley et al. |
| 6,174,327 | B1 | 1/2001 | Mertens et al. |
| 6,210,408 | B1 | 4/2001 | Chandrasekaran et al. |
| 6,217,585 | B1 | 4/2001 | Houser et al. |
| 6,221,091 | B1 | 4/2001 | Khosravi |
| 6,231,602 | B1 | 5/2001 | Carpentier et al. |
| 6,245,102 | B1 | 6/2001 | Jayaraman |
| 6,299,637 | B1 | 10/2001 | Shaolian et al. |
| 6,302,906 | B1 | 10/2001 | Goecoechea et al. |
| 6,350,277 | B1 | 2/2002 | Kocur |
| 6,352,547 | B1 | 3/2002 | Brown et al. |
| 6,425,916 | B1 | 7/2002 | Garrison et al. |
| 6,440,764 | B1 | 8/2002 | Focht et al. |
| 6,454,799 | B1 | 9/2002 | Schreck |
| 6,458,153 | B1 | 10/2002 | Bailey et al. |
| 6,461,382 | B1 | 10/2002 | Cao |
| 6,468,660 | B2 | 10/2002 | Ogle et al. |
| 6,482,228 | B1 | 11/2002 | Norred |
| 6,488,704 | B1 | 12/2002 | Connelly et al. |
| 6,527,979 | B2 | 3/2003 | Constantz |
| 6,569,196 | B1 | 5/2003 | Vesely |
| 6,582,462 | B1 | 6/2003 | Andersen et al. |
| 6,605,112 | B1 | 8/2003 | Moll et al. |
| 6,652,578 | B2 | 11/2003 | Bailey et al. |
| 6,689,123 | B2 | 2/2004 | Pinchasik |
| 6,716,244 | B2 | 4/2004 | Klaco |
| 6,730,118 | B2 | 5/2004 | Spenser et al. |
| 6,733,525 | B2 | 5/2004 | Yang et al. |
| 6,767,362 | B2 | 7/2004 | Schreck |
| 6,769,161 | B2 | 8/2004 | Brown et al. |
| 6,783,542 | B2 | 8/2004 | Eidenschink |
| 6,830,584 | B1 | 12/2004 | Seguin |
| 6,878,162 | B2 | 4/2005 | Bales et al. |
| 6,893,460 | B2 | 5/2005 | Spenser et al. |
| 6,908,481 | B2 | 6/2005 | Cribier |
| 6,936,067 | B2 | 8/2005 | Buchanan |
| 7,018,406 | B2 | 3/2006 | Seguin et al. |
| 7,018,408 | B2 | 3/2006 | Bailey et al. |
| 7,096,554 | B2 | 8/2006 | Austin et al. |

(56) References Cited

U.S. PATENT DOCUMENTS

| | | | | |
|---|---|---|---|---|
| 7,181,261 | B2 * | 2/2007 | Silver | A61B 5/6876 204/403.01 |
| 7,225,518 | B2 | 6/2007 | Eidenschink et al. | |
| 7,276,078 | B2 | 10/2007 | Spenser et al. | |
| 7,276,084 | B2 | 10/2007 | Yang et al. | |
| 7,318,278 | B2 | 1/2008 | Zhang et al. | |
| 7,374,571 | B2 | 5/2008 | Pease et al. | |
| 7,393,360 | B2 | 7/2008 | Spenser et al. | |
| 7,462,191 | B2 | 12/2008 | Spenser et al. | |
| 7,510,575 | B2 | 3/2009 | Spenser et al. | |
| 7,563,280 | B2 | 7/2009 | Anderson et al. | |
| 7,585,321 | B2 | 9/2009 | Cribier | |
| 7,618,446 | B2 | 11/2009 | Andersen et al. | |
| 7,618,447 | B2 | 11/2009 | Case et al. | |
| 7,655,034 | B2 | 2/2010 | Mitchell et al. | |
| 7,769,420 | B2 * | 8/2010 | Silver | A61B 5/6882 600/300 |
| 7,785,366 | B2 | 8/2010 | Maurer et al. | |
| 7,959,672 | B2 | 6/2011 | Salahieh et al. | |
| 7,993,394 | B2 | 8/2011 | Hariton et al. | |
| 8,029,556 | B2 | 10/2011 | Rowe | |
| 8,167,932 | B2 | 5/2012 | Bourang | |
| 8,291,570 | B2 | 10/2012 | Eidenschink et al. | |
| 8,449,606 | B2 | 5/2013 | Eliasen et al. | |
| 8,454,685 | B2 | 6/2013 | Hariton et al. | |
| 8,652,203 | B2 | 2/2014 | Quadri et al. | |
| 8,747,463 | B2 | 6/2014 | Fogarty et al. | |
| 9,078,781 | B2 | 7/2015 | Ryan et al. | |
| 11,006,845 | B2 * | 5/2021 | Kuraguntla | A61F 2/06 |
| 11,224,509 | B2 | 1/2022 | Dasi et al. | |
| 2001/0021872 | A1 | 9/2001 | Bailey et al. | |
| 2002/0026094 | A1 | 2/2002 | Roth | |
| 2002/0032481 | A1 | 3/2002 | Gabbay | |
| 2002/0138135 | A1 | 9/2002 | Duerig et al. | |
| 2002/0173842 | A1 | 11/2002 | Buchanan | |
| 2003/0050694 | A1 | 3/2003 | Yang et al. | |
| 2003/0100939 | A1 | 5/2003 | Yodfat et al. | |
| 2003/0158597 | A1 | 8/2003 | Quiachon et al. | |
| 2003/0212454 | A1 | 11/2003 | Scott et al. | |
| 2004/0039436 | A1 | 2/2004 | Spenser et al. | |
| 2004/0186563 | A1 | 9/2004 | Lobbi | |
| 2004/0186565 | A1 | 9/2004 | Schreck | |
| 2004/0260389 | A1 | 12/2004 | Case et al. | |
| 2005/0010285 | A1 | 1/2005 | Lambrecht et al. | |
| 2005/0075725 | A1 | 4/2005 | Rowe | |
| 2005/0075728 | A1 | 4/2005 | Nguyen et al. | |
| 2005/0096736 | A1 | 5/2005 | Osse et al. | |
| 2005/0188525 | A1 | 9/2005 | Weber et al. | |
| 2005/0203614 | A1 | 9/2005 | Forster et al. | |
| 2005/0203617 | A1 | 9/2005 | Forster et al. | |
| 2005/0234546 | A1 | 10/2005 | Nugent et al. | |
| 2006/0004469 | A1 | 1/2006 | Sokel | |
| 2006/0025857 | A1 | 2/2006 | Bergheim et al. | |
| 2006/0058872 | A1 | 3/2006 | Salahieh et al. | |
| 2006/0074484 | A1 | 4/2006 | Huber | |
| 2006/0149350 | A1 | 7/2006 | Patel et al. | |
| 2006/0183383 | A1 | 8/2006 | Asmus et al. | |
| 2006/0229719 | A1 | 10/2006 | Marquez et al. | |
| 2006/0259137 | A1 | 11/2006 | Artof et al. | |
| 2006/0287717 | A1 | 12/2006 | Rowe et al. | |
| 2007/0005131 | A1 | 1/2007 | Taylor | |
| 2007/0010876 | A1 | 1/2007 | Salahieh et al. | |
| 2007/0010877 | A1 | 1/2007 | Salahieh et al. | |
| 2007/0112422 | A1 | 5/2007 | Dehdashtian | |
| 2007/0162102 | A1 | 7/2007 | Ryan et al. | |
| 2007/0203503 | A1 | 8/2007 | Salahieh et al. | |
| 2007/0203575 | A1 | 8/2007 | Forster et al. | |
| 2007/0203576 | A1 | 8/2007 | Lee et al. | |
| 2007/0213813 | A1 | 9/2007 | Von Segesser et al. | |
| 2007/0233228 | A1 | 10/2007 | Eberhardt et al. | |
| 2007/0260305 | A1 | 11/2007 | Drews et al. | |
| 2007/0265700 | A1 | 11/2007 | Eliasen et al. | |
| 2008/0114442 | A1 | 5/2008 | Mitchell et al. | |
| 2008/0125853 | A1 | 5/2008 | Bailey et al. | |
| 2008/0154355 | A1 | 6/2008 | Benichou et al. | |
| 2008/0183271 | A1 | 7/2008 | Frawley et al. | |
| 2008/0243245 | A1 | 10/2008 | Thambar et al. | |
| 2008/0275537 | A1 | 11/2008 | Limon | |
| 2009/0125118 | A1 | 5/2009 | Gong | |
| 2009/0157175 | A1 | 6/2009 | Benichou | |
| 2009/0270742 | A1 * | 10/2009 | Wolinsky | A61B 5/6882 600/486 |
| 2009/0276040 | A1 | 11/2009 | Rowe et al. | |
| 2009/0281619 | A1 | 11/2009 | Le et al. | |
| 2009/0299452 | A1 | 12/2009 | Eidenschink et al. | |
| 2009/0319037 | A1 | 12/2009 | Rowe et al. | |
| 2010/0049313 | A1 | 2/2010 | Alon et al. | |
| 2010/0168844 | A1 | 7/2010 | Toomes et al. | |
| 2010/0198347 | A1 | 8/2010 | Zakay et al. | |
| 2010/0204781 | A1 | 8/2010 | Alkhatib | |
| 2011/0015729 | A1 | 1/2011 | Jimenez et al. | |
| 2011/0066224 | A1 | 3/2011 | White | |
| 2011/0137397 | A1 | 6/2011 | Chau et al. | |
| 2011/0218619 | A1 | 9/2011 | Benichou et al. | |
| 2011/0264194 | A1 * | 10/2011 | Griswold | A61B 5/6862 600/300 |
| 2011/0319991 | A1 | 12/2011 | Hariton et al. | |
| 2012/0089223 | A1 | 4/2012 | Nguyen et al. | |
| 2012/0101571 | A1 | 4/2012 | Thambar et al. | |
| 2012/0123529 | A1 | 5/2012 | Levi et al. | |
| 2012/0259409 | A1 | 10/2012 | Nguyen et al. | |
| 2012/0323300 | A1 * | 12/2012 | Greenberg | A61F 2/95 623/1.11 |
| 2013/0023985 | A1 | 1/2013 | Khairkhahan et al. | |
| 2013/0046373 | A1 | 2/2013 | Cartledge et al. | |
| 2013/0150956 | A1 | 6/2013 | Yohanan et al. | |
| 2013/0166017 | A1 | 6/2013 | Cartledge et al. | |
| 2013/0190857 | A1 | 7/2013 | Mitra et al. | |
| 2013/0274873 | A1 | 10/2013 | Delaloye et al. | |
| 2013/0310926 | A1 | 11/2013 | Hariton | |
| 2013/0317598 | A1 | 11/2013 | Rowe et al. | |
| 2013/0331929 | A1 | 12/2013 | Mitra et al. | |
| 2014/0107768 | A1 | 4/2014 | Venkatasubramanian | |
| 2014/0194981 | A1 | 7/2014 | Menk et al. | |
| 2014/0200661 | A1 | 7/2014 | Pintor et al. | |
| 2014/0209238 | A1 | 7/2014 | Bonyuet et al. | |
| 2014/0222136 | A1 | 8/2014 | Geist et al. | |
| 2014/0277417 | A1 | 9/2014 | Schraut et al. | |
| 2014/0277419 | A1 | 9/2014 | Garde et al. | |
| 2014/0277424 | A1 | 9/2014 | Oslund | |
| 2014/0277563 | A1 | 9/2014 | White | |
| 2014/0330372 | A1 | 11/2014 | Weston et al. | |
| 2014/0343671 | A1 | 11/2014 | Yohanan et al. | |
| 2014/0350667 | A1 | 11/2014 | Braido et al. | |
| 2015/0073545 | A1 | 3/2015 | Braido | |
| 2015/0073546 | A1 | 3/2015 | Braido | |
| 2015/0335290 | A1 * | 11/2015 | Hunter | A61B 5/076 623/1.13 |
| 2016/0022447 | A1 * | 1/2016 | Kim | A61B 5/02158 623/1.15 |
| 2016/0045316 | A1 * | 2/2016 | Braido | A61F 2/2445 623/2.38 |
| 2016/0256107 | A1 * | 9/2016 | Gupta | A61B 5/026 |
| 2016/0262700 | A1 * | 9/2016 | Kuraguntla | A61B 5/6876 |
| 2017/0196509 | A1 * | 7/2017 | Hunter | A61F 2/2472 |
| 2017/0231573 | A1 * | 8/2017 | Reiner | A61B 5/6861 |
| 2018/0064565 | A1 * | 3/2018 | MacTaggart | A61B 17/12045 |
| 2018/0078183 | A1 * | 3/2018 | Lor | G06F 3/011 |
| 2018/0153689 | A1 | 6/2018 | Maimon et al. | |
| 2020/0289149 | A1 * | 9/2020 | Cohn | A61B 17/32075 |
| 2021/0244534 | A1 * | 8/2021 | Cohen | A61F 2/243 |
| 2022/0240800 | A1 * | 8/2022 | Sweeney | A61B 5/02007 |
| 2023/0218180 | A1 * | 7/2023 | Mujeeb-U-Rahman | A61B 5/4851 623/2.17 |
| 2023/0355380 | A1 * | 11/2023 | Argento | A61F 2/915 |
| 2024/0023896 | A1 * | 1/2024 | Enomoto | A61B 5/6862 |
| 2024/0058129 | A1 * | 2/2024 | Fetherston | A61B 5/1077 |
| 2024/0197255 | A1 * | 6/2024 | Botzer | A61B 34/20 |

(56) References Cited

U.S. PATENT DOCUMENTS

| | | | | |
|---|---|---|---|---|
| 2024/0358506 | A1* | 10/2024 | Leichner | A61F 2/2436 |
| 2025/0018176 | A1* | 1/2025 | Chang | A61B 5/24 |

FOREIGN PATENT DOCUMENTS

| | | | | | |
|---|---|---|---|---|---|
| DE | 2246526 | A1 | | 3/1973 | |
| DE | 19532846 | A1 | | 3/1997 | |
| DE | 19546692 | A1 | | 6/1997 | |
| DE | 19857887 | A1 | | 7/2000 | |
| DE | 19907646 | A1 | | 8/2000 | |
| DE | 10049812 | A1 | | 4/2002 | |
| DE | 10049813 | C1 | | 4/2002 | |
| DE | 10049814 | A1 | | 4/2002 | |
| DE | 10049815 | A1 | | 4/2002 | |
| EP | 0103546 | A1 | | 3/1984 | |
| EP | 0850607 | A1 | | 7/1998 | |
| EP | 1057460 | A1 | | 12/2000 | |
| EP | 1088529 | A2 | | 4/2001 | |
| EP | 1570809 | A1 | | 9/2005 | |
| EP | 4062871 | A1 | * | 9/2022 | A61F 2/95 |
| FR | 2788217 | A1 | | 7/2000 | |
| FR | 2815844 | A1 | | 5/2002 | |
| GB | 2056023 | A | | 3/1981 | |
| JP | 2021525561 | A | * | 9/2021 | A61B 5/6882 |
| SU | 1271508 | A1 | | 11/1986 | |
| WO | 9117720 | A1 | | 11/1991 | |
| WO | 9217118 | A1 | | 10/1992 | |
| WO | 9301768 | A1 | | 2/1993 | |
| WO | 9724080 | A1 | | 7/1997 | |
| WO | 9829057 | A1 | | 7/1998 | |
| WO | 9930646 | A1 | | 6/1999 | |
| WO | 9933414 | A1 | | 7/1999 | |
| WO | 9940964 | A1 | | 8/1999 | |
| WO | 9947075 | A1 | | 9/1999 | |
| WO | 0018333 | A1 | | 4/2000 | |
| WO | 0041652 | A1 | | 7/2000 | |
| WO | 0047139 | A1 | | 8/2000 | |
| WO | 0135878 | A2 | | 5/2001 | |
| WO | 0149213 | A2 | | 7/2001 | |
| WO | 0154624 | A1 | | 8/2001 | |
| WO | 0154625 | A1 | | 8/2001 | |
| WO | 0162189 | A1 | | 8/2001 | |
| WO | 0164137 | A1 | | 9/2001 | |
| WO | 0176510 | A2 | | 10/2001 | |
| WO | 0222054 | A1 | | 3/2002 | |
| WO | 0236048 | A1 | | 5/2002 | |
| WO | 0241789 | A2 | | 5/2002 | |
| WO | 0243620 | A1 | | 6/2002 | |
| WO | 0247575 | A2 | | 6/2002 | |
| WO | 0249540 | A2 | | 6/2002 | |
| WO | 03047468 | A1 | | 6/2003 | |
| WO | 2005034812 | A1 | | 4/2005 | |
| WO | 2005055883 | A1 | | 6/2005 | |
| WO | 2005084595 | A1 | | 9/2005 | |
| WO | 2005102015 | A2 | | 11/2005 | |
| WO | 2006014233 | A2 | | 2/2006 | |
| WO | 2006032051 | A2 | | 3/2006 | |
| WO | 2006034008 | A2 | | 3/2006 | |
| WO | 2006111391 | A1 | | 10/2006 | |
| WO | 2006127089 | A1 | | 11/2006 | |
| WO | 2006138173 | A2 | | 12/2006 | |
| WO | 2007047488 | A2 | | 4/2007 | |
| WO | 2007067942 | A1 | | 6/2007 | |
| WO | 2007097983 | A2 | | 8/2007 | |
| WO | 2008005405 | A2 | | 1/2008 | |
| WO | 2008015257 | A2 | | 2/2008 | |
| WO | 2008035337 | A2 | | 3/2008 | |
| WO | 2008091515 | A2 | | 7/2008 | |
| WO | 2008147964 | A1 | | 12/2008 | |
| WO | 2008150529 | A1 | | 12/2008 | |
| WO | 2009033469 | A1 | | 3/2009 | |
| WO | 2009042196 | A2 | | 4/2009 | |
| WO | 2009053497 | A1 | | 4/2009 | |
| WO | 2009061389 | A2 | | 5/2009 | |
| WO | 2009094188 | A2 | | 7/2009 | |
| WO | 2009116041 | A2 | | 9/2009 | |
| WO | 2009149462 | A2 | | 12/2009 | |
| WO | 2010011699 | A2 | | 1/2010 | |
| WO | 2010121076 | A2 | | 10/2010 | |
| WO | 2013106585 | A1 | | 7/2013 | |
| WO | WO-2014186646 | A1 | | 11/2014 | |
| WO | 2015085218 | A1 | | 6/2015 | |
| WO | WO-2020092251 | A1 | * | 5/2020 | A61F 2/9517 |
| WO | WO-2021086836 | A1 | * | 5/2021 | A61F 2/2418 |
| WO | WO-2022046834 | A1 | * | 3/2022 | A61B 5/1076 |
| WO | WO-2022066713 | A1 | * | 3/2022 | A61B 5/6862 |
| WO | WO-2023137024 | A1 | * | 7/2023 | A61F 2/2436 |
| WO | WO-2023167851 | A1 | * | 9/2023 | A61F 2/2433 |
| WO | WO-2023205087 | A1 | * | 10/2023 | A61F 2/06 |
| WO | WO-2024129880 | A1 | * | 6/2024 | A61F 2/06 |
| WO | WO-2024130135 | A1 | * | 6/2024 | A61B 5/686 |
| WO | WO-2024163313 | A1 | * | 8/2024 | A61F 2/2427 |
| WO | WO-2024163373 | A1 | * | 8/2024 | A61F 2/2418 |
| WO | WO-2025075966 | A1 | * | 4/2025 | A61B 8/12 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

* cited by examiner

FIG. 3A
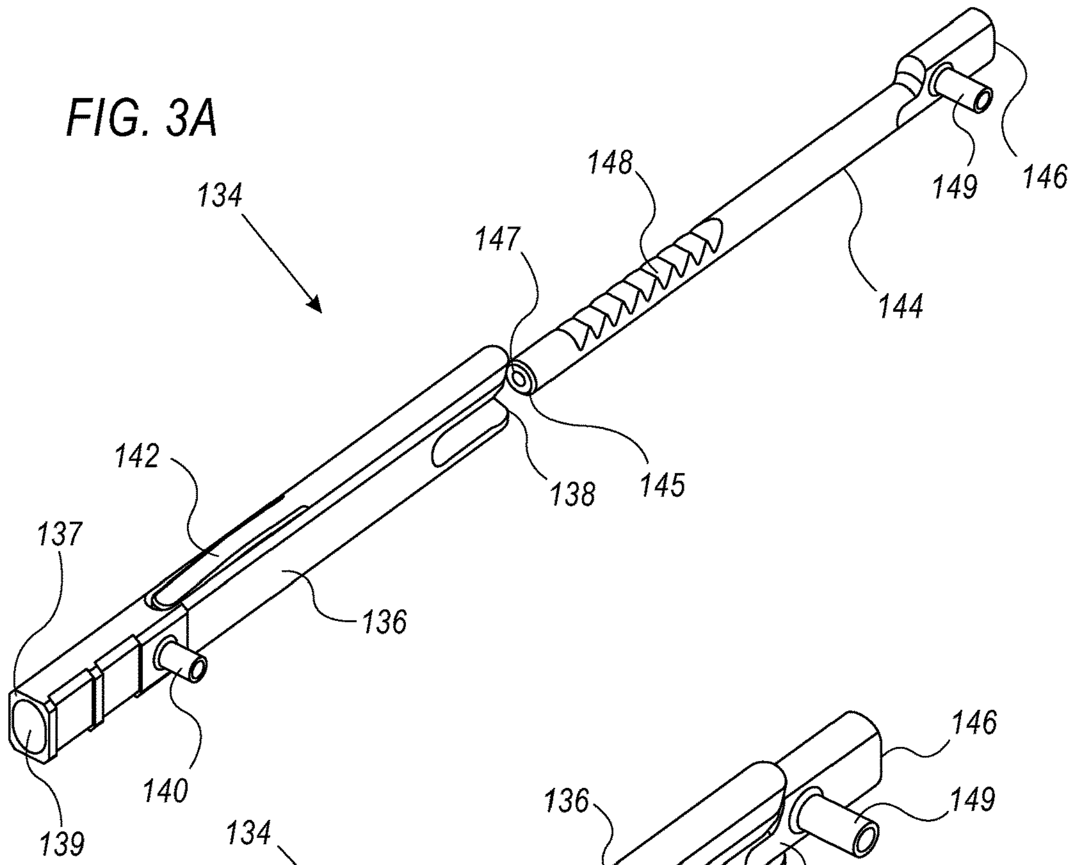
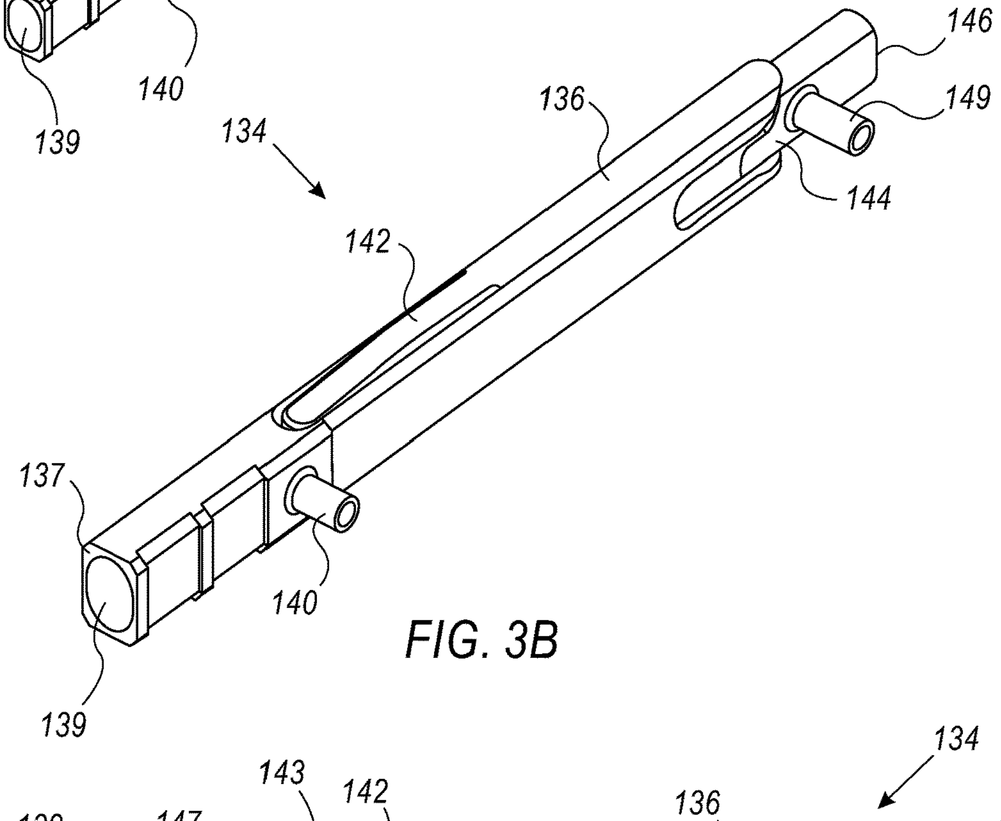
FIG. 3B
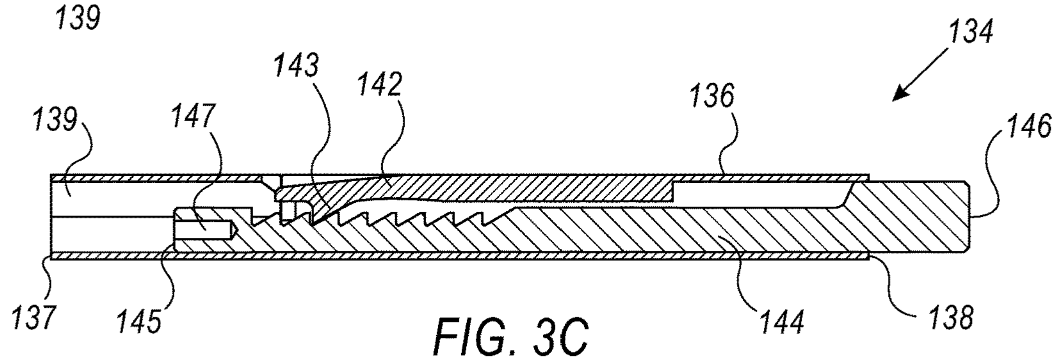
FIG. 3C

FLEX SENSORS FOR MEASURING REAL-TIME VALVE DIAMETER DURING PROCEDURE

CROSS REFERENCE TO RELATED APPLICATIONS

This application is a continuation of a PCT Patent Application No. PCT/US2020/062989, entitled "FLEX SENSORS FOR MEASURING REAL-TIME VALVE DIAMETER DURING PROCEDURE," filed Dec. 3, 2020, which claims the benefit of U.S. Provisional Application No. 62/945,010, entitled "FLEX SENSORS FOR MEASURING REAL-TIME VALVE DIAMETER DURING PROCEDURE," filed Dec. 6, 2019, all of which are incorporated by reference herein in their entirety.

FIELD

The present invention relates to devices and methods for measuring prosthetic valve expansion diameter, and in particular, for devices equipped with at least one flex sensor configured to provide real-time estimate of prosthetic valve expansion diameter.

BACKGROUND

Native heart valves, such as the aortic, pulmonary and mitral valves, function to assure adequate directional flow from and to the heart, and between the heart's chambers, to supply blood to the whole cardiovascular system. Various valvular diseases can render the valves ineffective and require replacement with artificial valves. Surgical procedures can be performed to repair or replace a heart valve. Surgeries are prone to an abundance of clinical complications, hence alternative less invasive techniques of delivering a prosthetic heart valve over a catheter and implanting it over the native malfunctioning valve, have been developed over the years.

Mechanically expandable valves are a category of prosthetic valves that rely on a mechanical actuation mechanism for expansion. The actuation mechanism usually includes a plurality of actuation/locking assemblies, releasably connected to respective actuation members of the valve delivery system, controlled via the handle for actuating the assemblies to expand the valve to a desired diameter. The assemblies may optionally lock the valve's position to prevent undesired recompression thereof, and disconnection of the delivery system's actuation member from the valve actuation/locking assemblies, to enable retrieval thereof once the valve is properly positioned at the desired site of implantation.

When implanting a prosthetic valve, such as a mechanically expandable valve, it is desirable to expand the valve to a maximum size allowed by the patient's anatomical considerations, in order to avoid paravalvular leakage or other unfavorable hemodynamic phenomena across the valve that may be associated with a mismatch between the valve's expansion diameter and the surrounding tissue, while mitigating the risk of annular rupture that may result from over-expansion. To ensure optimal implantation size, the diameter of the prosthetic valve should be monitored in real-time during the implantation procedure.

SUMMARY

The present disclosure is directed toward devices, assemblies and methods for monitoring radial expansion of a prosthetic valve during prosthetic valve implantation procedures. Real-time measurement of the expansion diameter ensures proper implantation of the prosthetic valve within a designated site of implantation, such as the site of malfunctioning native valve.

According to one aspect of the invention, a delivery assembly is provided the delivery assembly comprising: a prosthetic valve comprising a plurality of intersecting struts, and a delivery apparatus comprising: a handle; a delivery shaft extending distally from the handle; and a flex sensing assembly, comprising: at least one flex sensor coupled to at least one of the plurality of struts; and a control unit in communication with the at least one flex sensor, wherein the prosthetic valve is movable between a radially compressed configuration and a radially expanded configuration, and wherein, responsive to an output of the at least one flex sensor, the control unit is configured to generate a signal indicative of a diameter of the prosthetic valve.

According to some embodiment, the at least one flex sensor comprises a non-bending portion and a bending portion configured to flex relative to the non-bending portion.

According to some embodiments, the prosthetic valve further comprises at least one actuator assembly, wherein the delivery apparatus further comprises an actuation member releasably coupled to the at least one actuator assembly, and wherein the prosthetic valve is expandable from the radially compressed state to the radially expanded state upon actuating the at least one actuator assembly by the at least one actuation member.

According to some embodiments, the prosthetic valve further comprises at least one actuator assembly, wherein the delivery apparatus further comprises an actuation member releasably coupled to the at least one actuator assembly, wherein the prosthetic valve is expandable from the radially compressed state to the radially expanded state upon actuating the at least one actuator assembly by the at least one actuation member, and wherein the non-bending portion of the at least one flex sensor is coupled to the at least one actuator assembly.

According to some embodiments, the delivery assembly further comprises at least one communication channel, a first end of the at least one communication channel coupled to the at least one flex sensor and a second end of the at least one communication channel extending towards the handle, wherein the at least one communication channel is retractable from the prosthetic valve.

According to some embodiments, the flex sensing assembly further comprises a sensor shaft extending distally from the handle, and wherein at least a portion of the at least one communication channel extends through the sensor shaft.

According to some embodiments, the delivery assembly further comprises: at least one sensor housing attached to a strut; and at least one detachable shaft extending distally from the handle, and detachably coupled to the sensor housing, wherein the at least one flex sensor is locally attached to the at least one sensor housing; wherein at least a portion of the at least one communication channel extends through the at least one detachable shaft; wherein the communication channel is detachably coupled to the at least one flex sensor; wherein the detachable shaft is configured isolate the at least one communication channel from ambient flow, when the detachable shaft is coupled to the sensor housing; and wherein the at least one communication channel is axially movable relative to the at least one detachable shaft, when the at least one communication channel is detached from the at least one sensor.

According to some embodiments, the at least one communication channel is detachable from the at least one flex sensor upon application of a pull force on the at least one communication channel, and wherein the magnitude of the pull force is higher than a predetermined threshold magnitude.

According to some embodiments, the sensor housing comprises a sensor housing proximal threaded end, and wherein the detachable shaft comprises a detachable shaft distal threaded end, configured to engage with the sensor housing proximal threaded end.

According to some embodiments, the at least one flex sensor is an optic flex sensor configured to generate an optic signal, the at least one communication channel being at least one optic conductor, and wherein the at least one optic conductor is detachably optically coupled to the at least one optic flex sensor.

According to some embodiments, the at least one flex sensor is coupled to the strut via at least one coupling member. According to some embodiments, the at least one coupling member comprises at least one of: a suture, a band, a tube, and/or a sleeve, and wherein the at least one flex sensor is slidable relative to the at least one coupling member upon application of a force exceeding the frictional force applied by the at least one coupling member on the at least one flex sensor.

According to some embodiments, the strut to which the at least one flex sensor is coupled, comprises at least two strut apertures through which the at least one flex sensor extends.

According to some embodiments, the at least one flex sensor comprises a variable resistance element, configured to vary its electrical resistivity in response to the extent of bending applied thereto.

According to some embodiments, the variable resistance element comprises a strain gauge.

According to some embodiments, the variable resistance element comprises a conductive material layer.

According to some embodiments, the at least one flex sensor is an optic flex sensor configured to generate an optic signal.

According to some embodiments, the at least one optic flex sensor comprises a plurality of axially spaced Fiber Bragg Gratings.

According to some embodiments, the delivery assembly further comprises at least one optic conductor detachably optically coupled to the at least one optic flex sensor.

According to some embodiments, the flex sensing assembly further comprises at least one flexible distal extension, attached to and extending distally from the at least one flex sensor.

According to some embodiments, the at least one flexible distal extension is resiliently curved sideways.

According to some embodiments, the at least one flexible distal extension comprises: a first flexible distal extension comprising a first distal loop, wherein the first flexible distal extension is attached to and extends distally from the first flex sensor; and a second flexible distal extension comprising a second distal loop, wherein the second flexible distal extension is attached to and extends distally from the second flex sensor, wherein the flex sensing assembly further comprises a flexible elongate member extending distally from the handle and through the first distal loop and the second distal loop, and wherein the flexible elongate member is configured to couple the first flexible distal extension with the second flexible distal extension when extending through the first distal loop and the second distal loop, and to allow separation thereof upon being pulled therefrom.

According to some embodiments, at least one of the at least one flex sensors is coupled to at least two intersecting struts.

According to some embodiments, the at least one flex sensor comprises a first flex sensor coupled to a first strut, and a second flex sensor coupled to the second strut, wherein the at least one communication channel comprises a first communication channel coupled to the first flex sensor, and a second communication channel coupled to the second flex sensor, and wherein the first strut and the second strut are intersecting with each other.

According to some embodiments, the delivery assembly further comprises: an inflatable balloon, the inflatable balloon positioned within the prosthetic valve; a reservoir containing a predetermined volume of inflation fluid; a pump in fluid communication with the reservoir; and a fluid flow channel, a distal end of the fluid flow channel in fluid communication with an opening of the inflatable balloon and a proximal end of the fluid flow channel in fluid communication with the pump, wherein, movement of the prosthetic valve between the radially compressed configured to the radially expanded configuration is responsive to an inflation of the inflatable balloon, and wherein the pump is configured to generate flow of the inflation fluid into the inflatable balloon via the fluid flow channel.

According to some embodiments, the delivery assembly further comprises a pressure sensor configured to measure pressure of the inflation fluid, wherein, responsive to the measured pressure of the inflation fluid, the pump is further configured to adjust the generated flow of the inflation fluid.

According to some embodiments, the pressure sensor is positioned within the inflation fluid.

According to another aspect of the invention, a delivery assembly is provided, the delivery assembly comprising: a prosthetic valve comprising a plurality of intersecting struts, and a delivery apparatus comprising: a handle; a delivery shaft extending distally from the handle; and a flex sensing assembly, comprising at least one flex sensor coupled to at least one of the plurality of struts, wherein the prosthetic valve is movable between a radially compressed configuration and a radially expanded configuration, and wherein the at least one flex sensor comprises a non-bending portion and a bending portion configured to flex relative to the non-bending portion.

According to some embodiments, responsive to an output of the at least one flex sensor, the control unit is configured to generate a signal indicative of a diameter of the prosthetic valve.

According to some embodiments, the prosthetic valve further comprises at least one actuator assembly, wherein the delivery apparatus further comprises an actuation member releasably coupled to the at least one actuator assembly, and wherein the prosthetic valve is expandable from the radially compressed state to the radially expanded state upon actuating the at least one actuator assembly by the at least one actuation member.

According to some embodiments, the non-bending portion of the at least one flex sensor is coupled to the at least one actuator assembly.

According to some embodiments, the delivery assembly further comprises at least one communication channel, a first end of the at least one communication channel coupled to the at least one flex sensor and a second end of the at least one communication channel extending towards the handle, wherein the at least one communication channel is retractable from the prosthetic valve.

According to some embodiments, the flex sensing assembly further comprises a sensor shaft extending distally from the handle, and wherein at least a portion of the at least one communication channel extends through the sensor shaft.

According to some embodiments, the delivery assembly further comprises: at least one sensor housing attached to a strut; and at least one detachable shaft extending distally from the handle, and detachably coupled to the sensor housing, wherein the at least one flex sensor is locally attached to the at least one sensor housing; wherein at least a portion of the at least one communication channel extends through the at least one detachable shaft; wherein the communication channel is detachably coupled to the at least one flex sensor; wherein the detachable shaft is configured isolate the at least one communication channel from ambient flow, when the detachable shaft is coupled to the sensor housing; and wherein the at least one communication channel is axially movable relative to the at least one detachable shaft, when the at least one communication channel is detached from the at least one sensor.

According to some embodiments, the at least one communication channel is detachable from the at least one flex sensor upon application of a pull force on the at least one communication channel, and wherein the magnitude of the pull force is higher than a predetermined threshold magnitude.

According to some embodiments, wherein the sensor housing comprises a sensor housing proximal threaded end, and wherein the detachable shaft comprises a detachable shaft distal threaded end, configured to engage with the sensor housing proximal threaded end.

According to some embodiments, the at least one flex sensor is an optic flex sensor configured to generate an optic signal, the at least one communication channel being at least one optic conductor, and wherein the at least one optic conductor is detachably optically coupled to the at least one optic flex sensor.

According to some embodiments, the at least one flex sensor is coupled to the strut via at least one coupling member.

According to some embodiments, the at least one coupling member comprises at least one of: a suture, a band, a tube, and/or a sleeve, and wherein the at least one flex sensor is slidable relative to the at least one coupling member upon application of a force exceeding the frictional force applied by the at least one coupling member on the at least one flex sensor.

According to some embodiments, the strut to which the at least one flex sensor is coupled, comprises at least two strut apertures through which the at least one flex sensor extends.

According to some embodiments, the at least one flex sensor comprises a variable resistance element, configured to vary its electrical resistivity in response to the extent of bending applied thereto.

According to some embodiments, the variable resistance element comprises a strain gauge.

According to some embodiments, the variable resistance element comprises a conductive material layer.

According to some embodiments, the at least one flex sensor is an optic flex sensor configured to generate an optic signal.

According to some embodiments, the at least one optic flex sensor comprises a plurality of axially spaced Fiber Bragg Gratings.

According to some embodiments, the delivery assembly further comprises at least one optic conductor is detachably optically coupled to the at least one optic flex sensor.

According to some embodiments, the flex sensing assembly further comprises at least one flexible distal extension, attached to and extending distally from the at least one flex sensor.

According to some embodiments, the at least one flexible distal extension is resiliently curved sideways.

According to some embodiments, the at least one flexible distal extension comprises: a first flexible distal extension comprising a first distal loop, wherein the first flexible distal extension is attached to and extends distally from the first flex sensor; and a second flexible distal extension comprising a second distal loop, wherein the second flexible distal extension is attached to and extends distally from the second flex sensor, wherein the flex sensing assembly further comprises a flexible elongate member extending distally from the handle and through the first distal loop and the second distal loop, and wherein the flexible elongate member is configured to couple the first flexible distal extension with the second flexible distal extension when extending through the first distal loop and the second distal loop, and to allow separation thereof upon being pulled therefrom.

According to some embodiments, at least one of the at least one flex sensors is coupled to at least two intersecting struts.

According to some embodiments, the at least one flex sensor comprises a first flex sensor coupled to a first strut, and a second flex sensor coupled to the second strut, wherein the at least one communication channel comprises a first communication channel coupled to the first flex sensor, and a second communication channel coupled to the second flex sensor, and wherein the first strut and the second strut are intersecting with each other.

According to some embodiments, the delivery assembly further comprises: an inflatable balloon, the inflatable balloon positioned within the prosthetic valve; a reservoir containing a predetermined volume of inflation fluid; a pump in fluid communication with the reservoir; and a fluid flow channel, a distal end of the fluid flow channel in fluid communication with an opening of the inflatable balloon and a proximal end of the fluid flow channel in fluid communication with the pump, wherein, movement of the prosthetic valve between the radially compressed configured to the radially expanded configuration is responsive to an inflation of the inflatable balloon, and wherein the pump is configured to generate flow of the inflation fluid into the inflatable balloon via the fluid flow channel.

According to some embodiments, the delivery assembly further comprises a pressure sensor configured to measure pressure of the inflation fluid, wherein, responsive to the measured pressure of the inflation fluid, the pump is further configured to adjust the generated flow of the inflation fluid.

According to some embodiments, the pressure sensor is positioned within the inflation fluid.

According to another aspect of the invention, a delivery assembly is provided, the delivery assembly comprising: a prosthetic valve comprising a plurality of intersecting struts, and a delivery apparatus comprising: a handle; a delivery shaft extending distally from the handle; and a flex sensing assembly, comprising: at least one flex sensor coupled to at least one of the plurality of struts; and at least one communication channel, a first end of the at least one communication channel coupled to the at least one flex sensor and a second end of the at least one communication channel extending towards the handle, wherein the prosthetic valve is movable between a radially compressed configuration and a radially expanded configuration, and wherein the at least one communication channel is retractable from the prosthetic valve.

According to some embodiments, the at least one flex sensor comprises a non-bending portion and a bending portion configured to flex relative to the non-bending portion.

According to some embodiments, the prosthetic valve further comprises at least one actuator assembly, wherein the delivery apparatus further comprises an actuation member releasably coupled to the at least one actuator assembly, and wherein the prosthetic valve is expandable from the radially compressed state to the radially expanded state upon actuating the at least one actuator assembly by the at least one actuation member.

According to some embodiments, the prosthetic valve further comprises at least one actuator assembly, wherein the delivery apparatus further comprises an actuation member releasably coupled to the at least one actuator assembly, wherein the prosthetic valve is expandable from the radially compressed state to the radially expanded state upon actuating the at least one actuator assembly by the at least one actuation member, and wherein the non-bending portion of the at least one flex sensor is coupled to the at least one actuator assembly.

According to some embodiments, the flex sensing assembly further comprises a sensor shaft extending distally from the handle, wherein at least a portion of the at least one communication channel extends through the sensor shaft.

According to some embodiments, the delivery assembly further comprises: at least one sensor housing attached to a strut; and at least one detachable shaft extending distally from the handle, and detachably coupled to the sensor housing, wherein the at least one flex sensor is locally attached to the at least one sensor housing; wherein at least a portion of the at least one communication channel extends through the at least one detachable shaft; wherein the communication channel is detachably coupled to the at least one flex sensor; wherein the detachable shaft is configured isolate the at least one communication channel from ambient flow, when the detachable shaft is coupled to the sensor housing; and wherein the at least one communication channel is axially movable relative to the at least one detachable shaft, when the at least one communication channel is detached from the at least one sensor.

According to some embodiments, the at least one communication channel is detachable from the at least one flex sensor upon application of a pull force on the at least one communication channel, wherein the magnitude of the pull force is higher than a predetermined threshold magnitude.

According to some embodiments, the sensor housing comprises a sensor housing proximal threaded end, and wherein the detachable shaft comprises a detachable shaft distal threaded end, configured to engage with the sensor housing proximal threaded end.

According to some embodiments, the at least one flex sensor is coupled to the strut via at least one coupling member.

According to some embodiments, the at least one coupling member comprises at least one of: a suture, a band, a tube, and/or a sleeve, and wherein the at least one flex sensor is slidable relative to the at least one coupling member upon application of a force exceeding the frictional force applied by the at least one coupling member on the at least one flex sensor.

According to some embodiments, the strut to which the at least one flex sensor is coupled comprises at least two strut apertures through which the at least one flex sensor extends.

According to some embodiments, the at least one flex sensor comprises a variable resistance element, configured to vary its electrical resistivity in response to the extent of bending applied thereto.

According to some embodiments, the variable resistance element comprises a strain gauge.

According to some embodiments, the variable resistance element comprises a conductive material layer.

According to some embodiments, the at least one flex sensor is an optic flex sensor configured to generate an optic signal, and wherein the at least one transmission line is an optic conductor.

According to some embodiments, the at least one optic flex sensor comprises a plurality of axially spaced Fiber Bragg Gratings.

According to some embodiments, the at least one optic conductor is detachably optically coupled to the at least one optic flex sensor.

According to some embodiments, the flex sensing assembly further comprises at least one flexible distal extension, attached to and extending distally from the at least one flex sensor.

According to some embodiments, the at least one flexible distal extension is resiliently curved sideways.

According to some embodiments, the at least one flexible distal extension comprises: a first flexible distal extension comprising a first distal loop, wherein the first flexible distal extension is attached to and extends distally from the first flex sensor; and a second flexible distal extension comprising a second distal loop, wherein the second flexible distal extension is attached to and extends distally from the second flex sensor, wherein the flex sensing assembly further comprises a flexible elongate member extending distally from the handle and through the first distal loop and the second distal loop, and wherein the flexible elongate member is configured to couple the first flexible distal extension with the second flexible distal extension when extending through the first distal loop and the second distal loop, and to allow separation thereof upon being pulled therefrom.

According to some embodiments, at least one of the at least one flex sensors is coupled to at least two intersecting struts.

According to some embodiments, the at least one flex sensor comprises a first flex sensor coupled to a first strut, and a second flex sensor coupled to the second strut, wherein the at least one communication channel comprises a first communication channel coupled to the first flex sensor, and a second communication channel coupled to the second flex sensor, and wherein the first strut and the second strut are intersecting with each other.

According to some embodiments, the delivery assembly further comprises: an inflatable balloon, the inflatable balloon positioned within the prosthetic valve; a reservoir containing a predetermined volume of inflation fluid; a pump in fluid communication with the reservoir; and a fluid flow channel, a distal end of the fluid flow channel in fluid communication with an opening of the inflatable balloon and a proximal end of the fluid flow channel in fluid communication with the pump, wherein, movement of the prosthetic valve between the radially compressed configured to the radially expanded configuration is responsive to an inflation of the inflatable balloon, and wherein the pump is configured to generate flow of the inflation fluid into the inflatable balloon via the fluid flow channel.

According to some embodiments, the delivery assembly further comprises a pressure sensor configured to measure pressure of the inflation fluid, wherein, responsive to the measured pressure of the inflation fluid, the pump is further configured to adjust the generated flow of the inflation fluid.

According to some embodiments, the pressure sensor is positioned within the inflation fluid.

According to another aspect of the invention, a delivery assembly is provided, the delivery assembly comprising: a prosthetic valve movable between a radially compressed configuration and a radially expanded configuration, and a delivery apparatus comprising: a handle; a delivery shaft extending distally from the handle; an inflatable balloon, the inflatable balloon positioned within the prosthetic valve; a reservoir containing a predetermined volume of inflation fluid; a pump in fluid communication with the reservoir; and a fluid flow channel, a distal end of the fluid flow channel in fluid communication with an opening of the inflatable balloon and a proximal end of the fluid flow channel in fluid communication with the pump; a diameter sensor, an output of the diameter sensor responsive to a radial diameter of the prosthetic valve and/or the inflatable balloon; and a control unit in communication with the pump and the diameter sensor, wherein, responsive to an inflation of the inflatable balloon, the prosthetic valve is movable between a radially compressed configuration and a radially expanded configuration, wherein the pump is configured to generate flow of the inflation fluid into the inflatable balloon via the fluid flow channel, and wherein, responsive to the output of the diameter sensor, the control circuitry is configured to control the pump to adjust the flow of the inflation fluid.

According to some embodiments, the control unit is further configured, responsive to the output of the diameter sensor, to determine an indication of a radial diameter of the prosthetic valve and/or the inflatable balloon, the adjustment of the flow of the inflation fluid further responsive to the determined diameter indication.

According to some embodiments, the determined diameter indication comprises a change in radial diameter.

According to some embodiments, the diameter sensor comprises: at least one radially translatable member juxtaposed with an outer surface of the inflatable balloon such that the inflation of the balloon radially translates the at least one radially translatable member; and a linear displacement sensor coupled to the at least one radially translatable member and in communication with the control unit, an output of the linear displacement sensor configured to be responsive to the radial translation of the at least one radially translatable member.

According to some embodiments, the at least one radially translatable member surrounds the outer surface of the inflatable balloon.

According to some embodiments, the at least one radially translatable member is loop shaped.

According to some embodiments, the at least one radially translatable member comprises: a first balloon portion; a second balloon portion; and a connection portion, each of the first balloon portion and the second balloon portion extending from a first end of the connection portion, and a second end of the connection portion coupled to the linear displacement sensor.

According to some embodiments, each of the first balloon portion and the second balloon portion extends in a respective direction, the direction of extension of the second balloon portion generally opposing the direction of extension of the first balloon portion.

According to some embodiments, the diameter sensor comprises at least one flex sensor, wherein the prosthetic valve comprises a plurality of intersecting struts, the at least one flex sensor coupled to at least one of the plurality of struts.

According to some embodiments, the at least one flex sensor comprises a non-bending portion and a bending portion configured to flex relative to the non-bending portion.

According to some embodiments, the at least one flex sensor comprises a first flex sensor coupled to a first of the plurality of struts and a second flex sensor coupled to a second of a plurality of struts, wherein the first of the plurality of struts and the second of the plurality of struts intersect each other.

According to some embodiments, the delivery assembly further comprises at least one communication channel, a first end of the at least one communication channel coupled to the at least one flex sensor, wherein the at least one communication channel is retractable from the prosthetic valve.

According to some embodiments, the diameter sensor comprises at least one strain gauge circumferentially disposed on an outer surface of the inflatable balloon.

According to some embodiments, the delivery assembly further comprises a pressure sensor configured to measure pressure of the inflation fluid, wherein, responsive to the measured pressure of the inflation fluid, the pump is further configured to adjust the generated flow of the inflation fluid.

According to some embodiments, the delivery assembly further comprises a pressure sensor configured to measure pressure of the inflation fluid, wherein the adjustment of the flow of the inflation fluid is responsive to a predetermined function of the measured pressure and the determined diameter indication.

According to some embodiments, the pressure sensor is positioned within the inflation fluid.

According to some embodiments, the pressure sensor is positioned within the fluid flow channel.

According to another aspect of the invention, a delivery assembly is provided, the delivery assembly comprising: a prosthetic valve movable between a radially compressed configuration and a radially expanded configuration, and a delivery apparatus comprising: a handle; a delivery shaft extending distally from the handle; an inflatable balloon, the inflatable balloon positioned within the prosthetic valve; a reservoir containing a predetermined volume of inflation fluid; a pump in fluid communication with the reservoir; a fluid flow channel, a distal end of the fluid flow channel in fluid communication with an opening of the inflatable balloon and a proximal end of the fluid flow channel in fluid communication with the pump; an imager configured to image the prosthetic valve; and a control unit in communication with the pump and the imager, wherein, responsive to an inflation of the inflatable balloon, the prosthetic valve is movable between a radially compressed configuration and a radially expanded configuration, wherein the pump is configured to generate flow of the inflation fluid into the inflatable balloon via the fluid flow channel, and wherein, responsive to the output of the imager, the control circuitry is configured to control the pump to adjust the flow of the inflation fluid.

According to some embodiments, the prosthetic valve comprises at least one radiopaque marker, the configuration of the imager to image the prosthetic valve comprises a configuration to image the at least one radiopaque marker.

According to some embodiments, the at least one radiopaque marker comprises radiopaque coating.

According to some embodiments, the at least one radiopaque marker comprises a plurality of radiopaque markers exhibiting predetermined spaces therebetween.

According to some embodiments, the delivery assembly further comprises a pressure sensor configured to measure pressure of the inflation fluid, wherein, responsive to the measured pressure of the inflation fluid, the pump is further configured to adjust the generated flow of the inflation fluid.

According to some embodiments, the delivery assembly further comprises a pressure sensor configured to measure pressure of the inflation fluid, wherein the adjustment of the flow of the inflation fluid is responsive to a predetermined function of the measured pressure and the determined diameter indication.

According to some embodiments, the pressure sensor is positioned within the inflation fluid.

According to some embodiments, the pressure sensor is positioned within the fluid flow channel.

According to another aspect of the invention, a delivery assembly is provided, the delivery assembly comprising: a prosthetic valve movable between a radially compressed configuration and a radially expanded configuration, and a delivery apparatus comprising: a handle; a delivery shaft extending distally from the handle; an inflatable balloon, the inflatable balloon positioned within the prosthetic valve; a reservoir containing a predetermined volume of inflation fluid; a pump in fluid communication with the reservoir; a fluid flow channel, a distal end of the fluid flow channel in fluid communication with an opening of the inflatable balloon and a proximal end of the fluid flow channel in fluid communication with the pump; an imager configured to image the inflatable balloon; and a control unit in communication with the pump and the imager, wherein, responsive to an inflation of the inflatable balloon, the prosthetic valve is movable between a radially compressed configuration and a radially expanded configuration, wherein the pump is configured to generate flow of the inflation fluid into the inflatable balloon via the fluid flow channel, and wherein, responsive to the output of the imager, the control circuitry is configured to control the pump to adjust the flow of the inflation fluid.

According to some embodiments, the inflatable balloon comprises at least one radiopaque marker, the configuration of the imager to image the inflatable balloon comprises a configuration to image the at least one radiopaque marker.

According to some embodiments, wherein the at least one radiopaque marker comprises radiopaque coating.

According to some embodiments, the at least one radiopaque marker comprises a plurality of radiopaque markers exhibiting predetermined spaces therebetween.

According to some embodiments, the control unit is further configured, responsive to the output of the imager, to determine an indication of a radial diameter of the prosthetic valve and/or the inflatable balloon, the adjustment of the flow of the inflation fluid further responsive to the determined diameter indication.

According to some embodiments, the determined diameter indication comprises a change in radial diameter.

According to some embodiments, the delivery assembly further comprises a pressure sensor configured to measure pressure of the inflation fluid, wherein, responsive to the measured pressure of the inflation fluid, the pump is further configured to adjust the generated flow of the inflation fluid.

According to some embodiments, the delivery assembly further comprises a pressure sensor configured to measure pressure of the inflation fluid, wherein the adjustment of the flow of the inflation fluid is responsive to a predetermined function of the measured pressure and the determined diameter indication.

According to some embodiments, the pressure sensor is positioned within the inflation fluid.

According to some embodiments, the pressure sensor is positioned within the fluid flow channel.

According to another aspect of the invention, a delivery assembly is provided, the delivery assembly comprising: a handle; a delivery shaft extending distally from the handle; an inflatable balloon; a reservoir containing a predetermined volume of inflation fluid; a pump in fluid communication with the reservoir; a fluid flow channel, a distal end of the fluid flow channel in fluid communication with an opening of the inflatable balloon and a proximal end of the fluid flow channel in fluid communication with the pump, a control unit in communication with the pump; at least one radially translatable member juxtaposed with an outer surface of the inflatable balloon such that the inflation of the balloon radially translates the at least one radially translatable member; and a linear displacement sensor coupled to the at least one radially translatable member and in communication with the control unit, an output of the linear displacement sensor configured to be responsive to the radial translation of the at least one radially translatable member, wherein the pump is configured to generate flow of the inflation fluid into the inflatable balloon via the fluid flow channel, and wherein, responsive to the output of the linear displacement sensor, the control circuitry is configured to control the pump to adjust the flow of the inflation fluid.

According to some embodiments, the control unit is further configured, responsive to the output of the linear displacement sensor, to determine an indication of a radial diameter of the prosthetic valve and/or the inflatable balloon, the adjustment of the flow of the inflation fluid further responsive to the determined diameter indication.

According to some embodiments, the determined diameter indication comprises a change in radial diameter.

According to some embodiments, the at least one radially translatable member surrounds the outer surface of the inflatable balloon.

According to some embodiments, the at least one radially translatable member is loop shaped.

According to some embodiments, the at least one radially translatable member comprises: a first balloon portion; a second balloon portion; and a connection portion, each of the first balloon portion and the second balloon portion extending from a first end of the connection portion, and a second end of the connection portion coupled to the linear displacement sensor.

According to some embodiments, each of the first balloon portion and the second balloon portion extends in a respective direction, the direction of extension of the second balloon portion generally opposing the direction of extension of the first balloon portion.

According to some embodiments, the delivery assembly further comprises a pressure sensor configured to measure pressure of the inflation fluid, wherein, responsive to the measured pressure of the inflation fluid, the pump is further configured to adjust the generated flow of the inflation fluid.

According to some embodiments, the delivery assembly further comprises a pressure sensor configured to measure pressure of the inflation fluid, wherein the adjustment of the flow of the inflation fluid is responsive to a predetermined function of the measured pressure and the determined diameter indication.

According to some embodiments, the pressure sensor is positioned within the inflation fluid.

According to some embodiments, the pressure sensor is positioned within the fluid flow channel.

According to another aspect of the invention, a delivery assembly is provided, the delivery assembly comprising: a handle; a delivery shaft extending distally from the handle; an inflatable balloon; a reservoir containing a predetermined volume of inflation fluid; a pump in fluid communication with the reservoir; a fluid flow channel, a distal end of the fluid flow channel in fluid communication with an opening of the inflatable balloon and a proximal end of the fluid flow channel in fluid communication with the pump; a control unit in communication with the pump; and at least one strain gauge circumferentially disposed on an outer surface of the inflatable balloon, wherein the pump is configured to generate flow of the inflation fluid into the inflatable balloon via the fluid flow channel, and wherein, responsive to an output of the at least one strain gauge, the control circuitry is configured to control the pump to adjust the flow of the inflation fluid.

According to some embodiments, the control unit is further configured, responsive to the output of the at least one strain gauge, to determine an indication of a radial diameter of the inflatable balloon, the adjustment of the flow of the inflation fluid further responsive to the determined diameter indication.

According to some embodiments, the determined diameter indication comprises a comprises a change in radial diameter.

According to some embodiments, the delivery assembly further comprises a pressure sensor configured to measure pressure of the inflation fluid, wherein, responsive to the measured pressure of the inflation fluid, the pump is further configured to adjust the generated flow of the inflation fluid.

According to some embodiments, the delivery assembly further comprises a pressure sensor configured to measure pressure of the inflation fluid, wherein the adjustment of the flow of the inflation fluid is responsive to a predetermined function of the measured pressure and the determined diameter indication.

According to some embodiments, the pressure sensor is positioned within the inflation fluid.

According to some embodiments, the pressure sensor is positioned within the fluid flow channel.

According to another aspect of the invention, a delivery assembly is provided, the delivery assembly comprising: a handle; a delivery shaft extending distally from the handle; an inflatable balloon, the inflatable balloon positioned within the prosthetic valve; a reservoir containing a predetermined volume of inflation fluid; a pump in fluid communication with the reservoir; a fluid flow channel, a distal end of the fluid flow channel in fluid communication with an opening of the inflatable balloon and a proximal end of the fluid flow channel in fluid communication with the pump; an imager configured to image the inflatable balloon; and a control unit in communication with the pump and the imager, wherein the pump is configured to generate flow of the inflation fluid into the inflatable balloon via the fluid flow channel, and wherein, responsive to the output of the imager, the control circuitry is configured to control the pump to adjust the flow of the inflation fluid.

According to some embodiments, the inflatable balloon comprises at least one radiopaque marker, the configuration of the imager to image the inflatable balloon comprises a configuration to image the at least one radiopaque marker.

According to some embodiments, the at least one radiopaque marker comprises radiopaque coating.

According to some embodiments, the at least one radiopaque marker comprises a plurality of radiopaque markers exhibiting predetermined spaces therebetween.

According to some embodiments, the control unit is further configured, responsive to the output of the imager, to determine an indication of a radial diameter of the inflatable balloon, the adjustment of the flow of the inflation fluid further responsive to the determined diameter indication.

According to some embodiments, the determined diameter indication comprises a change in radial diameter.

According to some embodiments, the delivery assembly further comprises a pressure sensor configured to measure pressure of the inflation fluid, wherein, responsive to the measured pressure of the inflation fluid, the pump is further configured to adjust the generated flow of the inflation fluid.

According to some embodiments, the delivery assembly further comprises a pressure sensor configured to measure pressure of the inflation fluid, wherein the adjustment of the flow of the inflation fluid is responsive to a predetermined function of the measured pressure and the determined diameter indication.

According to some embodiments, the pressure sensor is positioned within the inflation fluid.

According to some embodiments, the pressure sensor is positioned within the fluid flow channel.

According to another aspect of the invention, a delivery method for a prosthetic valve comprising a plurality of intersecting struts is provided, the method comprising: coupling at least one flex sensor to at least one of the plurality of struts; delivering the prosthetic valve to a predetermined anatomical location; moving the delivered prosthetic valve between a radially compressed configuration and a radially expanded configuration; and responsive to an output of the at least one flex sensor, generating a signal indicative of a diameter of the prosthetic valve.

According to some embodiments, the at least one flex sensor comprises a non-bending portion and a bending portion configured to flex relative to the non-bending portion.

According to some embodiments, the method further comprises retracting at least one communication channel from the prosthetic valve, the at least one communication channel coupled to the at least one flex sensor.

According to some embodiments, the method further comprises applying a pull force on the at least one communication channel, the magnitude of the pull force higher than predetermined threshold magnitude, wherein the at least one communication channel is detachable from the at least one flex sensor upon the application of the pull force.

According to some embodiments, at least one of the at least one flex sensors is coupled to at least two intersecting struts.

According to some embodiments, the coupling of the at least one flex sensor to the at least one strut comprises: coupling a first of the at least one flex sensor to a first of the at least one strut; and coupling a second of the at least one flex sensor to a second of the at least one strut, wherein the first strut and the second strut are intersecting with each other.

According to some embodiments, the method further comprises pumping inflation fluid into an inflatable balloon positioned within the prosthetic valve, the pumped inflation fluid expanding the inflatable balloon thereby causing the moving of the delivered prosthetic valve from the radially compressed configuration to the radially expanded configuration.

According to another aspect of the invention, a delivery method for a prosthetic valve comprising a plurality of intersecting struts is provided, the method comprising: coupling at least one flex sensor to at least one of the plurality of struts; delivering the prosthetic valve to a predetermined anatomical location; and moving the delivered prosthetic valve between a radially compressed configuration and a radially expanded configuration, wherein the moving to the radially expanded configuration flexes a bending portion of the at least one flex sensor relative to a non-bending portion of the at least one flex sensor.

According to some embodiments, the method further comprises, responsive to an output of the at least one flex sensor, generating a signal indicative of a diameter of the prosthetic valve.

According to some embodiments, the method further comprises retracting at least one communication channel from the prosthetic valve, the at least one communication channel coupled to the at least one flex sensor.

According to some embodiments, the method further comprises applying a pull force on the at least one communication channel, the magnitude of the pull force higher than predetermined threshold magnitude, wherein the at least one communication channel is detachable from the at least one flex sensor upon the application of the pull force.

According to some embodiments, at least one of the at least one flex sensors is coupled to at least two intersecting struts.

According to some embodiments, the coupling of the at least one flex sensor to the at least one strut comprises: coupling a first of the at least one flex sensor to a first of the at least one strut; and coupling a second of the at least one flex sensor to a second of the at least one strut, wherein the first strut and the second strut are intersecting with each other.

According to some embodiments, the method further comprises pumping inflation fluid into an inflatable balloon positioned within the prosthetic valve, the pumped inflation fluid expanding the inflatable balloon thereby causing the moving of the delivered prosthetic valve from the radially compressed configuration to the radially expanded configuration.

According to another aspect of the invention, a delivery method for a prosthetic valve comprising a plurality of intersecting struts is provided, the method comprising: coupling at least one flex sensor to at least one of the plurality of struts, a communication channel coupled to the at least one flex sensor; delivering the prosthetic valve to a predetermined anatomical location; moving the delivered prosthetic valve between a radially compressed configuration and a radially expanded configuration; and subsequent to the moving to the radially expanded configuration, retracting the communication channel from the prosthetic valve.

According to some embodiments, the method further comprises, responsive to an output of the at least one flex sensor, generating a signal indicative of a diameter of the prosthetic valve.

According to some embodiments, the at least one flex sensor comprises a non-bending portion and a bending portion configured to flex relative to the non-bending portion.

According to some embodiments, the method further comprises applying a pull force on the at least one communication channel, the magnitude of the pull force higher than predetermined threshold magnitude, wherein the at least one communication channel is detachable from the at least one flex sensor upon the application of the pull force.

According to some embodiments, at least one of the at least one flex sensors is coupled to at least two intersecting struts.

According to some embodiments, the coupling of the at least one flex sensor to the at least one strut comprising: coupling a first of the at least one flex sensor to a first of the at least one strut; and coupling a second of the at least one flex sensor to a second of the at least one strut, and wherein the first strut and the second strut are intersecting with each other.

According to some embodiments, the method further comprises pumping inflation fluid into an inflatable balloon positioned within the prosthetic valve, the pumped inflation fluid expanding the inflatable balloon thereby causing the moving of the delivered prosthetic valve from the radially compressed configuration to the radially expanded configuration.

According to another aspect of the invention, a delivery method for a prosthetic valve is provided, the method comprising: delivering the prosthetic valve to a predetermined anatomical location; pumping inflation fluid into an inflatable balloon positioned within the prosthetic valve, the pumped inflation fluid inflating the inflatable balloon thereby causing the delivered prosthetic valve to be moved from a radially compressed configuration to a radially expanded configuration; determining an indication of a radial diameter of the prosthetic valve and/or the inflatable balloon; and responsive to the determined radial diameter indication, adjusting the flow of the inflation fluid.

According to some embodiments, the determining the diameter indication comprises determining a change in the radial diameter.

According to some embodiments, the method further comprises: juxtaposing at least one radially translatable member with an outer surface of the inflatable balloon such that the inflation of the balloon radially translates the at least one radially translatable member, wherein the radial diameter indication is responsive to a linear displacement sensor coupled to the at least one radially translatable member, an output of the linear displacement sensor configured to be responsive to the radial translation of the at least one radially translatable member.

According to some embodiments, the juxtaposing comprises surrounding the outer surface of the inflatable balloon.

According to some embodiments, the method further comprises, responsive to the output of the linear displacement sensor, determining an indication of a diameter of the prosthetic valve, the adjustment of the flow of the inflation fluid further responsive to the determined diameter indication.

According to some embodiments, the method further comprises: juxtaposing at least one strain gauge with an outer surface of the inflatable balloon, wherein the radial diameter indication is responsive to an output of the at least one strain gauge.

According to some embodiments, the method further comprises imaging the prosthetic valve, wherein the radial diameter indication is responsive to the imaging of the prosthetic valve.

According to some embodiments, the method further comprises positioning at least one radiopaque marker on the prosthetic valve, the imaging of the prosthetic valve comprising imaging the positioned at least one radiopaque marker.

According to some embodiments, the method further comprises imaging the inflatable balloon, wherein the radial diameter indication is responsive to the imaging of the inflatable balloon.

According to some embodiments, the method further comprises positioning at least one radiopaque marker on the inflatable balloon, the imaging of the prosthetic valve comprising imaging the positioned at least one radiopaque marker.

According to some embodiments, the method further comprises: measuring pressure of the inflation fluid; and responsive to the measured pressure, adjusting the flow of the inflation fluid.

According to some embodiments, the method further comprises coupling at least one flex sensor to at least one of a plurality of struts of the prosthetic valve, wherein the radial diameter indication is responsive to an output of the at least one flex sensor.

According to some embodiments, the at least one flex sensor comprises a non-bending portion and a bending portion configured to flex relative to the non-bending portion.

According to some embodiments, the method further comprises retracting at least one communication channel from the prosthetic valve, the at least one communication channel coupled to the at least one flex sensor.

According to some embodiments, the method further comprises: measuring pressure of the inflation fluid; and responsive to a predetermined function of the determined diameter indication and measured pressure, adjusting the flow of the inflation fluid.

According to another aspect of the invention, a delivery method for an inflatable balloon is provided, the method comprising: delivering an inflatable balloon to a predetermined anatomical location; pumping inflation fluid into the delivered inflatable balloon, the pumped inflation fluid inflating the inflatable balloon; juxtaposing at least one radially translatable member with an outer surface of the inflatable balloon such that the inflation of the balloon radially translates the at least one radially translatable member; and responsive to a linear displacement sensor coupled to the at least one radially translatable member, adjusting the flow of the inflation fluid, wherein an output of the linear displacement sensor is configured to be responsive to the radial translation of the at least one radially translatable member.

According to some embodiments, the juxtaposing comprises surrounding the outer surface of the inflatable balloon.

According to some embodiments, the method further comprises, responsive to the output of the linear displacement sensor, determining an indication of a diameter of the prosthetic valve, the adjustment of the flow of the inflation fluid further responsive to the determined diameter indication.

According to some embodiments, the determining the radial diameter indication comprises determining a change in the radial diameter.

According to some embodiments, the method further comprises measuring pressure of the inflation fluid, wherein the adjustment of the flow of the inflation fluid is further responsive to a predetermined function of the determined diameter indication and the measured pressure.

According to some embodiments, the method further comprises measuring pressure of the inflation fluid, wherein the adjustment of the flow of the inflation fluid is further responsive to the measured pressure.

According to another aspect of the invention, a delivery method for an inflatable balloon is provided, the method comprising: delivering an inflatable balloon to a predetermined anatomical location; pumping inflation fluid into the delivered inflatable balloon, the pumped inflation fluid inflating the inflatable balloon; juxtaposing a strain gauge with an outer surface of the inflatable balloon; and responsive to an output of the strain gauge, adjusting the flow of the inflation fluid.

According to some embodiments, the method further comprises, responsive to an output of the at least one strain gauge, determining an indication of a diameter of the inflatable balloon, the adjustment of the flow of the inflation fluid further responsive to the determined diameter indication.

According to some embodiments, the determining the radial diameter indication comprises determining a change in the radial diameter.

According to some embodiments, the method further comprises measuring pressure of the inflation fluid, wherein the adjustment of the flow of the inflation fluid is further responsive to a predetermined function of the determined diameter indication and the measured pressure.

According to some embodiments, the method further comprises measuring pressure of the inflation fluid, wherein the adjustment of the flow of the inflation fluid is further responsive to the measured pressure.

According to another aspect of the invention, a delivery method for an inflatable balloon is provided, the method comprising: delivering an inflatable balloon to a predetermined anatomical location; pumping inflation fluid into the delivered inflatable balloon, the pumped inflation fluid inflating the inflatable balloon; imaging the inflatable balloon; and responsive to the imaging, adjusting the flow of the inflation fluid.

According to some embodiments, the method further comprises positioning at least one radiopaque marker on the inflatable balloon, the imaging of the prosthetic valve comprising imaging the positioned at least one radiopaque marker.

According to some embodiments, the method further comprises, responsive to the imaging, determining an indication of a diameter of the inflatable balloon, the adjustment of the flow of the inflation fluid further responsive to the determined diameter indication.

According to some embodiments, the method further comprises: measuring pressure of the inflation fluid, wherein the adjustment of the flow of the inflation fluid is further responsive to the measured pressure.

According to some embodiments, the method further comprises measuring pressure of the inflation fluid, wherein the adjustment of the flow of the inflation fluid is further responsive to a predetermined function of the determined diameter indication and measured pressure.

Certain embodiments of the present invention may include some, all, or none of the above advantages. Further advantages may be readily apparent to those skilled in the art from the figures, descriptions, and claims included herein. Aspects and embodiments of the invention are further described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

The following embodiments and aspects thereof are described and illustrated in conjunction with systems, tools and methods which are meant to be exemplary and illustrative, but not limiting in scope. In various embodiments, one or more of the above-described problems have been reduced or eliminated, while other embodiments are directed to other advantages or improvements.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures:

FIG. 3A shows a view in perspective of an inner member, according to some embodiments.

FIG. 3B shows a view in perspective of an actuator assembly, according to some embodiments.

FIG. 3C shows a view in perspective of a prosthetic valve including multiple actuator assemblies of the type shown in FIG. 3B.

DETAILED DESCRIPTION

Figure 1:
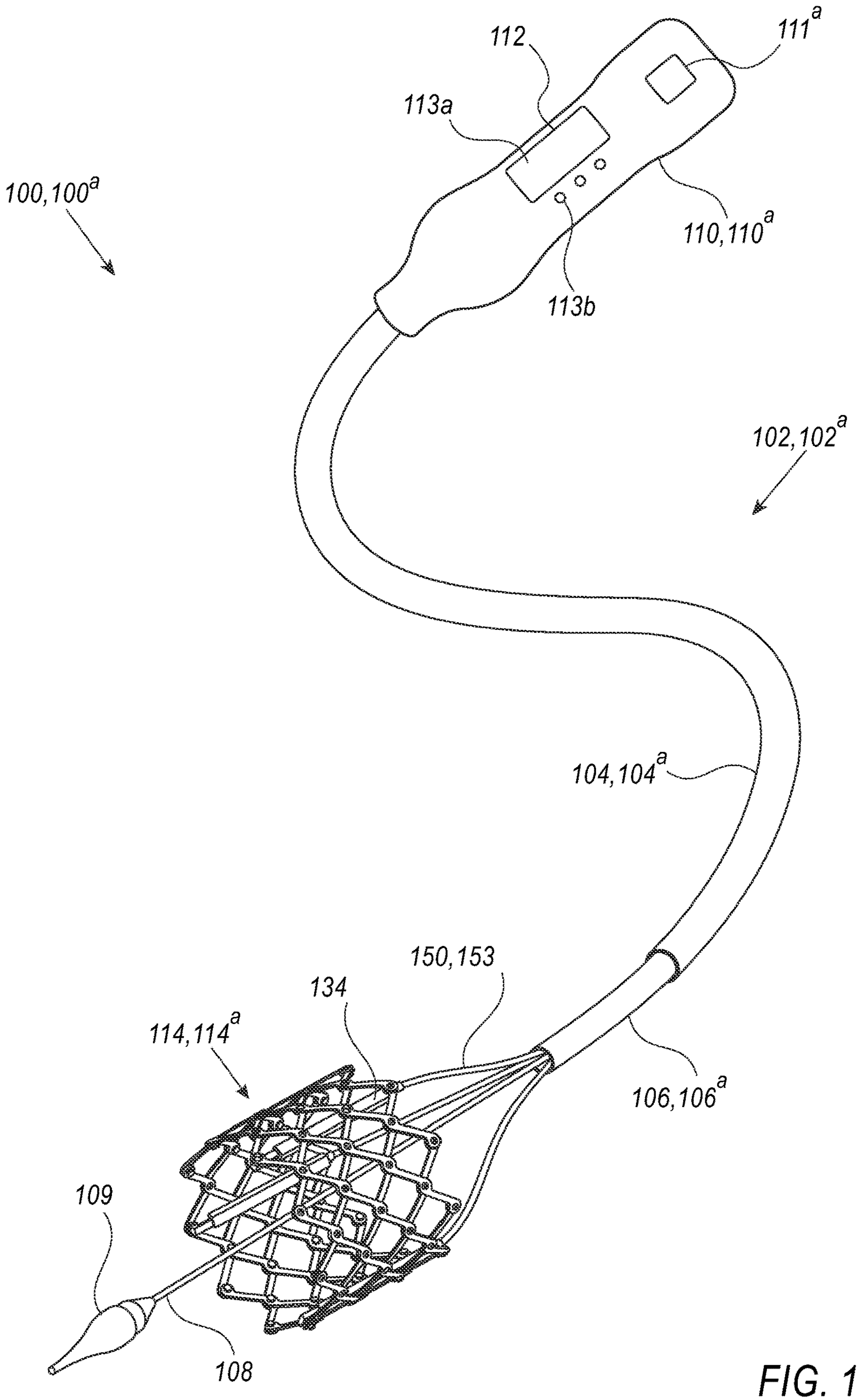
FIG. 1 shows a view in perspective of a delivery assembly comprising a delivery apparatus carrying a prosthetic valve, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. In the figures, like reference numerals refer to like parts throughout. In order to avoid undue clutter from having too many reference numbers and lead lines on a particular drawing, some components will be introduced via one or more drawings and not explicitly identified in every subsequent drawing that contains that component.

FIG. 1 shows a view in perspective of a delivery assembly 100, according to some embodiments. The delivery assembly 100 can include a prosthetic valve 114 and a delivery apparatus 102. The prosthetic valve 114 can be on or releasably coupled to the delivery apparatus 102. The delivery apparatus can include a handle 110 at a proximal end thereof, a nosecone shaft 108 extending distally from the handle 110, a nosecone 109 attached to the distal end of the nosecone shaft 108, a delivery shaft 106 extending over the nosecone shaft 108, and optionally an outer shaft 104 extending over the delivery shaft 106.

The term "proximal", as used herein, generally refers to the side or end of any device or a component of a device, which is closer to the handle 110 or an operator of the handle 110 when in use.

The term "distal", as used herein, generally refers to the side or end of any device or a component of a device, which is farther from the handle 110 or an operator of the handle 110 when in use.

The term "prosthetic valve", as used herein, refers to any type of a prosthetic valve deliverable to a patient's target site over a catheter, which is radially expandable and compressible between a radially compressed, or crimped, state, and a radially expanded state. Thus, a prosthetic valve 114 can be crimped or retained by a delivery apparatus 102 in a compressed state during delivery, and then expanded to the expanded state once the prosthetic valve 114 reaches the implantation site. The expanded state may include a range of diameters to which the valve may expand, between the compressed state and a maximal diameter reached at a fully expanded state. Thus, a plurality of partially expanded states may relate to any expansion diameter between radially compressed or crimped state, and maximally expanded state.

The term "plurality", as used herein, means more than one.

A prosthetic valve 114 of the current disclosure may include any prosthetic valve configured to be mounted within the native aortic valve, the native mitral valve, the native pulmonary valve, and the native tricuspid valve. While a delivery assembly 100 described in the current disclosure, includes a delivery apparatus 102 and a prosthetic valve 114, it should be understood that the delivery apparatus 102 according to any embodiment of the current disclosure can be used for implantation of other prosthetic devices aside from prosthetic valves, such as stents or grafts.

A catheter deliverable prosthetic valve 114 can be delivered to the site of implantation via the delivery assembly 100 carrying the valve 114 in a radially compress or crimped state, toward the target site, to be mounted against the native anatomy, by expanding the prosthetic valve 114 via various expansion mechanisms. Balloon expandable valves generally involve a procedure of inflating a balloon within a prosthetic valve, thereby expanding the prosthetic valve 114 within the desired implantation site. Once the valve is sufficiently expanded, the balloon is deflated and retrieved along with the delivery apparatus 102. Self-expandable valves include a frame that is shape-set to automatically expand as soon an outer retaining capsule, which may be also defined as the distal portion of an outer shaft (104) or the distal portion of a delivery shaft (106), is withdrawn proximally relative to the prosthetic valve. Mechanically expandable valves are a category of prosthetic valves that rely on a mechanical actuation mechanism for expansion. The mechanical actuation mechanism usually includes a plurality of expansion and locking assemblies, releasably coupled to respective actuation assemblies of the delivery apparatus 102, controlled via the handle 110 for actuating the expansion and locking assemblies to expand the prosthetic valve to a desired diameter. The expansion and locking assemblies may optionally lock the valve's diameter to prevent undesired recompression thereof, and disconnection of the actuation assemblies from the expansion and locking assemblies, to enable retrieval of the delivery apparatus 102 once the prosthetic valve is properly positioned at the desired site of implantation.

The delivery assembly 100 can be utilized, for example, to deliver a prosthetic aortic valve for mounting against the aortic annulus, to deliver a prosthetic mitral valve for mounting against the mitral annulus, or to deliver a prosthetic valve for mounting against any other native annulus.

The exemplary delivery assembly 100 illustrated in FIG. 1 may be a delivery assembly 100$^a$ comprising a delivery apparatus 102$^a$ for delivery and implantation of a mechanically expandable valve 114$^a$. According to some embodiments, the delivery apparatus 102$^a$ includes a balloon catheter 24 having an inflatable balloon (hidden from view) mounted on its distal end. The balloon expandable prosthetic valve 100$^a$ can be carried in a crimped state over the inflatable balloon, as shown in FIG. 1. Optionally, an outer shaft 20 can concentrically extend over the balloon catheter 24.

According to some embodiments, the prosthetic valve 114 is a mechanically expandable valve 114$^a$, and the delivery assembly 100 illustrated in FIG. 1 may be a delivery assembly 100$^a$ comprising a delivery apparatus 102$^a$ for delivery and implantation of a mechanically expandable valve 114$^a$. According to some embodiments, the delivery apparatus 102$^a$ further comprises a plurality of actuation assemblies 150 extending from the handle 110$^a$ through the delivery shaft 106$^a$. The actuation assemblies 150 can generally include actuators 151 (hidden from view in FIG. 1, visible in FIGS. 4A-4C) releasably coupled at their distal ends to respective expansion and locking assemblies 134 of the mechanically expandable valve 114$^a$, and sleeves 153 (annotated in FIG. 3) disposed around the respective actuators 151. Each actuator 151 may be axially movable relative to the sleeve 153 covering it.

The mechanically expandable valve 114$^a$ can be delivered to the site of implantation via a delivery assembly 100$^a$ carrying the valve 114$^a$ in a radially compressed or crimped state, toward the target site, to be mounted against the native anatomy, by expanding the valve 114$^a$ via a mechanical expansion mechanism, as will be elaborated below.

The nosecone 109 can be connected to the distal end of the nosecone shaft 108. A guidewire (not shown) can extend through a central lumen of the nosecone shaft 108 and an inner lumen of the nosecone 109, so that the delivery apparatus 102 can be advanced over the guidewire through the patient's vasculature.

A distal end portion of the outer shaft 104 can extend over the prosthetic valve 114 and contact the nosecone 109 in a delivery configuration of the delivery apparatus 102. Thus, the distal end portion of the outer shaft 104 can serve as a delivery capsule that contains, or houses, the prosthetic valve 114 in a radially compressed or crimped configuration for delivery through the patient's vasculature.

The outer shaft 104 and the delivery shaft 106 can be configured to be axially movable relative to each other, such that a proximally oriented movement of the outer shaft 104 relative to the delivery shaft 106, or a distally oriented movement of the delivery shaft 106 relative to the outer shaft 104, can expose the prosthetic valve from the outer shaft 104. In alternative embodiments, the prosthetic valve 114 is not housed within the outer shaft 104 during delivery. Thus, according to some embodiments, the delivery apparatus 102 does not include an outer shaft 104.

As mentioned above, the proximal ends of the nosecone shaft 108, the delivery shaft 106, components of the actuation assemblies 150, and when present—the outer shaft 104, can be coupled to the handle 110. During delivery of the prosthetic valve 114, the handle 110 can be maneuvered by an operator (e.g., a clinician or a surgeon) to axially advance or retract components of the delivery apparatus 102, such as the nosecone shaft 108, the delivery shaft 106, and/or the outer shaft 104, through the patient's vasculature, as well as to expand or contract the prosthetic valve 114, for example by maneuvering the actuation assemblies 150, and to disconnect the prosthetic valve 114 from the delivery apparatus 102, for example—by decoupling the actuators 151 from the actuator assemblies 134 of the valve 114, in order to retract it once the prosthetic valve is mounted in the implantation site.

The term "and/or" is inclusive here, meaning "and" as well as "or". For example, "delivery shaft 106 and/or outer shaft 104" encompasses, delivery shaft 106, outer shaft 104, and delivery shaft 106 with outer shaft 104; and, such "delivery shaft 106 and/or outer shaft 104" may include other elements as well.

According to some embodiments, the handle 110 can include one or more operating interfaces, such as steerable or rotatable adjustment knobs, levers, sliders, buttons (not shown) and other actuating mechanisms, which are operatively connected to different components of the delivery apparatus 102 and configured to produce axial movement of the delivery apparatus 102 in the proximal and distal directions, as well as to expand or contract the prosthetic valve 114 via various adjustment and activation mechanisms as will be further described below.

According to some embodiments, the handle further comprises one or more visual or auditory informative elements 112 configured to provide visual or auditory information and/or feedback to a user or operator of the delivery apparatus 102, such as a display 113*a*, LED lights 113*b*, speakers (not shown) and the like.

Figure 2A:
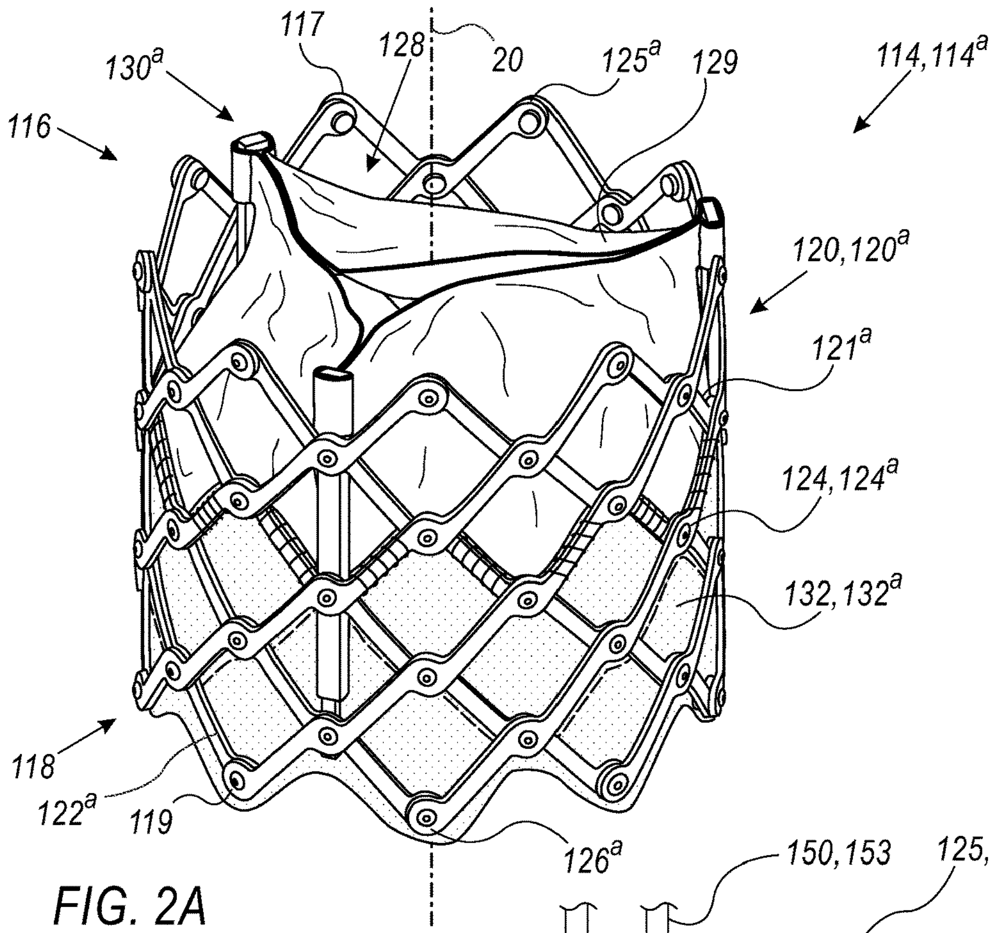
FIGS. 2A and 2B show in perspective view a prosthetic valve, according to some embodiments.
Figure 2B:
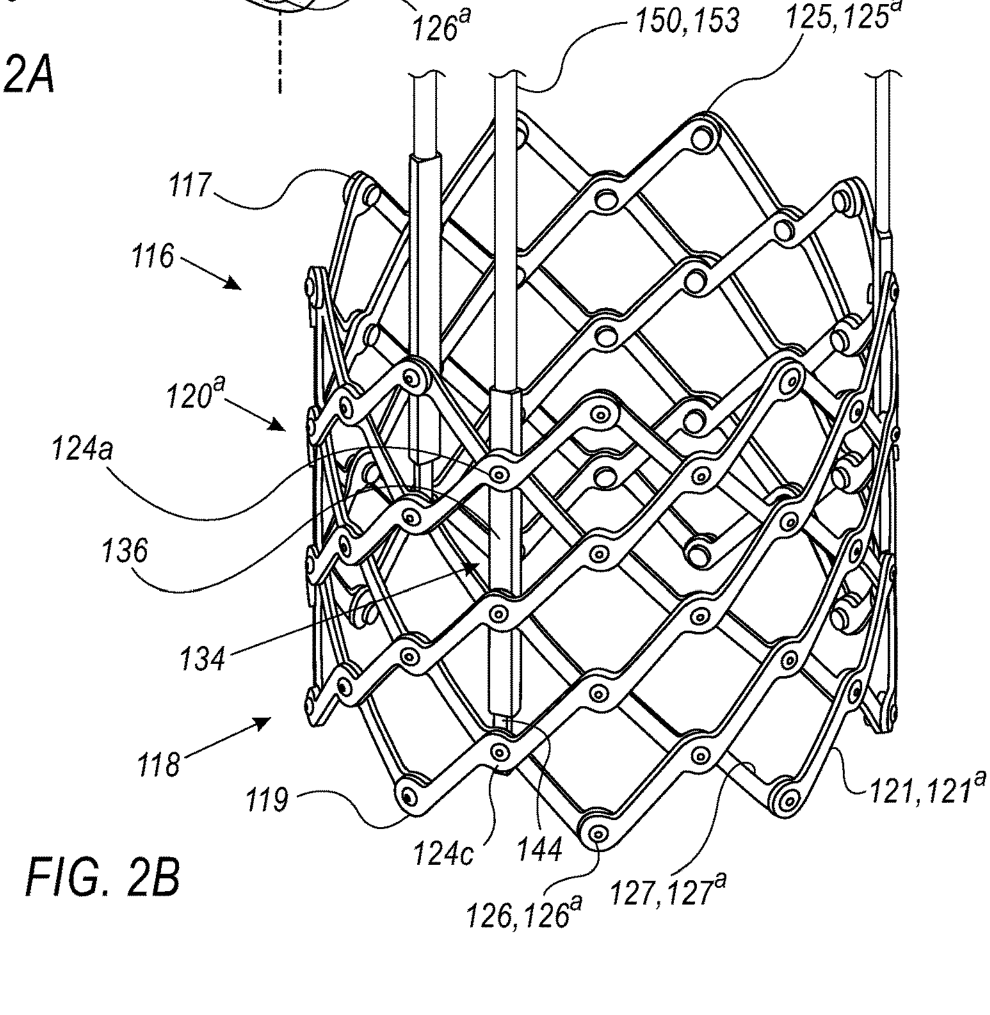

FIG. 2A shows an example of a mechanically expandable prosthetic valve 114[a] in an expanded state, according to some embodiments. FIG. 2B shows the prosthetic valve 114[a] of FIG. 2A with actuation assemblies 150 coupled to the expansion and locking assemblies 134. Soft components, such as leaflets or skirts, are omitted from view in FIG. 2A to expose the expansion and locking assemblies 134. The prosthetic valve 114 can comprise an inflow end portion 118 defining an inflow end 119, and an outflow end portion 116 defining an outflow end 117. In some instances, the outflow end 117 is the distal end of the prosthetic valve 114, and the inflow end 119 is the proximal end of the prosthetic valve 114. Alternatively, depending for example on the delivery approach of the valve, the outflow end can be the proximal end of the prosthetic valve, and the inflow end can be the distal end of the prosthetic valve.

The term "outflow", as used herein, refers to a region of the prosthetic valve through which the blood flows through and out of the valve 114, for example between the valve longitudinal axis 20 and the outflow end 117.

The term "inflow", as used herein, refers to a region of the prosthetic valve through which the blood flows into the valve 114, for example between inflow end 119 and the valve longitudinal axis 20.

The valve 114 comprises a frame 120 composed of interconnected struts 121, and may be made of various suitable materials, such as stainless steel, cobalt-chrome alloy (e.g. MP35N alloy), or nickel titanium alloy such as Nitinol. According to some embodiments, the struts 121, such as struts 121[a] shown in FIGS. 2A-B, are arranged in a lattice-type pattern. In the embodiment illustrated in FIGS. 2A-B, the struts 121[a] are positioned diagonally, or offset at an angle relative to, and radially offset from, the valve longitudinal axis 20, when the valve 114[a] is in an expanded position. It will be clear that the struts 121[a] can be offset by other angles than those shown in FIGS. 2A-B, such as being oriented substantially parallel to the valve longitudinal axis 20.

According to some embodiments, the struts 121 are pivotably coupled to each other. In the example embodiment shown in FIGS. 2A-B, the end portions of the struts 121 are forming apices 125 at the outflow end 117 and apices 126 at the inflow end 119. The struts 121 can be coupled to each other at additional junctions 124 formed between the outflow apices 125 and the inflow apices 126. The junctions 124 can be equally spaced apart from each other, and/or from the apices 125, 126 along the length of each strut 121. Frame 120, such as the frame 120[a] of a mechanically expandable valve, may comprise openings or apertures at the regions of apices 125, 126 and junctions 124 of the struts 121. Respective hinges can be included at locations where the apertures of struts 121 overlap each other, via fasteners, such as rivets or pins, which extend through the apertures. The hinges can allow the struts 121 to pivot relative to one another as the frame 120 is radially expanded or compressed.

In alternative embodiments, the struts are not coupled to each other via respective hinges, but are otherwise pivotable or bendable relative to each other, so as to permit frame expansion or compression. For example, the frame (e.g., frame 120[b] illustrated in FIG. 15) can be formed from a single piece of material, such as a metal tube, via various processes such as, but not limited to, laser cutting, electroforming, and/or physical vapor deposition, while retaining the ability to collapse/expand radially in the absence of hinges and like.

Strut portions 122 are defined between adjacent junctions 124, such as between two consecutive junctions 124 along the same strut 121, or between a junction 124 and an apex 125, 126. The frame 120 further comprises a plurality of cells 127, defined between intersecting strut portions 122. The shape of each cell 127, and the angle between each intersecting strut portion 122 defining its borders, vary during expansion or compression of the prosthetic valve 114.

The prosthetic valve 114 further comprises a leaflet assembly 128 having one or more leaflets 129, e.g., three leaflets, configured to regulate blood flow through the prosthetic valve 114 from the inflow end to the outflow end. While three leaflets 129 arranged to collapse in a tricuspid arrangement similar to the native aortic valve, are shown in the example embodiment illustrated in FIG. 2A, it will be clear that a prosthetic valve 114 can include any other number of leaflets 129, such as two leaflets configured to collapse in a bicuspid arrangement similar to the native mitral valve, or more than three leaflets, depending upon the particular application. The leaflets 129 are made of a flexible material, derived from biological materials (e.g., bovine pericardium or pericardium from other sources), bio-compatible synthetic materials, or other suitable materials as known in the art and described, for example, in U.S. Pat. Nos. 6,730,118, 6,767,362 and 6,908,481, which are incorporated by reference herein.

The leaflets 129 may be coupled to the frame 120 via commissures 130, either directly or attached to other structural elements connected to the frame 120 or embedded therein, such as commissure posts. Further details regarding prosthetic valves, including the manner in which leaflets may be mounted to their frames, are described in U.S. Pat. Nos. 7,393,360, 7,510,575, 7,993,394 and 8,252,202, and U.S. Patent Application No. 62/614,299, all of which are incorporated herein by reference.

According to some embodiments, the prosthetic valve 114 may further comprise at least one skirt or sealing member, such as the inner skirt 132 shown in the exemplary embodiment illustrated in FIG. 2A. The inner skirt 132 can be mounted on the inner surface of the frame 120, configured to function, for example, as a sealing member to prevent or decrease perivalvular leakage. The inner skirt 132 can further function as an anchoring region for the leaflets 129 to the frame 120, and/or function to protect the leaflets 129 against damage which may be caused by contact with the frame 120, for example during valve crimping or during working cycles of the prosthetic valve 114. Additionally, or alternatively, the prosthetic valve 114 can comprise an outer skirt 133 (see, for example, in FIG. 17B) mounted on the outer surface of the frame 120, configure to function, for example, as a sealing member retained between the frame 120 and the surrounding tissue of the native annulus against which the prosthetic valve 114 is mounted, thereby reducing risk of paravalvular leakage past the prosthetic valve 114. Any of the inner skirt 132 and/or outer skirt 133 can be made of various suitable biocompatible materials, such as, but not limited to, various synthetic materials (e.g., PET) or natural tissue (e.g. pericardial tissue).

According to some embodiments, a mechanically expandable valve 114$^a$ comprises a plurality of expansion and locking assemblies 134, configured to facilitate expansion of the valve 114$^a$, and in some instances, to lock the valve at an expanded state, preventing unintentional recompression thereof, as will be further elaborated below. Although FIGS. 2A-B illustrate three expansion and locking assemblies 134, mounted to, and equally spaced, around an inner surface of the frame 120$^a$, it should be clear that a different number of expansion and locking assemblies 134 may be utilized, that the expansion and locking assemblies 134 can be mounted to the frame 120$^a$ around its outer surface, and that the circumferential spacing between actuator assemblies 134 can be unequal.

FIGS. 3A, 3B and 3C show an exploded view in perspective, an assembled view in perspective, and a cross-sectional side view, respectively, of an expansion and locking assembly 134 according to some embodiments. The expansion and locking assembly 134 may include an outer member 136 defining an outer member lumen 139, secured to a component of the valve 114$^a$, such as the frame 120$^a$, at a first location, and an inner member 144 secured to a component of the valve 114$^a$, such as the frame 120$^a$, at a second location, axially spaced from the first location.

The inner member 144 extends between an inner member proximal end portion 145 and an inner member distal end portion 146. The inner member 144 comprises an inner member coupling extension 149 extending from its distal end portion 158, which may be formed as a pin extending radially outward from the distal end portion 146, configured to be received within respective openings or apertures of struts 121 intersecting at a non-apical junction 124 or an apex 125, 126. The inner member 144 may further comprise a linear rack having a plurality of ratcheting teeth 148 along at least a portion of its length. According to some embodiments, inner member 144 further comprises a plurality of ratcheting teeth 148 along a portion of its outer surface.

The outer member 136 comprises an outer member proximal end portion 137 defining a proximal opening of its lumen 139, and an outer member distal end portion 138 defining a distal opening of its lumen 139. The outer member 136 can further comprise an outer member coupling extension 140 extending from its proximal end portion 137, which may be formed as a pin extending radially outward from the external surface of the proximal end portion 137, configured to be received within respective openings or apertures of struts 121 intersecting at a non-apical junction 124 or an apex 125, 126.

The outer member 136 can further comprise a spring biased arm 142, attached to or extending from one sidewall of the outer member 136, and having a tooth or pawl 143 at its opposite end, biased inward toward the inner member 144 when disposed within the outer member lumen 139.

At least one of the inner or outer member 144 or 136, respectively, is axially movable relative to its counterpart. The expansion and locking assembly 134 in the illustrated embodiment, comprises a ratchet mechanism or a ratchet assembly, wherein the pawl 143 is configured to engage with the teeth 148 of the inner member 144. The spring-biased arm 142 can comprise an elongate body terminating in a pawl 143 in the form of a locking tooth, configured to engage the ratcheting teeth 148 of the inner member 144. The pawl 143 can have a shape that is complimentary to the shape of the teeth 148, such that the pawl 143 allows sliding movement of the inner member 144 in one direction relative to the spring-biased arm 142 (proximal direction in the illustrated embodiment) and resists sliding movement of the inner member 144 in the opposite direction (distal direction in the illustrated embodiment) when the pawl 143 is in engagement with one of the teeth 148.

Referring again to FIG. 3C, the arm 142 can be biased inwardly such that the pawl 143 is resiliently retained in a position engaging one of the teeth 148 of the inner member 144 (which can be referred to as the engaged position of the pawl 143). The spring-biased arm 142 can be formed of a flexible or resilient portion of the outer member 136 that extends over and contacts, via its pawl 143, an opposing side of the outer surface of the inner member 144. According to some embodiments, the spring-biased arm 142 can be in the form of a leaf spring that can be integrally formed with the outer member 136 or separately formed and subsequently connected to the outer member 136. The spring-biased arm 142 is configured to apply a biasing force against the outer surface of the inner member 144, so as to ensure that under normal operation, the pawl 143 stays engaged with the ratcheting teeth 148 of the inner member 144.

A mechanically expandable prosthetic valve 114$^a$ may be releasably attachable to at least one actuation assembly 150, and preferably a plurality of actuation assemblies 150, matching the number of expansion and locking assemblies 134. In some embodiments, the prosthetic valve 114 comprises three expansion and locking assemblies 134, and the delivery apparatus 102$^a$ comprises three actuation assemblies 150. The actuator 151 and the sleeve 153 can be movable longitudinally relative to each other in a telescoping manner to radially expand and contract the frame 120$^a$, as further described in U.S. Publication Nos. 2018/0153689, 2018/0153689 and 2018/0325665, which are incorporated herein by reference. The actuators 151 can be, for example, wires, cables, rods, or tubes. The sleeves 153 can be, for example, tubes or sheaths having sufficient rigidity such that they can apply a distally directed force to the frame 120$^a$ or the outer member 136 without bending or buckling.

The inner member proximal end portion 145 further comprises an inner member threaded bore 147, configured to receive and threadedly engage with a threaded portion of a distal end portion 152 (shown for example in FIG. 4C) of a corresponding actuator 152. FIG. 2B shows a view in perspective of a valve 114$^a$ in an expanded state, having its expansion and locking assemblies 134 connected to actuators 151 (hidden from view within the sleeves 153) of a delivery apparatus 102$^a$. When actuators 151 are threaded into the inner members 144, axial movement of the actuators 151 causes axial movement of the inner members 144 in the same direction.

Figure 4A:
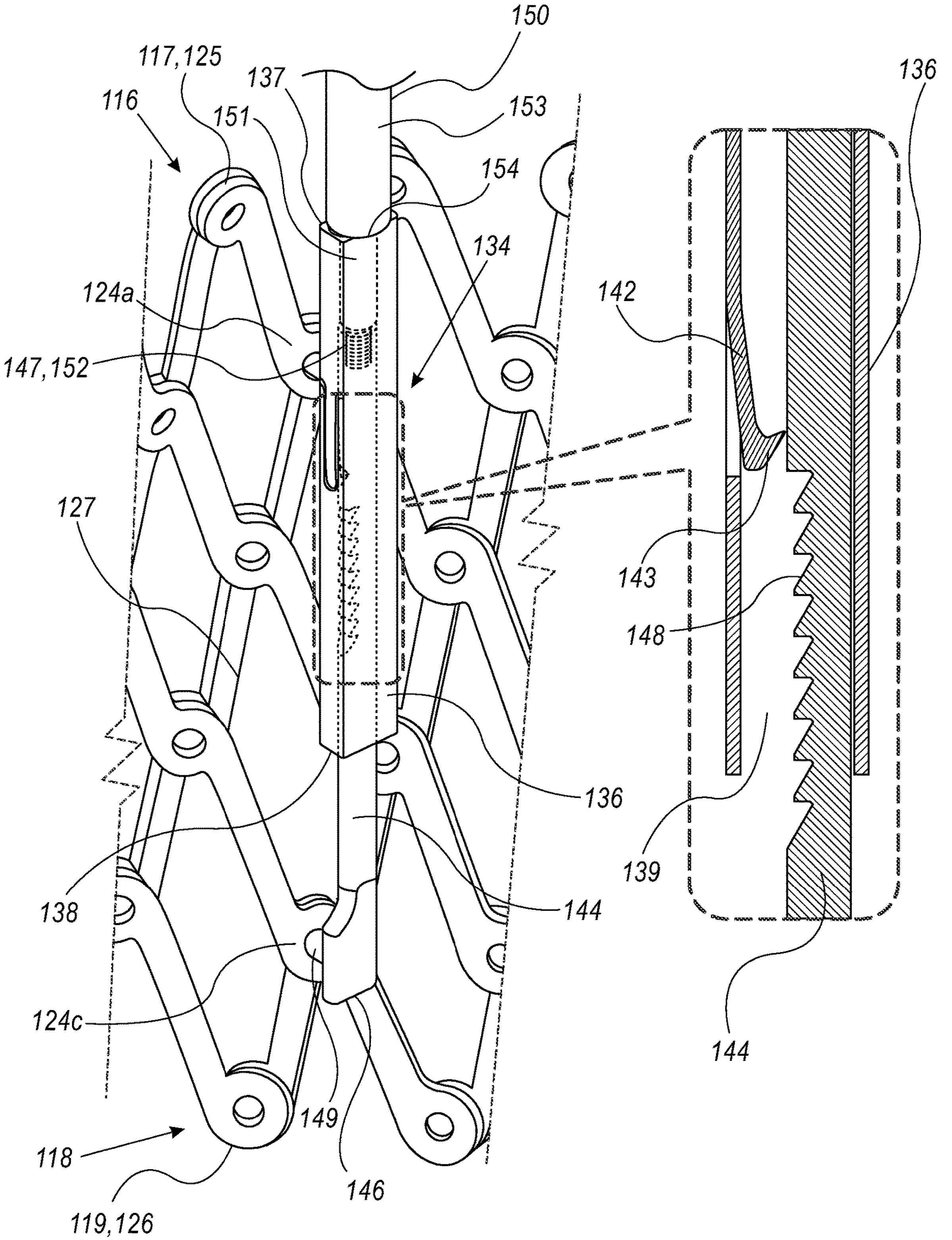
FIGS. 4A-4C show an actuator assembly of the type shown in FIG. 3B in different operational states thereof.
Figure 4B:
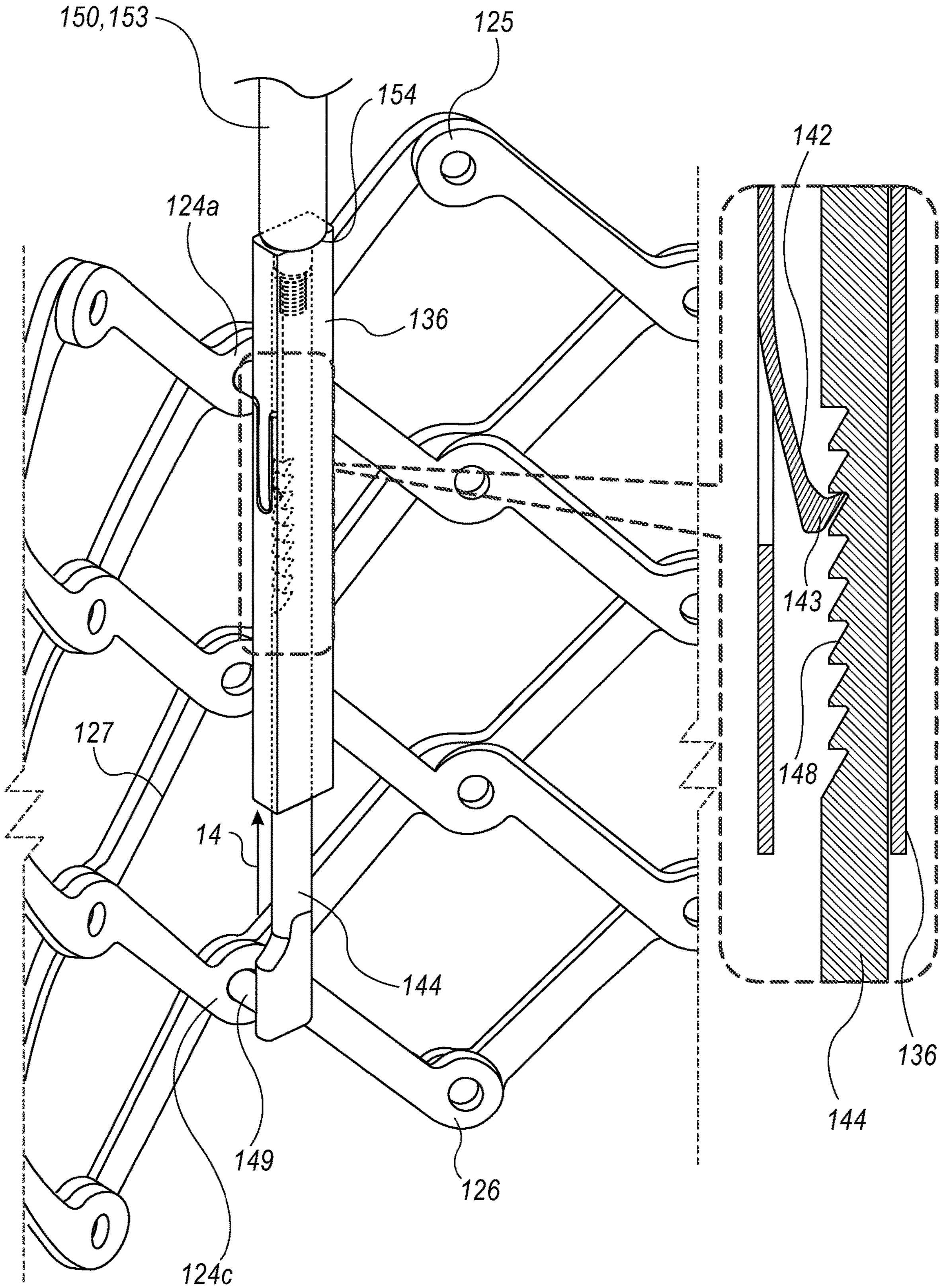
Figure 4C:
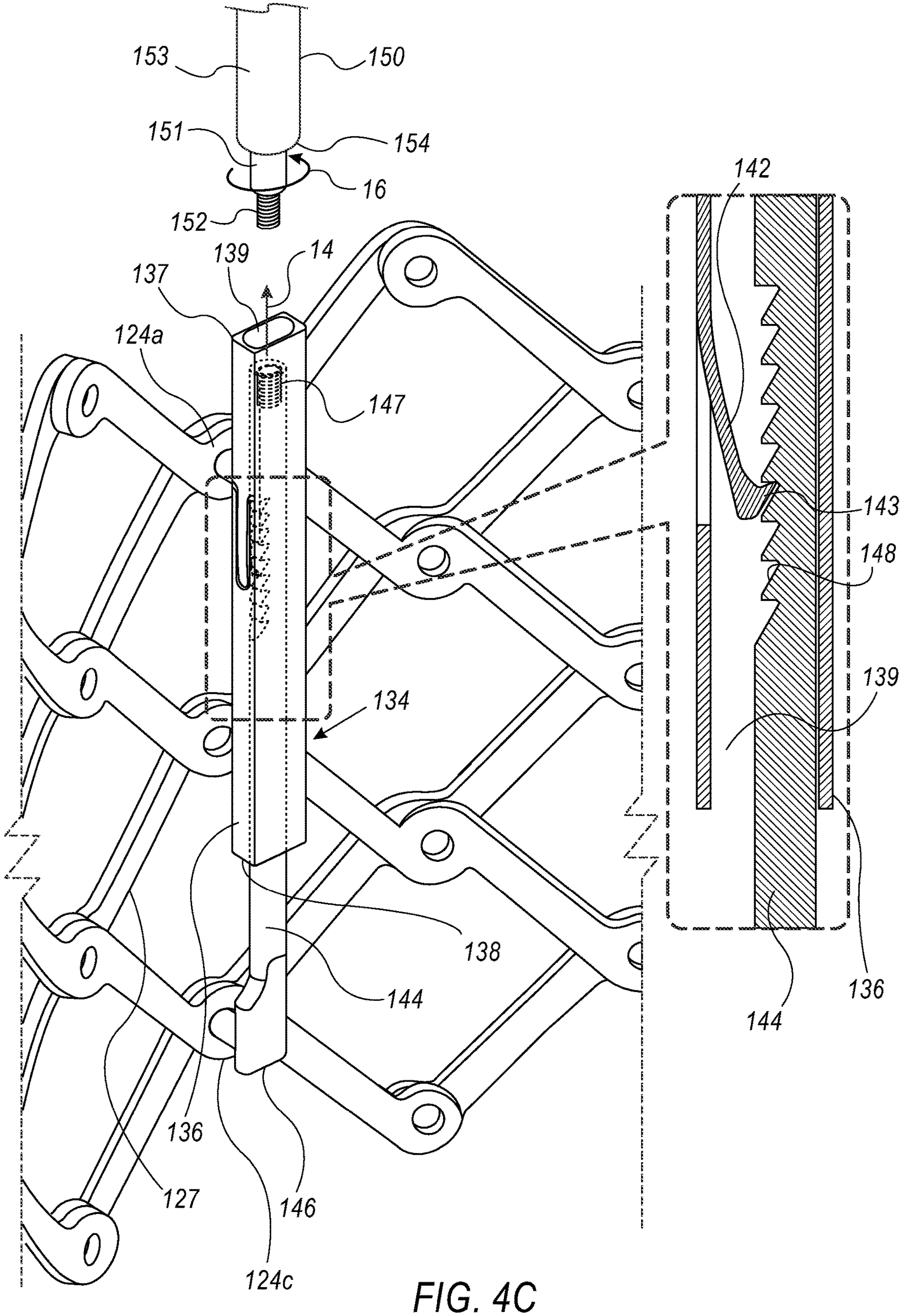

According to some embodiments, the actuation assemblies 150 are configured to releasably couple to the prosthetic valve 114$^a$, and to move the prosthetic valve 114$^a$ between the radially compressed and the radially expanded configurations. FIGS. 4A-4C illustrate a non-binding configuration representing actuation of the expansion and locking assemblies 134 via the actuation assemblies 150 to expand the prosthetic valve 114$^a$ from a radially compressed configuration to a radially expanded configuration.

FIG. 4A shows an expansion and locking assembly 134, having an outer member 136, secured to the frame 120$^a$ at a first location, and an inner member 144 secured to the frame 120$^a$ at a second location. According to some embodiments, the first location can be positioned at or adjacent to the outflow end portion 116, and the second location can be positioned at or adjacent to the inflow end portion 118. In the illustrated embodiment, the outer member 136 is secured to a proximal-most non-apical junction 124*a* which is distal to the outflow apices 125 or the outflow end 117, via outer member coupling extension 140, and the inner member 144 is secured to a distal-most non-apical junction 124*c* which is proximal to the inflow apices 126 or the inflow end 119, via inner member coupling extension 149. A proximal portion of the inner member 144 extends, through the distal opening of the outer member distal end 138, into the outer member lumen 139.

It is to be understood that while the illustrated embodiments are for an expansion and locking assembly 134 secured to a proximal-most non-apical junction 124*a* serving as the first location, and to a distal-most non-apical junction 124*c* serving as the second location, in other implementations, the expansion and locking assembly 134 can be secured to other junctions, including apices of the valve. For example, the expansion and locking assembly can be secured to an outflow apex 125 via the outer member coupling extension 140, serving as the first location, and to an opposing inflow apex 126 along the same column of cells, via the inner member coupling extension 149, serving as the second location.

The expansion and locking assembly 134 is shown in FIG. 4A in a radially compressed state of the valve 114$^a$, wherein the outflow and inflow apices 125 and 126, respectively, are relatively distanced apart from each other along the axial direction, and the inner member proximal end portion 145 is positioned distal to the outer member proximal end portion 137.

As further shown in FIG. 4A, the actuator distal end portion 152 is threadedly engaged with the inner member threaded bore 147. According to some embodiments, as shown in FIGS. 4A-4C, the actuator distal end portion 152 includes external threads, configured to engage with internal threads of the inner member threaded bore 147. According to alternative embodiments, an inner member may include a proximal extension provided with external threads, configured to be received in and engage with internal threads of a distal bore formed within the actuator (embodiments not shown).

The sleeve 153 surrounds the actuator 151 and may be connected to the handle 110$^a$ of a delivery apparatus 102$^a$. The sleeve 153 and the outer member 136 are sized such that the distal lip 154 of the sleeve 153 can abut or engage the outer member proximal end 137, such that the outer member 136 is prevented from moving proximally beyond the sleeve 153.

In order to radially expand the frame 120$^a$, and therefore the valve 114$^a$, the sleeve 153 can be held firmly against the outer member 136. The actuator 151 can then be pulled in a proximally oriented direction 14, as shown in FIG. 4B. Because the sleeve 153 is being held against the outer member 136, which is connected to the frame 120$^a$ at the first location, the outflow end 117 of the frame 120$^a$ is prevented from moving relative to the sleeve 153. As such, movement of the actuator 151 in a proximally oriented direction 14 can cause movement of the inner member 144 in the same direction, thereby causing the frame 120$^a$ to foreshorten axially and expand radially.

More specifically, as shown for example in FIG. 4B, the inner member coupling extension 149 extends through apertures in two struts 121$^a$ interconnected at a distal non-apical junction 124*c*, while the outer member coupling extension 140 extends through aperture in two struts 121$^a$ interconnected at a proximal non-apical junction 124*a*. As such, when the inner member 144 is moved axially, for example in a proximally oriented direction 14, within the outer member lumen 139, the inner member coupling extension 149 moves along with the inner member 144, thereby causing the portion to which the inner member coupling extension 149 is attached to move axially as well, which in turn causes the frame 120$^a$ to foreshorten axially and expand radially.

The struts 121$^a$ to which the inner member coupling extension 149 is connected are free to pivot relative to the coupling extension 149 and to one another as the frame 120$^a$ is expanded or compressed. In this manner, the inner member coupling extension 149 serves as a fastener that forms a pivotable connection between those struts 121$^a$. Similarly, struts 121$^a$ to which the outer member coupling extension 140 is connected are also free to pivot relative to the coupling extension 140 and to one another as the frame 120$^a$ is expanded or compressed. In this manner, the outer coupling fastening extension 140 also serves as a fastener that forms a pivotable connection between those struts 121$^a$.

As mentioned above, when the pawl 143 of the spring biased arm 142 is engaged with the ratcheting teeth 148, the inner member 144 can move in one axial direction, such as the proximally oriented direction 14, but cannot move in the opposite axial direction. This ensures that while the pawl 143 is engaged with the ratcheting teeth 148, the frame 120$^a$ can radially expand but cannot be radially compressed. Thus, after the prosthetic valve 114$^a$ is implanted in the patient, the frame 120$^a$ can be expanded to a desired diameter by pulling the actuator 151. In this manner, the actuation mechanism also serves as a locking mechanism of the prosthetic valve 114$^a$.

Once the desired diameter of the prosthetic valve 114$^a$ is reached, the actuator 151 may be rotated, for example in rotation direction 16, to unscrew the actuator 151 from the inner member 144, as shown in FIG. 4C. This rotation serves to disengage the distal threaded portion 152 of the actuator 151 from the inner member threaded bore 147, enabling the actuation assemblies 150 to be pulled away, and retracted, together with the delivery apparatus 102$^a$, from the patient's body, leaving the prosthetic valve 114$^a$ implanted in the patient. The patient's native anatomy, such as the native aortic annulus in the case of transcatheter aortic valve implantation, may exert radial forces against the prosthetic valve 114$^a$ that would strive to compress it. However, the engagement between the pawl 143 of the spring biased arm 142 and the ratcheting teeth 148 of the inner member 144 prevents such forces from compressing the frame 120$^a$, thereby ensuring that the frame 120$^a$ remains locked in the desired radially expanded state.

Thus, the prosthetic valve 114$^a$ is radially expandable from the radially compressed state shown in FIG. 4A to the radially expanded state shown in FIG. 4B upon actuating the expansion and locking assemblies 134, wherein such actuation includes approximating the second locations to the first locations of the valve 114[a]. The prosthetic valve 114[a] is further releasable from the delivery apparatus 102[a] by decoupling each of the actuation assemblies 150 from each of the corresponding expansion and locking assemblies 134 that were attached thereto.

While the frame 120[a] is shown above to expand radially outward by axially moving the inner member 144 in a proximally oriented direction 14, relative to the outer member 136, it will be understood that similar frame expansion may be achieved by axially pushing an outer member 136 in a distally oriented direction, relative to an inner member 144.

While a threaded engagement is illustrated and described in the above embodiments, serving as an optional reversible-attachment mechanism between the actuation assemblies 150 and the inner members 144, it is to be understood that in alternative implementations, other reversible attachment mechanisms may be utilized, configured to enable the inner member 144 to be pulled or pushed by the actuation assemblies 150, while enabling disconnection there-between in any suitable manner, so as to allow retraction of the delivery apparatus from the patient's body at the end of the implantation procedure. For example, the distal end portion of the actuator can include a magnet, and the inner member bore can include a correspondingly magnetic material into which the distal end portion of the actuator can extend.

According to some embodiments, the handle 110 can comprise control mechanisms which may include steerable or rotatable knobs, levers, buttons and such, which are manually controllable by an operator to produce axial and/or rotatable movement of different components of the delivery apparatus 102. For example, the handle 110[a] may comprise one or more manual control knobs, such as a manually rotatable control knob that is effective to pull the actuator 151 when rotated by the operator.

According to other embodiments, control mechanisms in handle 110 and/or other components of the delivery apparatus 102 can be electrically, pneumatically and/or hydraulically controlled. According to some embodiments, the handle 110 can house one or more electric motors which can be actuated by an operator, such as by pressing a button or switch on the handle 110, to produce movement of components of the delivery apparatus 102. For example, the handle 110[a] may include one or more motors operable to produce linear movement of components of the actuation assemblies 150, and/or one or more motors operable to produce rotational movement of the actuators 151 to disconnect the actuator distal end portion 152 from the actuation inner member threaded bore 147. According to some embodiments, one or more manual or electric control mechanism is configured to produce simultaneous linear and/or rotational movement of all of the actuators 151.

While a specific actuation mechanism is described above, utilizing a ratcheting mechanism between the inner and the outer members of the expansion and locking assemblies 134, other mechanisms may be employed to promote relative movement between inner and outer members of expansion and locking assemblies, for example via threaded or other engagement mechanisms. Further details regarding the structure and operation of mechanically expandable valves and delivery system thereof are described in U.S. Pat. No. 9,827,093, U.S. Patent Application Publication Nos. 2019/0060057, 2018/0153689 and 2018/0344456, and U.S. Patent Application Nos. 62/870,372 and 62/776,348, all of which are incorporated herein by reference.

Prior to implantation, the prosthetic valve 114 can be crimped onto the delivery apparatus 102. In some embodiments, this step can include covering at least a portion of the radially compressed valve 114 by the outer shaft 104 or by an external capsule (not shown). Once delivered to the site of implantation, such as a native annulus, the valve 114 can be radially expanded within the annulus, for example, by actuating the expansion and locking assemblies 134 described herein above in the case of mechanically expandable valves 114[a]. However, during such implantation procedures, it may become desirable to re-compress the prosthetic valve 114[a] in situ in order to reposition it. Valve recompression may be achievable, for example, if the mechanically expandable valve 114[a] has not yet reached a locked state, for example by providing a sufficient smooth length (i.e., devoid of ratcheting teeth 148) along the inner member 144, so as to allow axial movement along a specific distance prior to pawl 143 engagement with the teeth 148. Alternatively or additionally, the delivery assembly 100[a] can further include release members (not shown), configured to release the pawl 143 from the teeth 148 to allow reversible movement that will enable valve compression.

According to some embodiments, the handle 110 includes a control unit 111[a] configured to receive measurement signals from the at least one communication channel 160, and produce a measure indicative of valve expansion diameter in real time. Control unit 111[a] can include a central processing unit (CPU), a microprocessor, a microcomputer, a programmable logic controller, an application-specific integrated circuit (ASIC) and/or a field-programmable gate array (FPGA), without limitation. The control unit 111[a] may be provided as an electrical or an electro-optical circuitry.

According to some embodiments, the delivery apparatus 102 further comprises a flex sensing assembly 156 in communication with control unit 111[a]. Responsive to an output of flex sensing assembly 156, control unit 111[a] is configured to measure angular displacement of at least one strut 121 of a prosthetic valve 114. More specifically, the flex sensing assembly 156 comprises at least one flex sensor coupled to at least one strut 121, from which an angle, such as an opening angle of the valve 114, can be derived. The opening angle may be correlated to the valve expansion diameter, so as to provide a real-time indication of the valve diameter.

The terms coupled, engaged and attached, as used herein, are interchangeable. Similarly, the term decoupled, disengaged and detached, as used herein, are interchangeable.

Figure 5A:
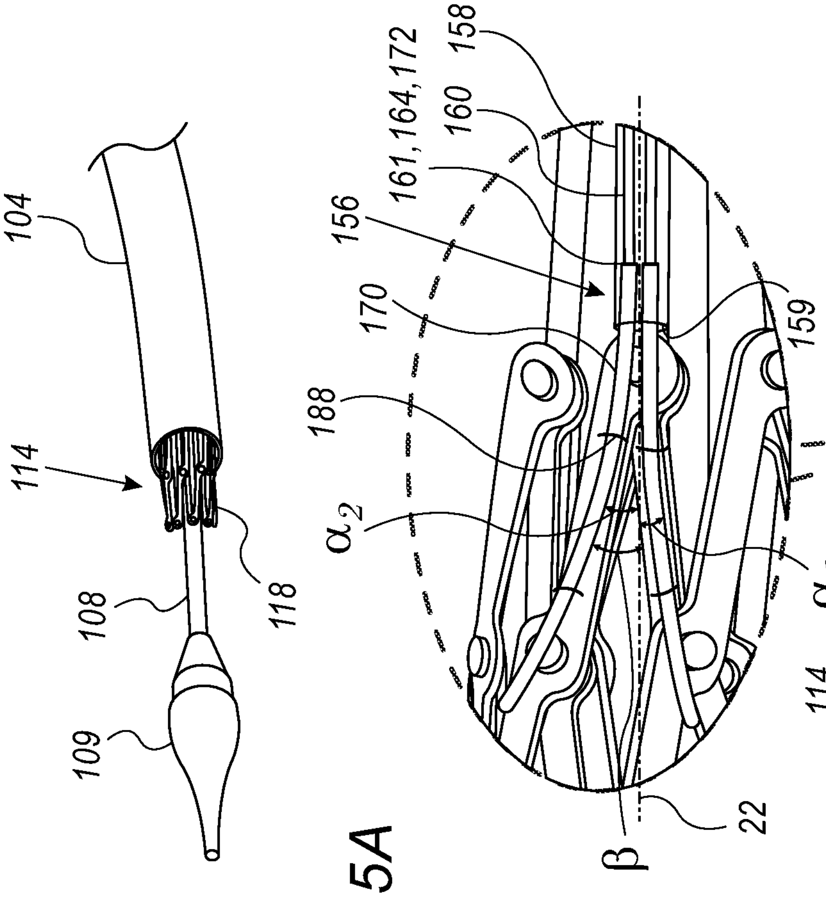
FIGS. 5A-5C show different stages of utilizing a delivery assembly equipped with a flex sensing assembly, according to some embodiments.
Figure 5B:
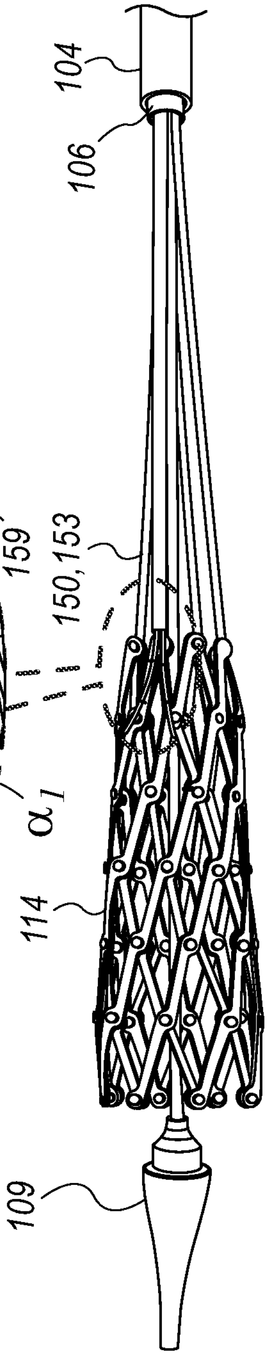
Figure 5C:
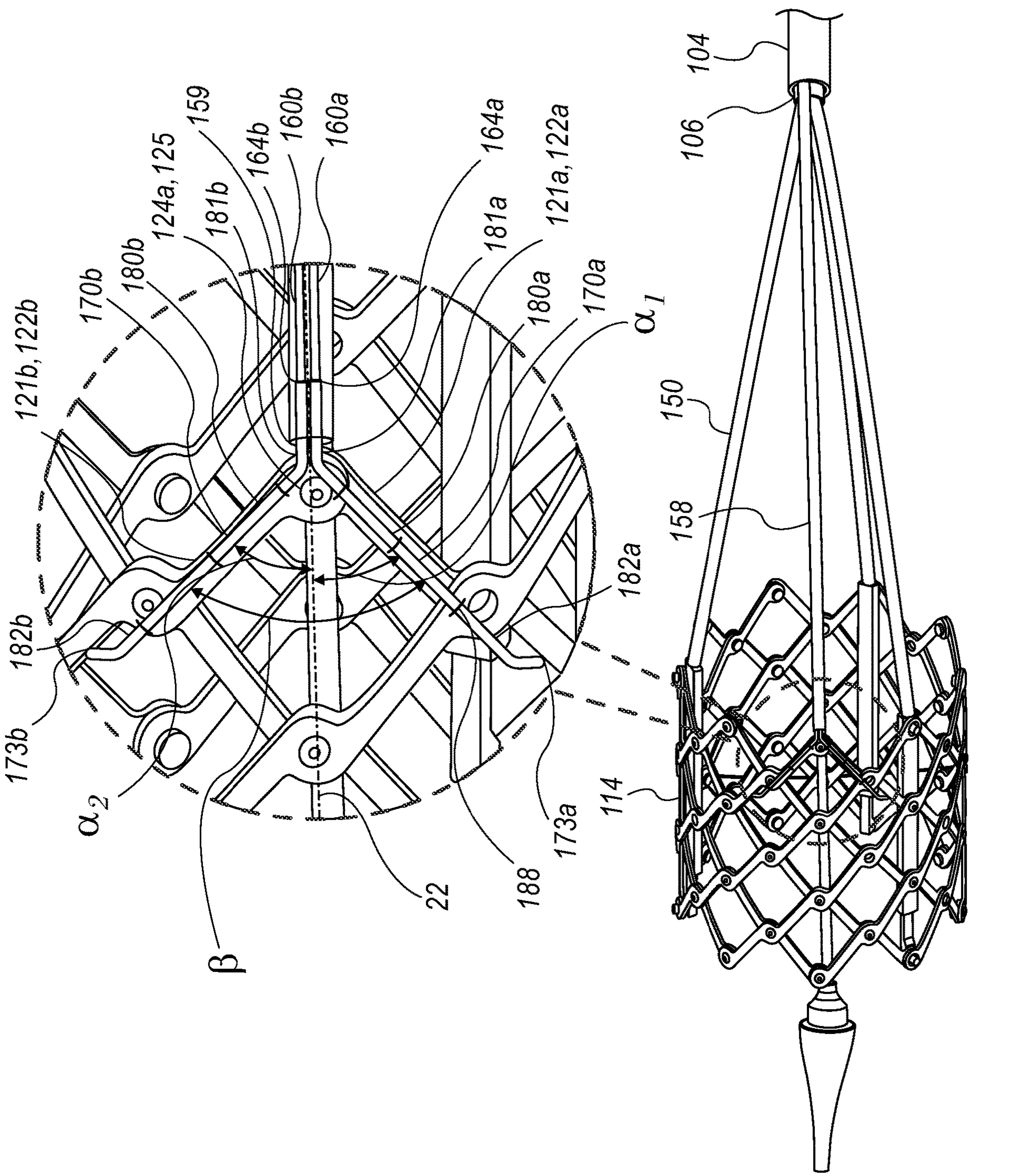

Reference is now made to FIGS. 5A-5C, showing different optional stages of utilizing a delivery assembly 100 equipped with a flex sensing assembly 156. The leaflet assembly 128 and skirt 132 are omitted from FIGS. 5A-14E for purposes of clarity. FIG. 5A shows an enlarged view of a distal portion of the delivery assembly 100, carrying a prosthetic valve 114 retained in a compressed or crimped state within a distal portion of the outer shaft 104 during delivery to the implantation site. As described above, the distal portion of the outer shaft 104 can serve as a delivery capsule that covers the crimped prosthetic valve 114. Upon reaching the desired site of implantation, the outer shaft 104 can be retracted to expose the prosthetic valve 114. FIG. 5A shows partial retraction of the outer shaft 104, exposing a distal portion of the valve 114, such as the inflow end portion 118.

FIG. 5B shows the prosthetic valve 114 exposed (i.e., no longer covered by the outer shaft 104). Certain prosthetic valves 114, such as certain mechanically expandable valves 114[a] as described above in conjunction with FIGS. 1-4C, may be provided with internal resiliency promoting partial expansion thereof when extended out of a capsule or outer shaft 104. FIG. 5C shows the valve 114 further expanded, for example to a partially-expanded or a fully expanded diameter thereof.

According to some embodiments, the flex sensing assembly 156 comprises at least one flex sensor 170. The flex sensor 170 is defined between a flex sensor proximal end 172 and a flex sensor distal end 173. An output of at least one flex sensor 170 is configured to represent the flex of at least one flex sensor 170, including an electrical and/or optical output. Particularly, according to some embodiments, and as known to those skilled in the art, at least one flex sensor 170 can be electrical, such that the electrical resistance thereof varies responsive to the flex of at least one flex sensor 170. For example, control unit 111[a] can generate a current that flows through at least one flex sensor 170, the voltage at the output of at least one flex sensor 170 thus representing the flex thereof. Alternatively, control unit 111[a] can apply a voltage across at least one flex sensor 170, the current at the output of at least one flex sensor 170 thus representing the flex thereof. Additionally, or alternately, at least one flex sensor 170 can be optical, such that the amount of light transmitted between proximal end 172 and distal end 173 varies responsive to the flex of at least one flex sensor 170. For example, a light source can be provided at distal end 173, the amount of light at the output of at least one flex sensor 170 (e.g. at proximal end 172) thus representing the flex thereof.

The flex sensing assembly 156 may further comprise at least one communication channel 160, extending distally from the handle 110 to a communication channel distal end 161, and coupled to control unit 111[a]. The term "communication channel", as used herein, means a physical path allowing communication therethrough. According to some embodiments, the communication channel is configured to allow: electrical communication via a conductive material, such as a wire; and/or optical communication, e.g. via an optical fiber. The communication channel distal end 161 may be coupled to a respective flex sensor proximal end 172 at an interface 164. Each communication channel 160 may extend into the handle 110. When coupled to the flex sensor 170 at interface 164, the communication channel 160 is configured to conduct the signals (either an electric and/or an optic signals) from the output of flex sensor 170 towards control unit 111[a]. In some instances, the communication channel 160 may be integrally formed with the flex sensor 170. For example, the communication channel 160 may be formed as a continuous extension of the flex sensor 170. Alternatively, the communication channel 160 and the flex sensor 170 may be provided as separate components attached to each other at interface 164. According to some embodiments, the communication channel 160 is detachably coupled to the flex sensor 170.

According to some embodiments, the flex sensing assembly 156 further comprises a sensor shaft 158, extending distally from the handle 110 to a sensor shaft distal end 159, wherein at least a portion of the communication channel 160 extends through a lumen of the sensor shaft 158. According to some embodiments, the communication channel 160 is axially movable within the lumen of the sensor shaft 158.

In some configurations, the interface 164 may be positioned within the lumen of the sensor shaft 158, such that a proximal portion of the flex sensor 170 is disposed within the sensor shaft 158, while the remainder of the flex sensor 170 extends out of the sensor shaft 158. In some configurations, the interface 164 may be positioned distal to the sensor shaft distal end 159, such that a distal portion of the communication channel 160, and the entire length of the flex sensor 170, extend out of the sensor shaft 158.

According to some embodiments, the at least one flex sensor 170 is coupled to at least one strut 121, for example to a strut portion 122, to measure angular movement and/or angular orientation thereof during valve expansion or compression. The angular movement and/or angular orientation of the at least one strut 121, and more specifically, the at least one strut portion 122, may be measured relative to an axis, such as the valve longitudinal axis 20 or the sensor shaft axis 22, and/or relative to another structural component of the valve 114, such as another intersecting strut 121 or strut portion 122, an actuator outer member 136, a commissure post (e.g., an outer member 136 or any other commissure post), a vertical portion of the frame, and the like.

The exemplary embodiment shown in FIGS. 5B-5C illustrates a flex sensing assembly 156 comprising two flex sensors 170, coupled to two intersecting struts 121, and more specifically, to two intersecting strut portions 122. While this configuration may be advantageous for some applications, it will be understood that any other number of flex sensors 170 is contemplated, including a single flex sensor or more than two flex sensors.

According to some embodiments, as shown, a first flex sensor 170*a* and a second flex sensor 170*b* are coupled to a first strut portion 122*a* of a first strut 121*a* and a second strut portion 122*b* of a second strut 121*b*, respectively, intersecting at a junction 124. In some applications, the intersection junction may be an outflow apex 125.

According to some embodiments, a first communication channel 160*a* is coupled to the first flex sensor 170*a*, and a second communication channel 160*b* is coupled to the second flex sensor 170*b*. According to some embodiments, the plurality of communication channels 160*a* may extend through the lumen of a single sensor shaft 158. In alternative embodiments, the flex sensing assembly 156 comprises a plurality of sensor shafts 158, such that each communication channel 160 may extend through the lumen of a respective, different, sensor shaft 158.

A sensor shaft axis 22 is defined as a longitudinal axis orthogonal to the plane of the opening at the sensor shaft distal end 159. As shown in FIG. 5C, when the valve 114 expands, a first angle $\alpha_1$ may be defined between the first strut portion 122*a* and the sensor shaft axis 22, and a second first angle $\alpha_2$ may be defined between the second strut portion 122*b* and the sensor shaft axis 22, such that the sum of the first and second angles $\alpha_1$ and $\alpha_2$, respectively, results in an opening angle $\beta$ defined between the two intersecting struts 121*a* and 121*b* at the intersection junction 124.

According to some embodiments, each flex sensor 170 comprises a bending portion 180 coupled to the respective strut 121 (e.g., to the respective strut portion 122), and a non-bending portion 181 extending proximal to the intersection junction 124, wherein each bending portion 180 may bend, along with the strut 121 (e.g., along the strut portion 122), relative to the non-bending portion 181.

According to some embodiments, the first non-bending portion 181*a* and the second non-bending portion 181*b* are aligned with each other, such that they may be substantially disposed in parallel with each other.

One element is termed to be substantially parallel with another element if both elements are angled at an angle of no more than 5 degrees relative to each other.

Typically, the sensor shaft axis 22 is collinear with the longitudinal axes of the first non-bending portions 181. According to some embodiments, the first angle $\alpha_1$ may be defined between a longitudinal axis of the first bending portion 180*a* and a longitudinal axis of the first non-bending portion 181*a*, and the second first angle $\alpha_2$ may be defined between a longitudinal axis of the second bending portion 180*b* and a longitudinal axis of the second non-bending portion 181*b*, such that the sum of the first and second angles $\alpha_1$ and $\alpha_2$, respectively, results in an opening angle β defined between the longitudinal axis of the first bending portion 180*a* and the longitudinal axis of the second bending portion 180.

According to some embodiments, the sensor shaft distal end 159 is positioned adjacent to the junction 124, and the interface 164 is disposed within the lumen of the sensor shaft 158, such that upon valve expansion, the sensor shaft distal end 159 acts as a fulcrum for the bending portions 180*a*, 180*b*, defining the non-bending portions 181*a*, 181*b* between the interfaces 164*a*, 164*b* and the sensor shaft distal ends 159*a*, 159*b*, respectively.

According to some embodiments, each flex sensor 170 is coupled to a respective strut 121 via at least one coupling member 188. The at least one coupling member 188 can be in the form of a suture, a band, a sleeve, a snap-fit member, glue, and the like. According to some embodiments, at least one coupling member 188 is a non-affixing coupling member, configured to couple the flex sensor 170 to the strut 121 in a manner that prevents spontaneous displacement of the flex sensor 170, yet allows axial movement or sliding of the flex sensor 170 over and relative to the strut 121, for example during valve expansion or compression, or during application of a pulling force to retract the flex sensor 170 from the valve 114. According to some embodiments, at least one coupling member 188 is an affixing coupling member, configured to affix the flex sensor 170 to the strut 121, for example by gluing or welding.

According to some embodiments, the at least one flex sensor 170 is coupled to a respective strut 121 via a plurality of coupling members 188. According to some embodiments, the at least one flex sensor 170 is coupled to a respective strut 121 via more than one type of a coupling member 188. According to some embodiments, the at least one flex sensor 170 is coupled to a respective strut 121 via a plurality of coupling members 188 comprising at least one affixing coupling member and at least one non-affixing coupling member. For example, a flex sensor 170 can be affixed to the strut 121 by being glued, welded, riveted and the like, at a proximal point of attachment—such as in the vicinity of the intersection junction 124, and one or more non-affixing coupling members, such as suture loops, tubes, sleeves, bands, rails and the like, distal to the affixing coupling member. In such an example, the flex sensor 170 may be affixed to the strut 121 at the affixation point, while the remained of the flex sensor 170 may slide over the strut 121 as the opening angle changes, so as to prevent the flex sensor 170 from being over-tensioned during valve expansion.

According to some embodiments, the at least one flex sensor 170 is coupled to a respective strut 121 via one or more coupling members 188 that include only non-affixing coupling members. For example, the flex sensor 170 may be coupled to the strut 121 via a plurality of spaced apart suture loops or bands, tightly looped around the flex sensor 170 and the strut 121 so as to prevent spontaneous movement therebetween. In such an example, the flex sensor 170 may slide within the coupling members 188 relative to the strut 121, during valve expansion (or contraction) or application of a retraction force, which exceed the frictional forces applied by the coupling members 188 on the flex sensor 170.

According to some embodiments, the at least one flex sensor 170 is coupled to a respective strut 121 via more than one type of non-affixing coupling members. According to some embodiments, a flex sensor 170 is coupled to the strut 121 via at least one first type of a non-affixing coupling member, and at least one second type of non-affixing coupling member, distal to the first type of non-affixing coupling member, wherein the first type of non-affixing member is configured to release the flex sensor 170 from, or allow movement of the flex sensor 170 relative to, the strut 121, upon application of a retraction force higher than that required to allow such relative movement within or along the second type of non-affixing coupling members.

For example, a flex sensor 170 can be coupled to the strut 121 by a first type of a non-affixing coupling member in the form of a releasable snap-fit member, at a proximal point of attachment—such as in the vicinity of the intersection junction 124, and one or more second type of non-affixing coupling members, such as suture loops, tubes, sleeves, bands, rails and the like, distal to the first type of a non-affixing coupling member. In such an example, the flex sensor 170 may be immovable relative to the strut 121 at the snap-fit coupling member, while the remainder of the flex sensor 170 may slide over the strut 121 as the opening angle changes. However, once expansion is complete and removal of the flex sensor 170 from the valve 114 is desired, the handle 110 can be further maneuvered to retract the sensor 170 at a higher force magnitude than the force applied during valve expansion, wherein the pull force is sufficient to detach the snap-fit member 188 so as to allow the flex sensor 170 to be released from the strut 121.

According to some embodiments, the prosthetic valve 114 is further releasable from the delivery apparatus 102 by decoupling at least a portion of each flex sensor assembly 156 from the prosthetic valve 114. In some applications, decoupling at least a portion of each flex sensor assembly 156 refers to at least the communication channels 160 being retractable from the prosthetic valve, either with the flex sensors 170 remaining coupled thereto, or without the flex sensors 170 which may be decoupled therefrom.

According to some embodiments, the valve 114 is releasable from the delivery apparatus 102 by decoupling each communication channel 160 from the corresponding flex sensor 170 it was attached to, while the flex sensors 170 may remain attached to the respective struts 121. According to some embodiments, the valve 114 is further releasable from the delivery apparatus 102 by decoupling each flex sensor 170 from the strut 121 it was coupled to, for example, by pulling the flex sensors 170 at a force sufficient to overcome friction forces applied thereto by the respective coupling members 188.

The control unit 111[a] can be configured to continuously calculate the diameter of the prosthetic valve 114, responsive to the output of at least one flex sensor 170. According to some embodiments, the control unit 111[a] is operatively couple to a visual interface 112, such as a display 113*a* and/or LED lights 113*b*. The display 113*a* may comprise a digital screen, which may present numerical values indicative of the valve current diameter, as well as other icons, textual messages or graphical symbols. Additionally or alternatively, a visual interface 112 may comprise LED lights 113*b*, lamps or other visual elements, configured to provide the user with a visual indication of the current valve diameter. According to some embodiments, the control unit 111[a] is configured to display the diameter of the prosthetic valve 114 on the visual interface 112 in real-time, as the prosthetic valve 114 is expanded and/or compressed during an implantation procedure.

According to some embodiments, the control unit 111[a] further comprises a memory. According to some embodiments, selected data, such as raw signal data or calculated data, may be stored in the memory. According to some embodiments, the control unit 111[a] is configured to log data during the implantation procedure in the memory. According to some embodiments, the control unit 111[a] is configured to transmit to a remote device, logged data from the memory, and/or real-time data.

According to some embodiments, the flex sensor 170 may be operatively coupled, for example via communication channel 160, to the control unit 111[a], and configured such that control unit 111[a] can read the output of flex sensor 170. Responsive to the output of flex sensor 170, control unit 111[a] derives measures such as magnitude or degree of flex. As described above, control unit 111[a] performs and/or receives electrical and/or optical measurements from flex sensor 170. These measurements can be used as a surrogate index in order to estimate valve expansion diameter or changes in diameter.

According to some embodiments, the control unit 111[a] is configured to provide an alert to an operator (e.g., a clinician) in the event of valve over-expansion within a native annulus. For example, an opening angle $\beta$ can be derived from the extent of the bend measured by the at least one flex sensor 170. According to some embodiments, the opening angle $\beta$ is derived from flex measurements from at least two flex sensor 170, optionally coupled to two intersecting struts 121. The opening angle $\beta$ can be correlated with a valve expansion diameter, and compared against one or more threshold values. Depending on the result (e.g., if a relevant threshold is exceeded), a state of valve over-expansion can be determined. The alert may be an audible alert, a visual alert, a tactile alert, or any combination thereof.

The terms bend and flex, as used herein, are interchangeable.

According to some embodiments, known relationships between different opening angles and valve expansion diameters are stored in the memory of the control unit 111[a]. The numerical value of the expansion diameter of the valve 114 may be derived from the opening angle $\beta$, based on any of: mathematical formulas, graphs, and/or tables, which may be stored in the memory. According to some embodiments, a visual indication of the expansion diameter may be displayed on a digital screen 113*a*, and may include: a numerical value, an icon or other graphical symbol, a textual message, or any combination thereof.

According to some embodiments, the control unit 111[a] may be further configured to control the actuation assemblies 150 and/or the re-compression assembly 180, to expand and/or contract the prosthetic valve 114[a], according to pre-programmed expansion/contraction algorithms. In one example, the handle 110[a] may be maneuvered to gradually expand the valve 114[a] (for example, by pulling the actuators 151, which are attached at this stage to the expansion and locking assemblies 134). During the expansion of the valve 114, the flex sensing assembly 156 provides flex signals to the control unit 111[a], from which the valve diameter may be derived. The data may be interpreted by the control unit 111[a], and may be visually displayed via a display 113*a* or LED lights 113*b* comprised in the handle 110. The displayed interpreted data, which can include real-time valve expansion diameter, may assist the clinician in decision making regarding the next required steps of the implantation procedure, or serve as input data for algorithms executed by the control unit 111[a] to automatically expand or adjust valve diameter.

Once the valve 114 is sufficiently expanded, the handle 110 can be further maneuvered to release the actuation assemblies 150 from the valve 114[a], for example as elaborated in conjunction with FIGS. 4A-4C, and/or to decouple at least a portion of the flex sensing assembly 156 from the valve 114.

According to some embodiments, the control unit 111[a], and/or the visual interface 112, may be provided as distinct components separated from the delivery apparatus 102, which can be operatively connected thereto, for example using wires/cables, or via wireless communication protocols. According to additional embodiments, the control unit, and/or the visual interface 112, are integrated within the handle 110. For example, a processor and other electrical components of control unit 111[a] can be located within the handle 110, and the visual interface 112 may be located on an exterior surface of the handle 110, such that it can be viewed by a clinician during the implantation procedure.

In the exemplary embodiment shown in FIG. 5C, the first angle $\alpha_1$ is derived from the bend measurement signals of the first flex sensor 170*a* relative to the sensor shaft axis 22, and the second angle $\alpha_2$ is derived from the bend measurement signals of the second flex sensor 170*b* relative to the sensor shaft axis 22, wherein the sensor shaft axis 22 is shown to be oriented substantially parallel to the valve longitudinal axis 20. If the sensor shaft axis 22 indeed remains substantially parallel to the valve longitudinal axis 20 during valve expansion, it may be argued that one flex sensor 170 may be sufficient to derive an opening angle $\beta$. For example, a single flex sensor, such as the first flex sensor 170*a*, may be used to measure the first angle $\alpha_1$, which should be identical to the second angle $\alpha_2$ in such cases, thus enabling derivation of the opening angle $\beta$ from a simple multiplication of the first angle $\alpha_1$.

Figure 6A:
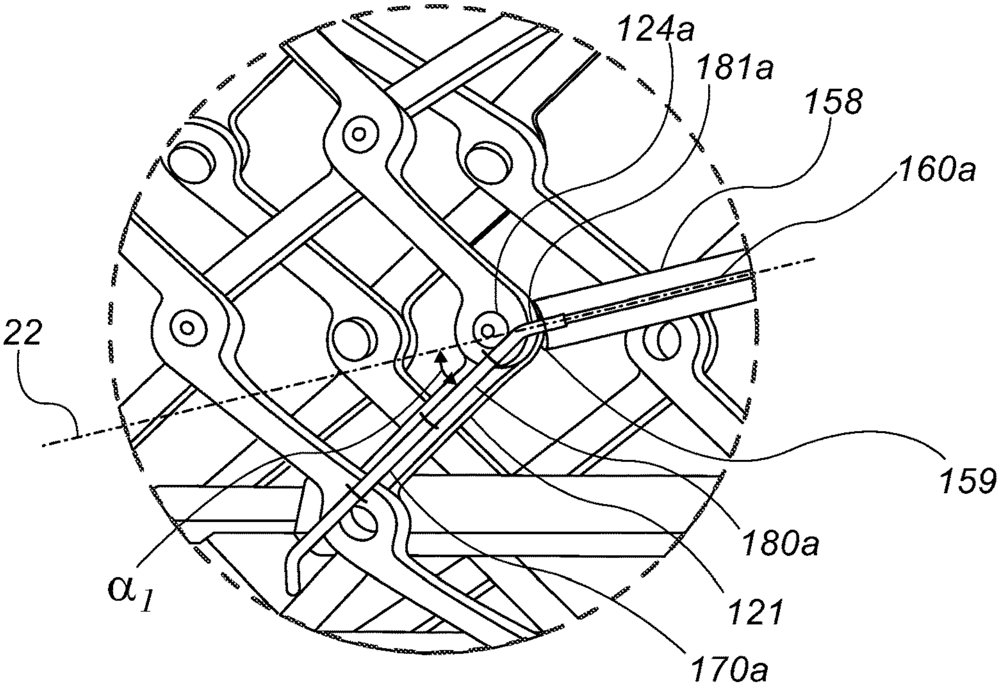
FIG. 6A shows a zoomed-in view of a flex sensing assembly equipped with a single flex sensor coupled to a single strut, according to some embodiments.

In cases wherein the orientation of the sensor shaft axis 22 cannot be guaranteed to be predictable or constant throughout valve expansion, it may be required for the flex sensing assembly 156 to include more than one flex sensor 170*a*, to ensure accurate derivation of the opening angle $\beta$. FIG. 6A shows an exemplary embodiment of a flex sensing assembly 156 equipped with a single flex sensor 170*a*, coupled to a single strut 121*a*. The nosecone 109 and nosecone shaft 108 are omitted from view in FIGS. 6A-14E for the sake of clarity. As shown in FIG. 6A, the sensor shaft axis 22 may be oriented at a non-parallel orientation (e.g., angled) relative to the valve longitudinal axis 20, or any axis parallel to valve longitudinal axis 20. If the orientation of the sensor shaft axis 22 is known, and remains constant throughout valve expansion, a single flex sensor 170*a* may still suffice for derivation of the opening angle $\beta$ from a single angle $\alpha_1$ relative to the sensor shaft axis 22. However, if the sensor shaft axis 22 cannot be determined, and more specifically, if the orientation of the sensor shaft 158, and hence, the orientation of the sensor shaft axis 22, is subject to changes during the valve implantation procedure, the opening angle $\beta$ may not be accurately derived only from the single angle $\alpha_1$.

Figure 6B:
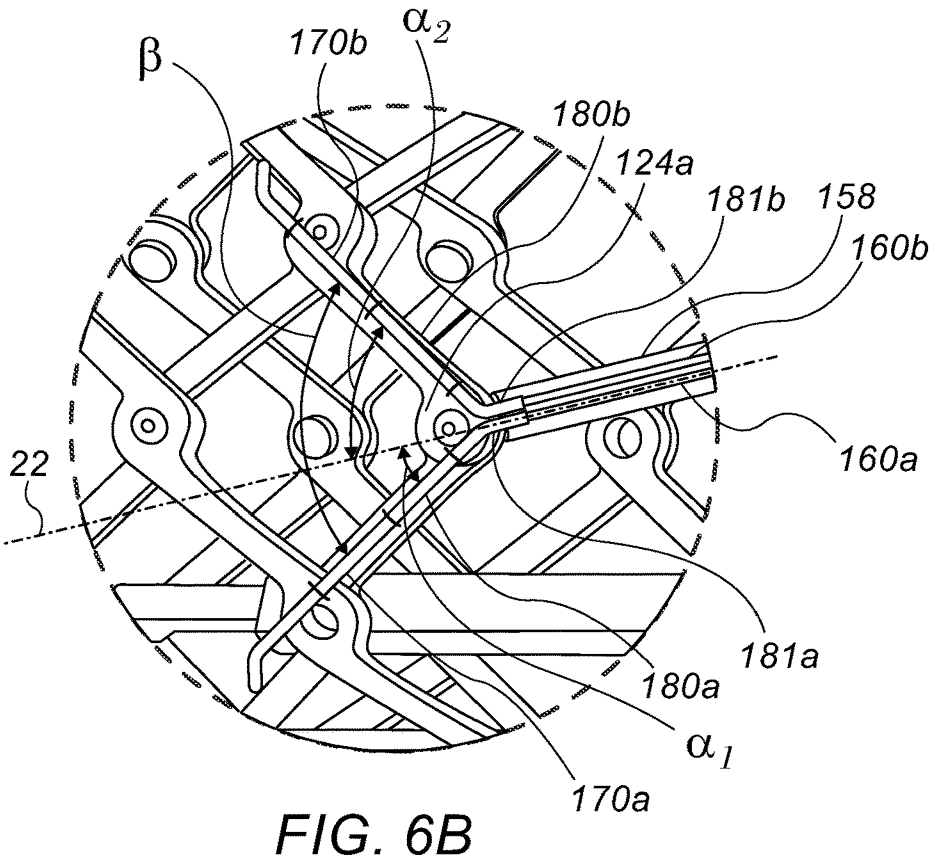
FIG. 6B shows a zoomed-in view of a flex sensing assembly equipped with two flex sensor coupled to two intersecting struts, according to some embodiments.

FIG. 6B shows an exemplary configuration of a flex sensing assembly 156 equipped with first flex sensor 170*a*, coupled to the first strut 121*a*, and a second flex sensor 170*b*, coupled to the intersecting second strut 121*b*, wherein the sensor shaft axis 22 may be oriented at a non-parallel orientation (e.g., angled) relative to the valve longitudinal axis 20. In this configuration, the opening angle $\beta$ may be derived from the sum of non-equal angles $\alpha_1$ and $\alpha_2$ at any measurement time instance, regardless of the relative orientation of the sensor shaft 158 and the sensor shaft axis 22.

This configuration, advantageously, enables continuous derivation of the opening angle β, without requiring affixation of the sensor shaft 158 to a predetermined angular orientation.

Figure 7:
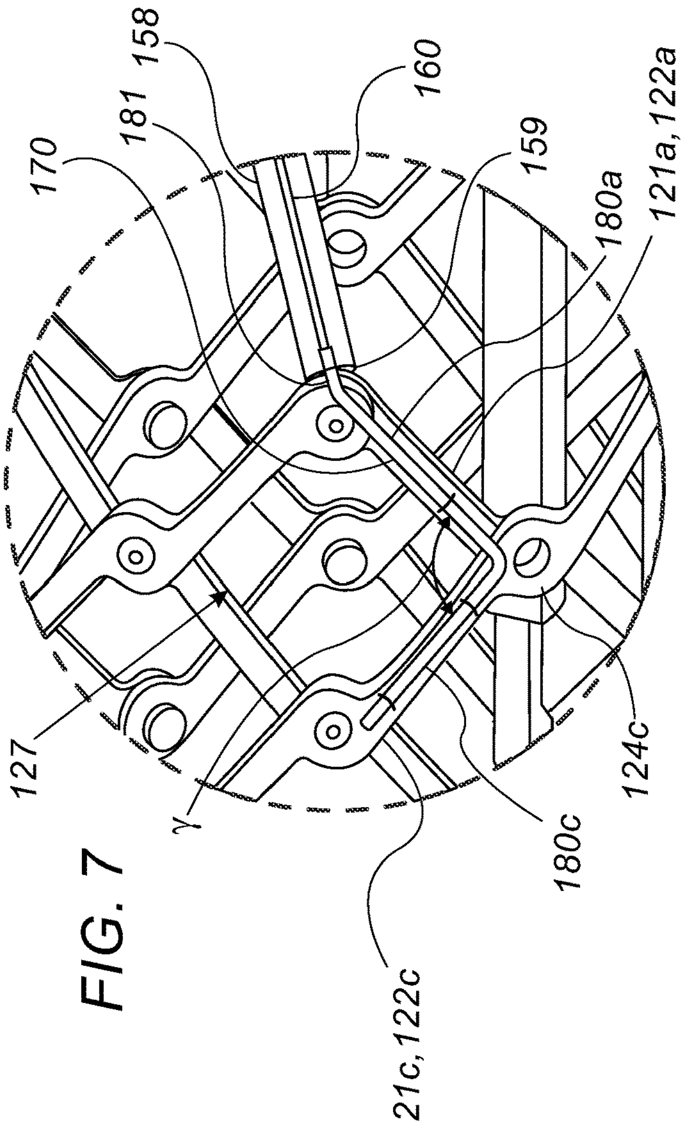
FIG. 7 shows a zoomed-in view of a flex sensing assembly equipped with a single flex sensor coupled to two intersecting struts, according to some embodiments.

FIG. 7 shows an exemplary embodiment of a flex sensing assembly 156 equipped with a single flex sensor 170, coupled to two intersecting strut 121*a* and 121*c*. As shown, the flex sensor 170 may include a first (e.g., proximal) bending portion 180*a*, coupled to a first strut 121*a*, for example extending along a first strut portion 122*a* up to an intersection junction 124*c*, and a second (e.g., distal) bending portion 180*c*, coupled to a second strut 121*c*, for example extending along a second strut portion 122*c* from the intersection junction 124*c*. An opening angle γ is defined between the first strut 121*a* and the second strut 121*c* at the common intersection junction 124*c*. During expansion, the flex sensor 170 may assume a V-shaped configuration, having the apex of the V-shape at the intersection junction 124*c*. The opening angle γ can be derived from the bending of the second bending portion 180*c* relative to the first bending portion 180*a*, and correlated in turn with valve expansion diameter.

While the opening angle γ shown in FIG. 7 is measured between different intersecting struts 121 that the opening angle β of FIG. 6B, for example, it will be clear that any angle measured between a strut 121 and another structure of the valve 114 intersecting therewith, such as another intersecting strut 121, may serve as the valve opening angle that can be correlated with valve expansion diameter. In the case of diamond-shaped cells 127, as illustrated in FIG. 7 for example, each angle at any junction 124 of the cell 127 may be used to easily derive any other angle of the cell 127. As such, any embodiment of the current invention, referring to an opening angle β, is similarly applicable to any other opening angle of the valve 114, such as opening angle γ.

According to some embodiments, the non-bending portion 181 is coupled to an expansion and locking assembly 134 or any component thereof (e.g., an actuator outer member 136), while the bending portion 180 is coupled to a strut 121$^a$, which may pivot relative to the expansion and locking assembly 134 during valve expansion or contraction. Coupling of the non-bending portion 181 to the expansion and locking assembly 134 may be realized as direct coupling or as indirect coupling. For example, direct coupling may be direct attachment of the non-bending portion 181 to an outer member 136, for example by gluing, welding, riveting, or various types of coupling member 188. In another example, indirect coupling may be realized by attachment of a sensor shaft 158 (e.g., a distal portion thereof) to an outer member 136, while the non-bending portion 181 is at least partially disposed within the sensor shaft 158.

Figure 8:
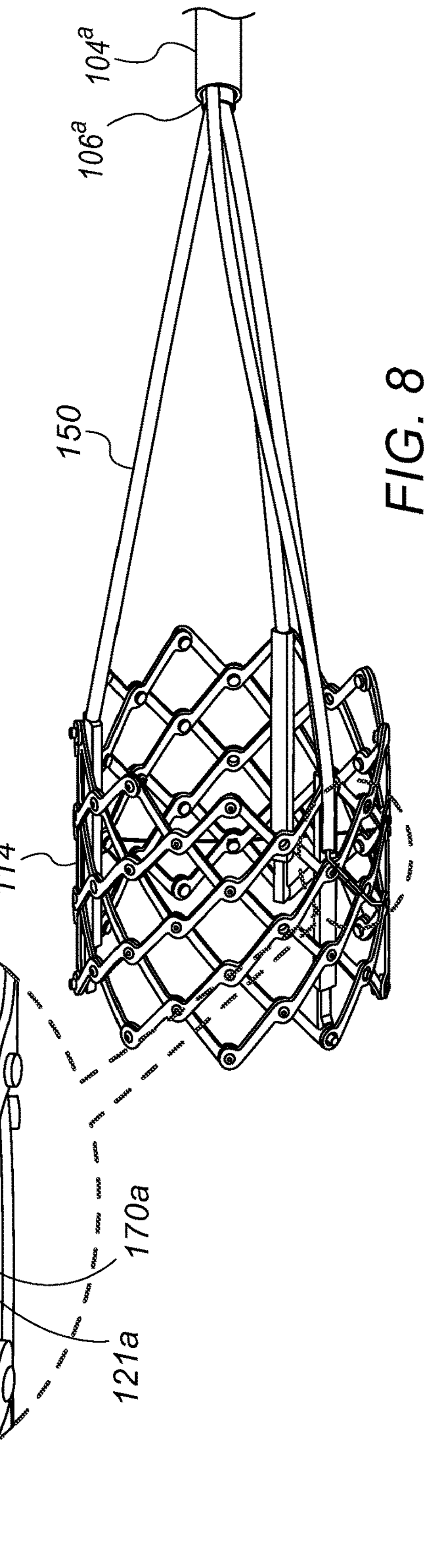
FIG. 8 shows a flex sensing assembly coupled to an actuator assembly, according to some embodiments.
Figure 8:
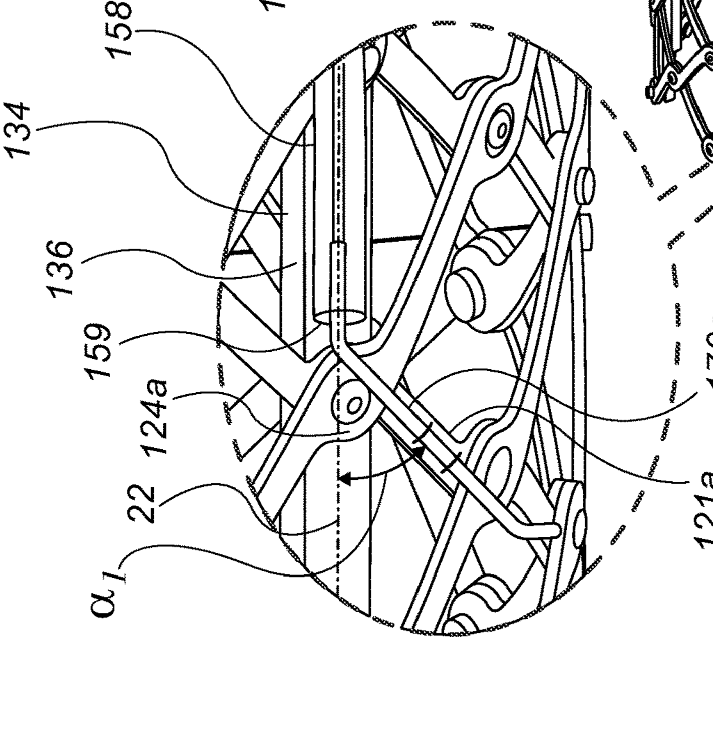

FIG. 8 shows an exemplary embodiment of a flex sensing assembly 156 equipped with a single flex sensor 170*a*, wherein the sensor shaft 158 is coupled to the expansion and locking assembly 134, for example, to the outer member 136, and the flex sensor 170*a* is coupled to a single strut 121*a* intersecting with the expansion and locking assembly 134. In this configuration, since the sensor shaft axis 22 remains oriented parallel to the expansion and locking assembly 134 (which is usually parallel with the valve longitudinal axis 20), the single flex sensor 170*a* can suffice for derivation of the opening angle β from a single angle $\alpha_1$ relative to the sensor shaft axis 22.

Reference is now made to FIGS. 9A-14E, showing different embodiments of a flex sensing assembly 156. While all of the embodiments illustrated throughout FIGS. 9A-14E show configurations of flex sensing assemblies 156 equipped with two flex sensors, coupled to two intersecting struts 121, this is for purposes of illustrations only, and the same embodiments may in fact be implemented with a single flex sensor, for example coupled to the prosthetic valve 114 according to any one of the configurations described and illustrated in conjunction with FIGS. 6A-8.

As described above, the flex sensor 170 may be operatively coupled, for example via communication channel 160, to the control unit 111$^a$, and configured such that control unit 111$^a$ can read the output of the flex sensor 170. In response to the flex sensor 170 being flexed, the output of the flex sensor 170 changes. According to some embodiments, the output of the at least one flex sensor is an optic signal. According to some embodiments, the flex sensing assembly 156 comprises an optic fiber assembly 257, wherein the communication channel is provided in the form of an optic conductor 260, and the flex sensor is provided in the form of an optic flex sensor 270. Utilization of optic fiber sensors may be advantageous due to their light weight, miniature dimensions, low power consumption, high sensitivity, environmental ruggedness and low cost.

Figure 9A:
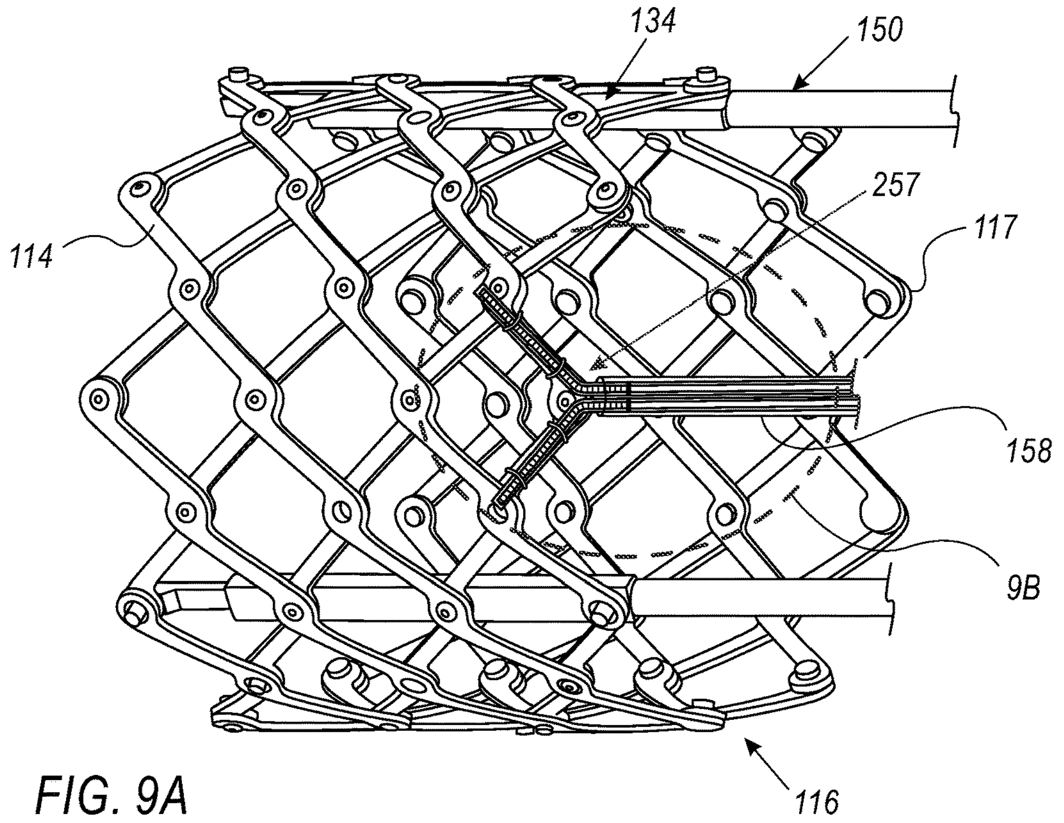
FIGS. 9A-9C show different views of a delivery assembly equipped with optic fiber assemblies, according to some embodiments.
Figure 9B:
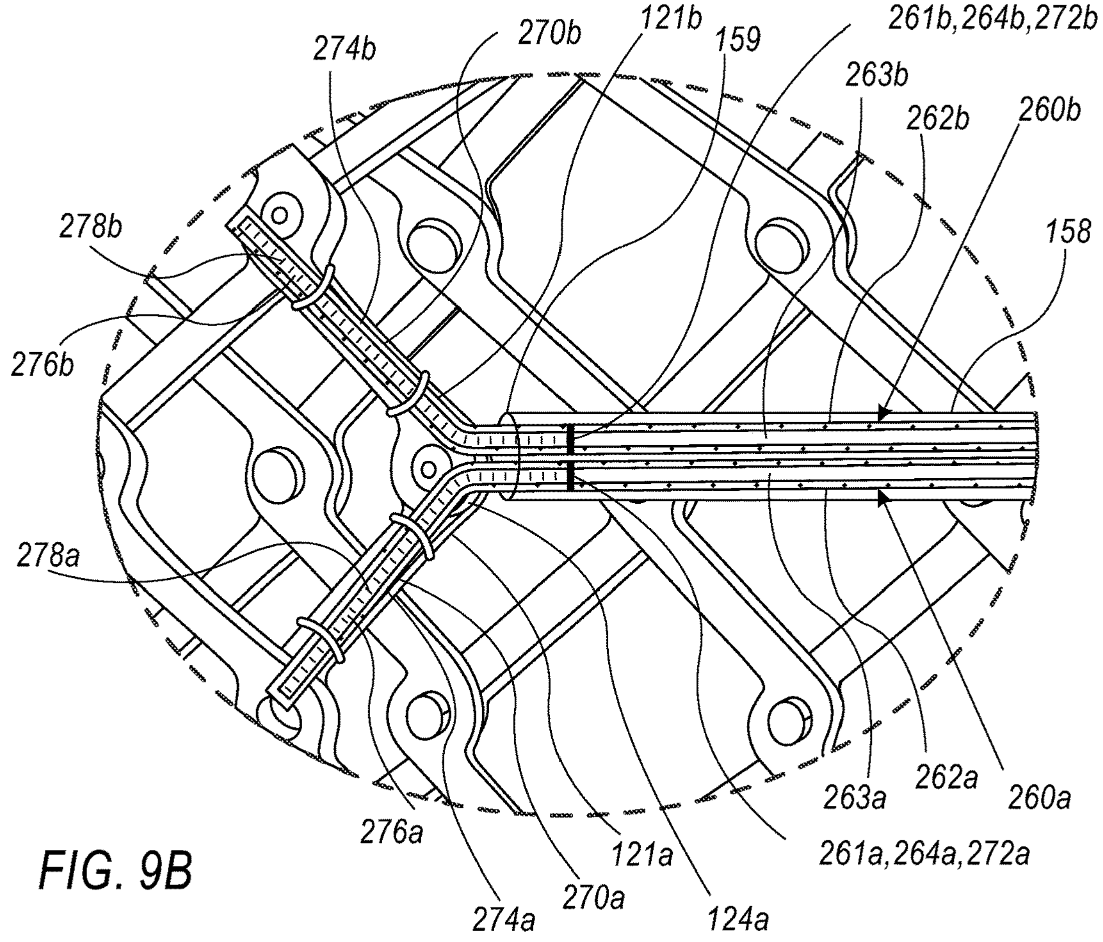
Figure 9C:
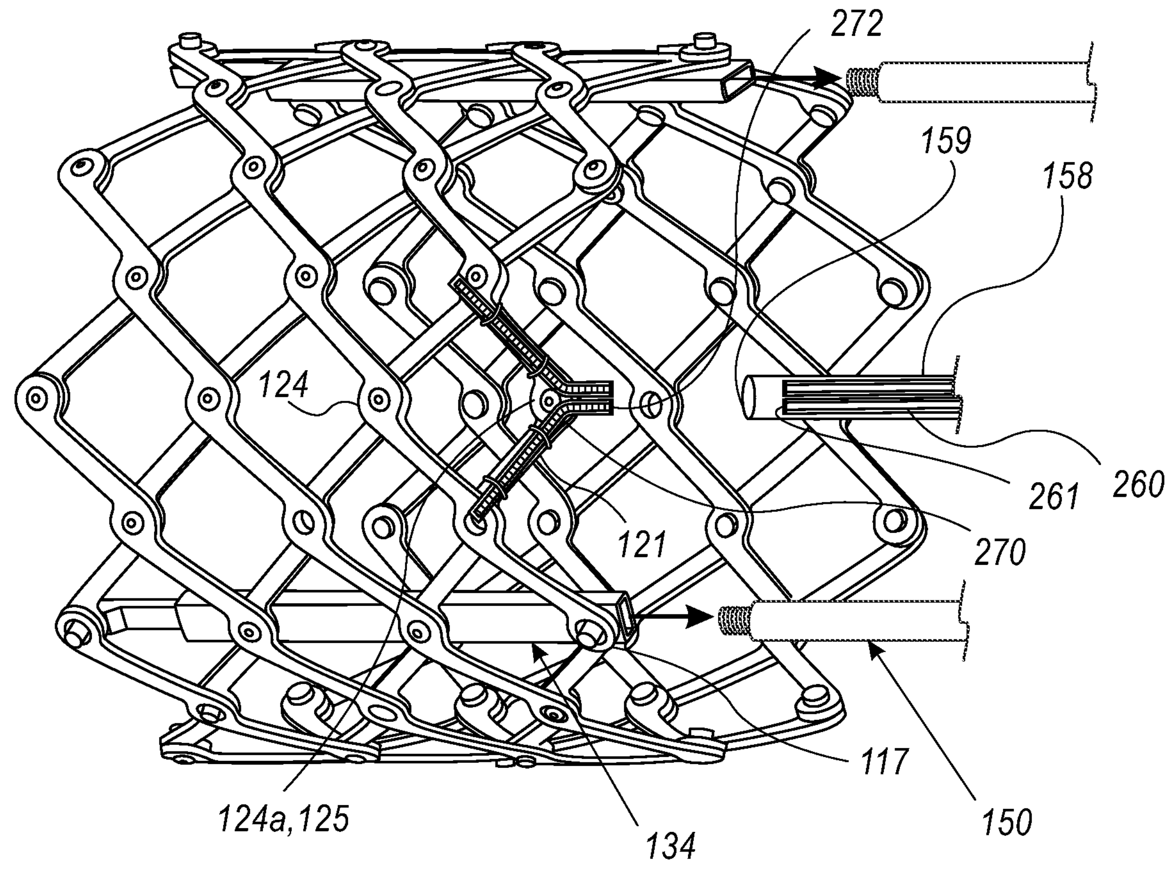

FIG. 9A shows an exemplary embodiment of a flex sensing assembly 156 equipped with two optic fiber assemblies 257, wherein a first optic fiber assembly 257*a* comprises a first optic flex sensor 270*a* coupled to a first strut 121*a*, and a second optic fiber assembly 257*b* comprises a second optic flex sensor 270*b* coupled to a second strut 121*b*. An example of a valve 114$^a$ is shown in FIGS. 9A-9C with only two expansion and locking assemblies 134 for clarity. However, any other number of expansion and locking assemblies 134 (e.g., three) is contemplated. FIG. 9B shows a zoomed-in view of region 9B in FIG. 9A.

According to some embodiments, the optic conductors 260 and the respective optic flex sensor 270 are detachably optically coupled to each other. Specifically, each optic fiber assembly 257 comprises an optic conductor 260 extending from the handle 110, optionally through a lumen of the sensor shaft 158, up to an optic conductor distal end 261, and an optic flex sensor 270 distal to the optic conductor 260, coupled to a respective strut 121 (e.g., to a strut section 122). Each optic conductor 260 comprises an optic conductor core 263, surrounded by an optic conductor cladding 262, and each optic flex sensor 270 comprises an optic sensor core 276 surrounded by an optic sensor cladding 274. Each of the optic conductors 260 and/or optic flex sensor 270 can further include a surrounding polymeric buffer coating (not shown) around the claddings 262, 274, serving as an additional protective buffer from the surrounding environment.

According to some embodiments, the outer diameter of the optic conductor 260 is substantially equal to the outer diameter of the optic flex sensor 270. According to some embodiments, the outer diameter of the optic conductor core 263 is substantially equal to the outer diameter of the optic sensor core 276.

The term 'substantially equal', when referring to a specific measure as used herein, means no more and no less than 10% of the measure. For example, a diameter of one component is substantially equal to the diameter of a second component, if the diameter of the first component is within the boundaries of 90%-110% of the second diameter.

According to some embodiments, as further shown in FIGS. 9A-9B, each optic conductor 260 is detachably optically coupled to the respective optic flex sensor 270. For example, each optic conductor 260 may be detachably optically coupled to the respective optic flex sensor 270.

According to some embodiments, the interface 164 of each optic fiber assembly 257 is provided in the form of an optic interface 264 between the optic conductor distal end 261 and the optic sensor proximal end 272. The interface 264 is configured to provide detachable optical coupling between the optic conductor 260 and optic flex sensor 270, such that signals may be communicated there-between when optically coupled to each other, and wherein both are optically decoupled when the optic conductor distal end 261 is detached from the optic sensor proximal end 272. Decoupling of the optic conductor 260 from the second optic flex sensor 270 may be controlled by the handle 110, and may be facilitated by applying a pull force exceeding a predefined threshold magnitude to the optic conductor 260. According to some embodiments, decoupling of the optic conductor 260 from the second optic flex sensor 270 may be executed simultaneously with the release of the actuators 151 from the expansion and locking assemblies 134, when implemented for use with mechanically expandable valves 114[a].

According to some embodiments, optical coupling between the optic conductor 260 and the optic flex sensor 270 is achieved by placement of the optic conductor distal end 261 in contact with the optic sensor proximal end 272, and optical decoupling is achieved by pulling the optic conductor distal end 261 away from the optic sensor proximal end 272. In such embodiments, the interface 264 between the optic conductor 260 and the optic flex sensor 270 may be defined as the contact area between the optic conductor distal end 261 and the optic sensor proximal end 272.

According to some embodiments, the optical coupling of the interface 264 is realized as a physical contact (PC) connection between the optic conductor distal end 261 and the optic sensor proximal end 272, wherein the optic conductor core 263 and the optic sensor core 276 are aligned with each so as to optimize performance and minimize optic light loss at the interface 264 there between.

According to some embodiments, the optical coupling 264 is realized as a flat PC, when the optic conductor distal end 261 and the optic sensor proximal end 272 comprise flat, and preferably polished, end faces. According to some embodiments, the optical coupling 264 is realized as an angled PC, when the optic conductor distal end 261 and the optic sensor proximal end 272 comprise complementary angled end faces, for example at an angle of about 8 degrees (embodiment not shown).

The term 'about', as used herein, means in a range of ±10% from a referred value.

According to some embodiments, the interface 264 comprises an optical connector, configured to releasably couple the optic conductor distal end 261 and the optic sensor proximal end 272 and allow signal communication there between. When communicating signals between different optic fiber components, alignment of the optic cores may be desirable, as even a slight misalignment may lead to signal losses. According to some embodiments, an optical connector 264 includes alignment features configured to align the optic conductor distal end 261 and the optic sensor proximal end 272.

FIG. 9C shows the optic conductors 260 decoupled from the optic flex sensors 270, being pulled along with the actuation assemblies 150 in a proximally oriented direction 14, away from the valve 114, while the optic flex sensors 270 remain coupled to the valve 114, and more specifically, to the respective struts 121.

Optic signals are conventionally passed through optic cores. To confine optic signals to the optic conductor core 263 and the optic sensor core 276, their refractive index is typically greater than that of the optic conductor cladding 262 and the optic sensor cladding 274, respectively. According to some embodiments, optic signals can pass through the optic conductor core 263 and the optic sensor core 276 by means of total internal reflection. However, if the angle of incidence of light striking the boundary between the optic sensor core 276 and the optic sensor cladding 274 changes, a proportional amount of the optic signal may pass outside of the optic flex sensor 270 and not be reflected internally. As such, an optic flex sensor 270 which flexes or bends, will exhibit some degree of optic signal loss. Therefore, the extent of bending of an optic flex sensor 270 can be detected by monitoring the optic signals transmitted via the optic conductor 260.

According to some embodiments, the optic flex sensor 270 comprises a plurality of axially spaced Fiber Bragg Gratings (FBGs) 278, disposed along at least a portion of the optic sensor core 276. The reflected light from the optic sensor core 276 is a sum of reflections from each of the FBGs along the optic sensor core 276. Each reflection from each FBG may be modulated with a distinct frequency (determined by the position of the FBG), enabling the reflection spectrum to be separated using the data acquired from the optic sensor core 276. The shift in each FBG is proportional to the strain in the optic sensor core 276 at the location of the FBG, such that the modulated optic signals are proportional to the degree of bending applied at the axial location of the FBGs.

In use, a delivery assembly 100 may be utilized to deliver a prosthetic valve 114 toward a desired implantation site in a crimped state, having the optic flex sensors 270 coupled to intersecting struts 121, while the optic conductors 260 are optically coupled to the optic flex sensors 270.

Once the crimped valve 114 is positioned at the desired implantation site, the handle 110 may be maneuvered to gradually expand the valve 114 (for example, by pulling the actuators 151, which are attached at this stage to the expansion and locking assemblies 134, in the case of mechanically expandable valves 114[a]). During the expansion of the valve 114, the at least one optic fiber assembly 257 provides real-time feedback in the form of optic signals, correlated with flex of the optic flex sensor 270 coupled to a strut 121, from which the valve diameter may be derived (in example, according to optic signals received from two optic fiber assemblies 257, coupled to two intersecting struts 121). The data may be interpreted by the control unit 111[a], and may be visually displayed via a display **113*a* or LED lights 113*b* positioned at the handle 110**. The displayed interpreted data, which can include real-time valve expansion diameter, may assist the clinician in decision making regarding the next required steps of the implantation procedure.

Once the valve 114 is sufficiently expanded, the handle 110 can be further maneuvered to release the actuation assemblies 150 from the valve 114 (if the valve is a mechanically expandable valve 114[a]), for example as elaborated above in conjunction with FIGS. 4A-4C, and/or to decouple the optic conductors 260 from the optic flex sensors 270, as elaborated above and shown in FIG. 9C.

FIGS. 9A-9C show an exemplary configuration in which the interfaces 264 are located proximal to an intersection junction 124, wherein the intersection junction 124 is an outflow apex 125, such that upon detachment from the optic conductors 260, the non-bending portions 181 are shown to extend proximally from the outflow apex 125. In alternative configurations, the intersection junction 124 may be a non-apical junction, for example such as proximal-most non-apical junction 124*a* distal to the outflow apices 125, such that upon detachment from the optic conductors 260, the non-bending portion 181 will not extend proximally beyond the outflow end 117.

While the interface 264 between the optically coupled optic conductor 260 and optic flex sensor 270 is exemplified above as a simple contact between their end faces, it will be clear that other interfaces may be utilized for detachable optical coupling. For example, the interface 264 may include a gap configured to transfer light between the optic conductor 260 core 263 and optic sensor core 276, with minimal interference. For example, the optic conductor distal end 261 may be glued or fused to the optic sensor proximal end 272 in a manner that application of a selected amount of pull force, or alternatively, rotational force, can break the adhesive bonds and allow the optic conductor 260 to be withdrawn, and optically decoupled from the optic flex sensor 270.

While the optic fiber assembly 257 is described and illustrated in conjunction with FIG. 9C above with a detachable interface 264 between each optic conductor 260 and the respective optic flex sensor 270, it will be clear that in alternative embodiments, the optic fiber assembly 257 may be provided with a non-detachable interface 264. For example, the optic conductors 260 may be pulled along with the optic flex sensor 270, away from the valve 114, according to any of the embodiments that will be described in conjunction with FIGS. 11A-14E below.

According to some embodiments, the output of the at least one flex sensor is an electrical signal. The electrical signal can be in the form of a current, a voltage, a resistance, or changes in the same. For example, a flex sensor 170 can be configured such that its resistance varies as a function of bending of the flex sensor 170. In such embodiments, the communication channel 160 can be provided in the form of an electric wire or cable, having its distal end 161 electrically coupled at the interface 164 with the flex sensor 170. For example, the interface 164 can include electrical connection to end terminals (not shown) of the flex sensor 170.

According to some embodiments, each communication channel 160 may include various electrically conductive materials, such as copper, aluminum, silver, gold, and various alloys such as tentalum/platinum, MP35N and the like. An insulator (not shown) can surround each communication channel 160. The insulator can include various electrically insulating materials, such as electrically insulating polymers.

According to some embodiments, the at least one communication channel 160 is further configured to deliver power to the at least one sensor 170. According to some embodiments, the communication channel 160 is connected to a proximal power source (not shown), for example within the handle 110, configured to provide power to operate the at least one flex sensor 170. According to some embodiments, the communication channel 160 is configured to deliver signals from, and/or to, the flex sensor 170.

According to some embodiments, an electrically conductive communication channel 160 is releasably coupled to the flex sensor 170. In such embodiments, the communication channel 160 may be coupled to the flex sensor 170 during prosthetic valve 114 delivery to the implantation site, and during the implantation procedure, and may be decoupled or released from the flex sensor 170 after the implantation procedure is completed, allowing the communication channel 160 to be retracted along with the remainder of the delivery apparatus 102 from the patient's body. In such embodiments, the prosthetic valve 114 may remain implanted in the patient's body, having the at least one flex sensor 170 attached thereto in a non-operative mode.

Figure 10A:
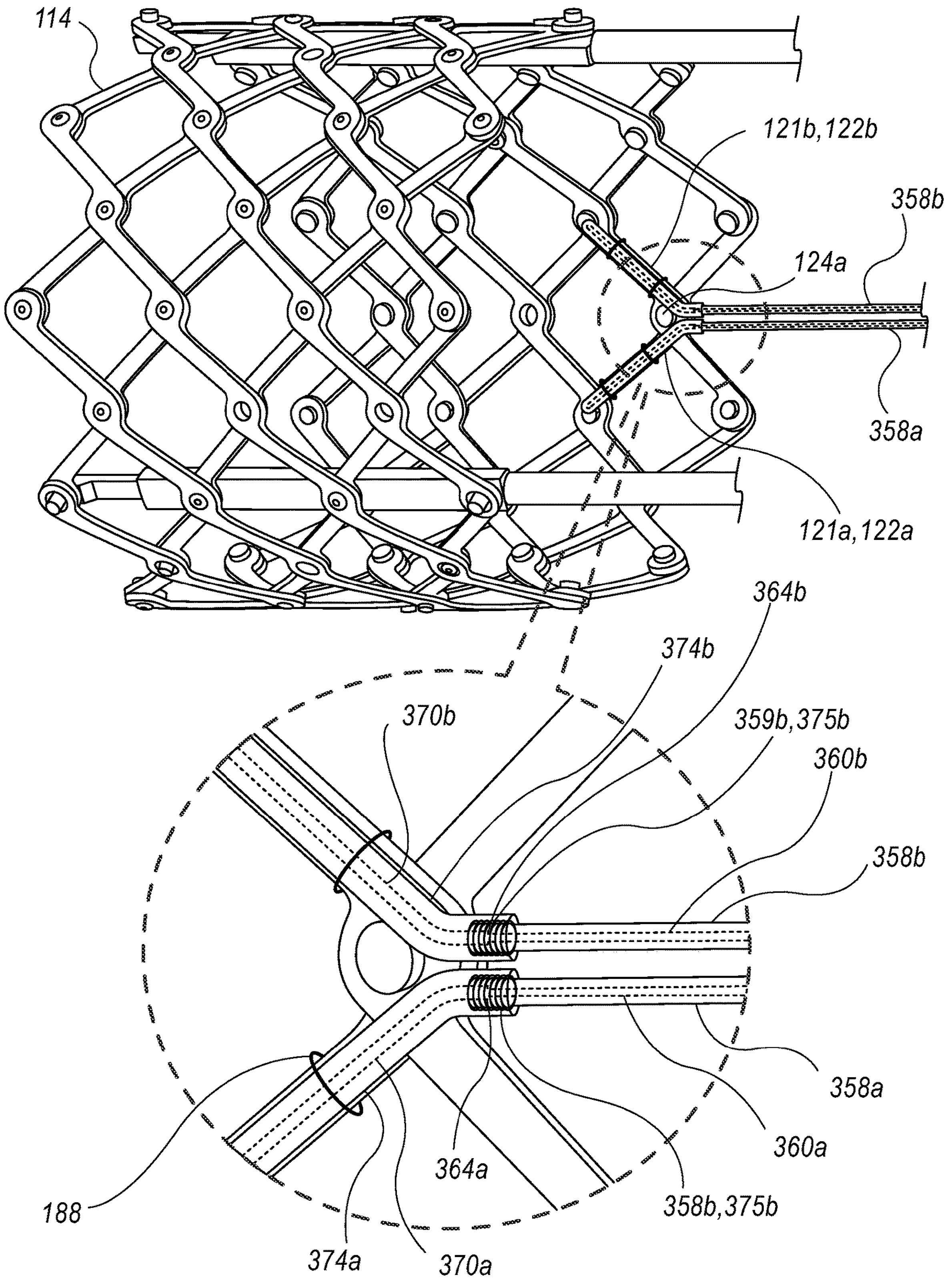
FIGS. 10A-10C show different operational states of a detachable coupling mechanism between communication channels and flex sensors, according to some embodiments.
Figure 10B:
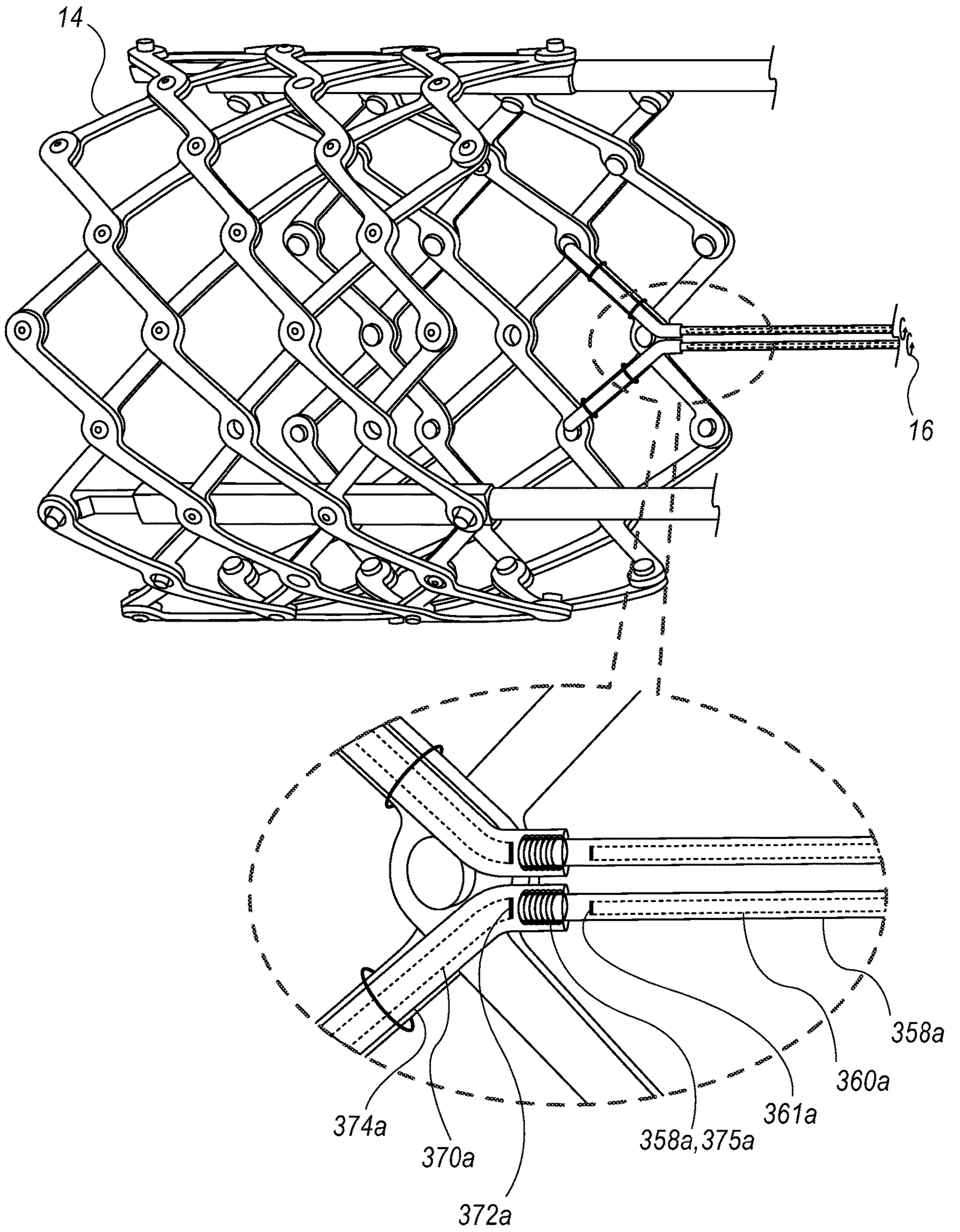
Figure 10C:
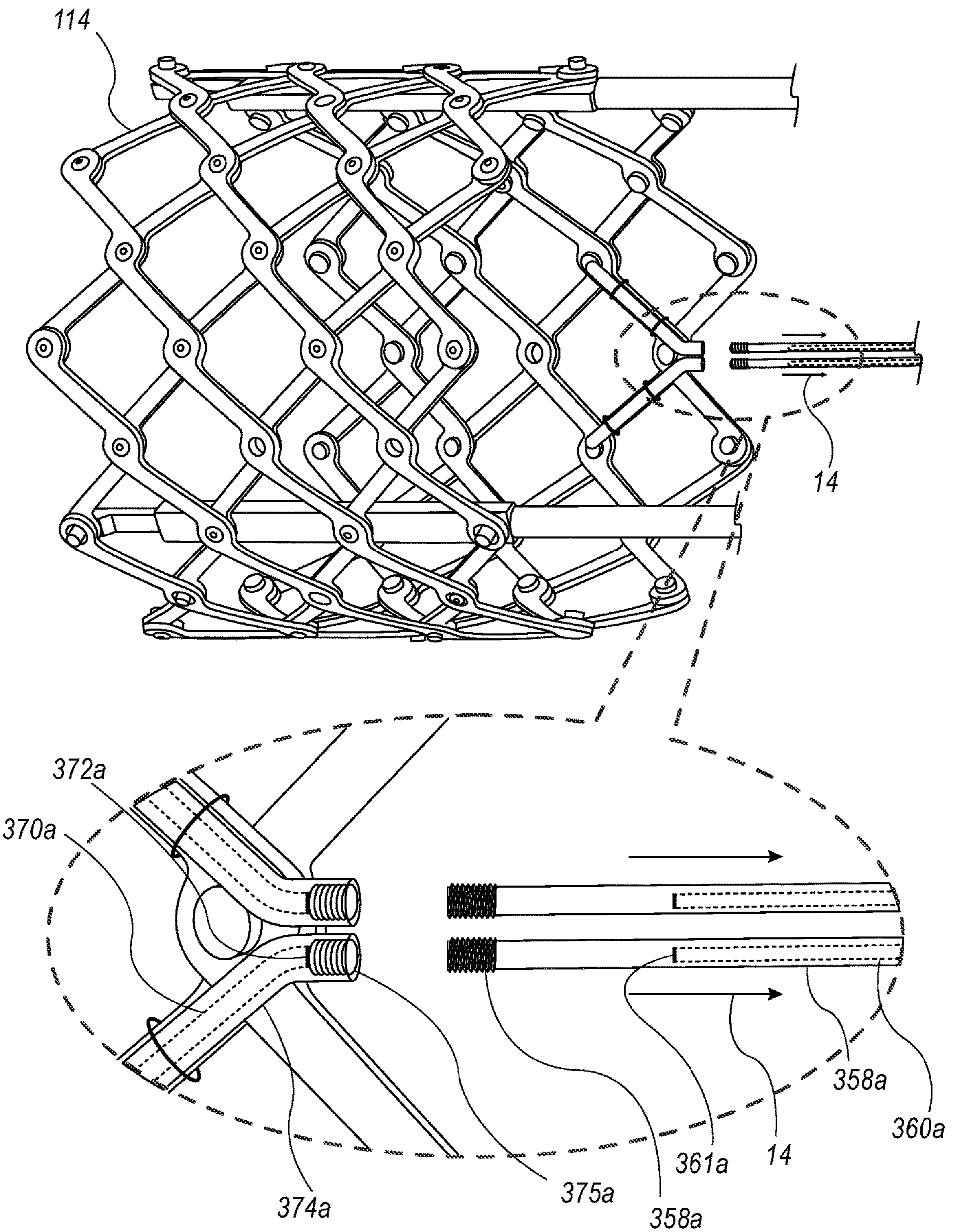

Reference is now made to FIGS. 10A-10C, illustrating a non-binding configuration of a detachable coupling mechanism between a communication channel 160 and a flex sensor 170. According to some embodiments, as shown in FIG. 10A, the flex sensor assembly 156 further comprises at least one sensor housing 374 attached to a strut 121, and at least one detachable shaft 358 extending distally from the handle 110, having least a portion of the a corresponding communication channel 160 extending through a lumen thereof, and axially movable relative thereto. The valve 114 is shown in FIGS. 10A-10C with only two actuator assemblies 134 for clarity. However, any other number of actuator assemblies 134 (e.g., three) is contemplated.

According to some embodiments, the at least one flex sensor 170 is at least partially retained within a sensor housing 374, and is locally affixed to the sensor housing 374, for example by gluing, welding, and the like. The sensor housing 374 may be provided with a lumen, a bore, or any other channel for accommodating the flex sensor 170. The sensor housing 374 may be affixed to the respective strut 121, for example by gluing, welding, or an affixing coupling member 188. Additionally or alternatively, the sensor housing 374 may be coupled to the strut 121 via at least one non-affixing coupling member 188.

The term "locally affixed", as used herein with reference to the flex sensor 170, means that the flex sensor is rigidly affixed to the respective sensor housing 374 at a local point or region of the flex sensor 170 (e.g., a proximal region thereof), while at least one other portion thereof (e.g., a distal portion) is not affixed to the sensor housing 170, so as to enable axial displacement of at least a portion of the flex sensor 170 relative to the respective strut 121, during valve expansion or compression.

According to some embodiments, the at least one communication channel 160 extends through a lumen of the detachable shaft 358, wherein the detachable shaft 358 is detachably coupled to the sensor housing 374. The communication channel 160 may further extend into the sensor housing 374, and is detachably coupled to the flex sensor 170. The detachable shaft 358 is configured to isolate the communication channel 160 extending therethrough, and the interface 164 with the flex sensor 170, from the ambient flow (e.g. blood flow), when the detachable shaft 358 is coupled to the sensor housing 374.

FIGS. 10A-10C illustrate an embodiment of sensor housings 374 provided in the form of sleeves or tubes, accommodating the entire length of respective flex sensors 170 within lumens or bores thereof. In alternative embodiments, each sensor housing 374 may be provided as a short nut-like member (not shown), having the respective flex sensor 170 extending through a central bore thereof, while at least a portion of the flex sensor 170 extends further distally away from the sensor housing 374, and may be coupled to the respective strut 121 via at least one non-affixing coupling member 188.

According to some embodiments, the communication channel distal end 161 is detachably coupled to the flex sensor proximal end 172 at interface 364. Similarly, the detachable shaft distal end 359 (see FIG. 10C) is detachably coupled to the sensor housing proximal end 375. According to some embodiments, the sensor housing proximal end 375 comprises a threaded bore (see FIG. 10C), and the detachable shaft distal end 359 comprises an external threading, configured to threadedly engage with the sensor housing threaded bore 375.

In the state shown in FIG. 10A, the first 161*a* and second 161*b* communication channel distal ends are coupled to the first 172*a* and second 172*b* flex sensor proximal ends, respectively, and the first 359*a* and second 359*b* detachable shaft distal threaded ends are coupled to (e.g., threaded with) the first 375*a* and second 375*b* sensor housing proximal threaded ends, respectively. In this state, power may be supplied to the flex sensor 170*a* and 170*b* via the communication channels 160*a* and 160*b*, respectively, and signals may be transmitted from and to the flex sensors 170*a* and 170*b* via the communication channels 160*a* and 160*b*, respectively.

FIG. 10B shows a state during disengagement of the communication channels 160*a* and 160*b* from the flex sensors 170*a* and 170*b*, respectively. According to some embodiments, each communication channel 160 may be coupled to the respective sensor 170 such that application of a pull force in the proximal direction 14, beyond a predetermined threshold magnitude, may disengage the communication channel 160 from the flex sensor 170. According to some embodiments, the force required to disengage the communication channel 160 from the flex sensor 170 may be applied manually. According to some embodiments, the force required to disengage the communication channel 160 from the flex sensor 170 may be applied by a mechanical or electrical actuation mechanism at the handle 110.

As shown in FIG. 10B, while the communication channel 160 is decoupled from the flex sensor 170, the detachable shaft 358 remains coupled to the sensor housing 374, thereby isolating the communication channel 160 from the surrounding environment of the blood flow. This allows the communication channel 160 to be detached and pulled from the flex sensor 170 while avoiding the risk of exposing the surrounding blood flow or other tissues to electrical current thereof.

Once the communication channel 160 is detached from the flex sensor 170 and pulled away therefrom, the detachable shaft 358 may be rotated, for example in a direction 16 around its axis of symmetry, so as to detach from the sensor housing 374. According to some embodiments, the communication channel 160 is pulled along a sufficient distance prior to disengaging the detachable shaft 358 from the sensor housing 374, such that once the detachable shaft 358 is detached, the communication channel 160 cannot be exposed to the blood flow flowing through the lumen of the detachable shaft 358.

According to some embodiments, the detachable shaft 358 extends through a lumen of the sensor shaft 158. Alternatively, the detachable shafts 358 may extend through the lumen of the delivery shaft 106, without an additional dedicated sensor shaft 158.

FIG. 10C shows a more advanced state of disengagement of the communication channels 160 from the flex sensors 170, compared to the state shown in FIG. 10B. The state shown in FIG. 10C is achieved by further pulling the detachable shaft 358 in a proximal direction 14, away from the sensor housing 374, after being disengaged therefrom. This mechanism allows the communication channel 160, along with the detachable shaft 358, to be disengaged from the flex sensor 170 and sensor housing 374, and retracted from the patient's body at the end of the implantation procedure, without risking exposure of the native tissues or blood flow to electrical current flowing through the communication channel 160 during such disengagement.

While the detachable coupling mechanism described hereinabove and illustrated in FIGS. 10A-C, is described as advantageous when utilized with electrically conductive communication channels 160 and flex sensors 170, it will be clear that the same mechanism can be similarly utilized for optic components, such as optic conductors 260 and optic flex sensors 270, respectively.

Figure 11A:
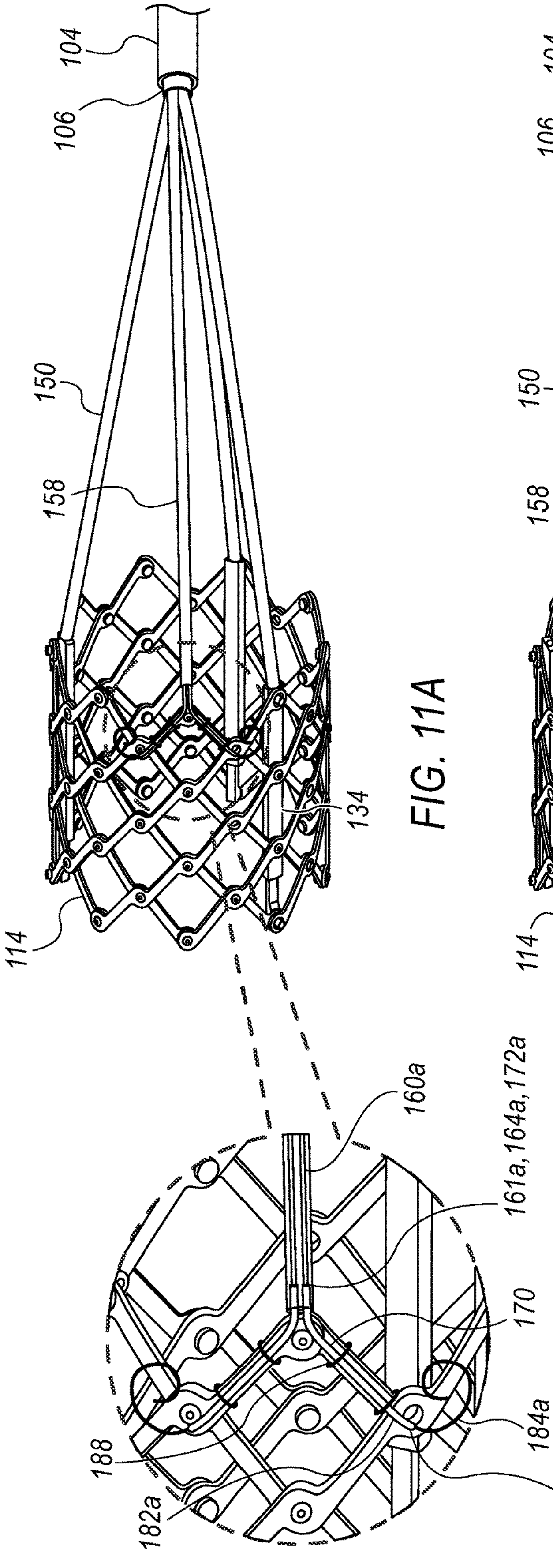
FIGS. 11A-11B show different states of a flex sensing assembly having flexible distal extension extending from the flex sensors, according to some embodiments.
Figure 11B:
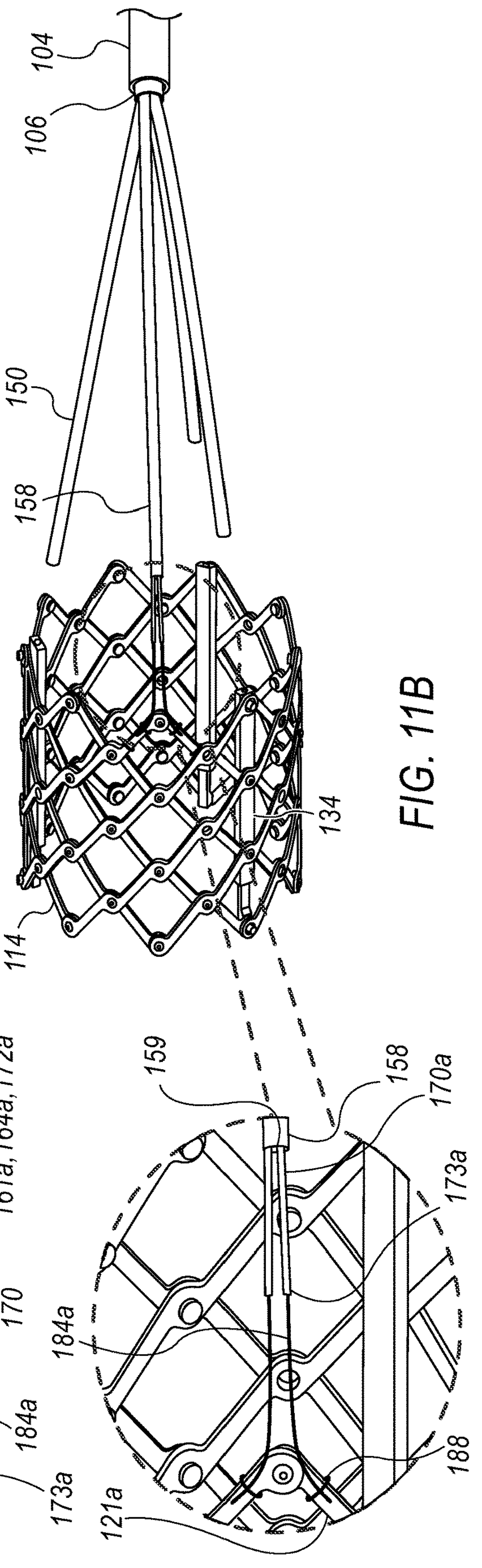

As mentioned above, the flex sensing assembly 156 may be fully detachable from the prosthetic valve 114, to facilitate delivery apparatus 102 retrieval once the valve is fully deployed and mounted in position. FIGS. 11A-B show an exemplary embodiment of a flex sensing assembly 156 equipped with at least one flex sensor 170 coupled to a strut 121. It will be clear that while a configuration of two flex sensors 170 coupled to two intersecting struts 121 is shown, the embodiments are similarly applicable for a single flex sensor 176 (according to the configurations shown in FIGS. 6A-8, for example), or more than two flex sensors. In order to avoid undue clutter from having too many reference numbers and lead lines on a particular drawing, numerals are assigned only to some components in FIGS. 11A-B, for example—only to the first flex sensor 170*a*, first communication channel 160*a*, and so on.

In the illustrated embodiment, each flex sensor 170 is coupled to a respective strut 121 via a plurality of coupling members 188 which are non-affixing coupling members, for example in the form of suture loops or bands 188. The sutures or bands 188 may be tightly wrapped around the flex sensor 170 and the respective strut 121, configured to retain the flex sensor 170 in place over the strut 121 by facilitation frictional forces between the coupling member 188 and the flex sensor 170 and/or the strut 121. The coupling members 188 are configured to allow at least a portion of the flex sensor 170 to slide forward or backward relative to the strut 121 it is coupled to. This may advantageously prevent the flex sensor 170 from over-stretching during valve expansion, for example.

In most cases, it is sufficient to couple the flex sensor 170 to a strut portion 122, between the intersection junction 124 and an adjacent junction, for example—a distal junction along the same strut 121. According to some embodiments, as shown for example in FIG. 5C, the flex sensor 170 comprises a sensor distal portion 182, which is configured to extend beyond the most distal coupling member 188 during the entire valve range of diameters, between the crimped state and the fully expanded state. In such embodiments, the minimal length of sensor distal portion 182 may be defined as the shortest distal portion of the flex sensor 170, extending beyond the most distal coupling member 188, at the valve fully expanded state. In some variants of the embodiments, the minimal length of the sensor distal portion 182 is chosen so as to prevent the flex sensor 170 from slipping out of the most distal coupling member 188 during transition from a crimped state to a fully expanded state of the valve 114.

According to some embodiments, the sensor distal portion 182 may be flexibly curved sideways, away from the axial direction of the strut 121 it is attached to, to provide additional retaining force, preventing spontaneous displacement of the flex sensor 170 relative to the strut 121 it is coupled to. The flexibility of the sensor distal portion 182 allows it to easily slip through the coupling members 188 when a force is applied thereto, for example, during valve expansion.

According to some embodiments, as shown in FIGS. 11A-B, the flex sensing assembly 156 further comprises a flexible distal extension 184, attached to and extending distally from, the flex sensor distal end 173. The flexible distal extension 184 may be provided in the form of a wire, a cable and the like. The minimal length of the flexible distal extension 184 may be chosen to have at least a portion thereof extending beyond the most distal coupling member 188 during transition from a crimped state to a fully expanded state of the valve 114.

According to some embodiments, as shown in FIG. 11A, the flexible distal extension 184 may be resiliently curved sideways, away from the axial direction of the strut 121 the respective flex sensor 170 it is attached to, to provide additional retaining force that prevents spontaneous displacement of the flex sensor 170 relative to the strut 121 it is coupled to. The resiliency and flexibility of the distal extension 184 allows it to easily slip through the coupling members 188 when an axial force is applied thereto, for example, during valve expansion.

Once the desired diameter of the prosthetic valve 114 is reached, the flex sensing assembly 156 may be pulled in a proximally oriented direction, wherein the pull force applied thereto is sufficient to overcome friction forces or any other forces applied by the coupling members 188 to couple the flex sensors 170 to the struts 121. According to some embodiments, the pull force for decoupling the flex sensing assembly 156 from the valve 112 may be applied manually. According to some embodiments, the pull force for decoupling the flex sensing assembly 156 from the valve 114 may be applied by a mechanical or electrical actuation mechanism at the handle 110.

As shown in FIG. 11B, during retraction of the flex sensing assembly 156, the flex sensors 170, along with the distal extensions 184, are pulled through the respective coupling members 188, for example, through the suture loops or bands 188. If the flexible distal extensions 184 are naturally curved, as shown in FIG. 11A, such curves may be easily straightened as the distal extensions 184 are pulled through the coupling members 188, as shown in FIG. 11B. While FIG. 11B illustrates a state in which the actuation assemblies 150 are detached and spaced away from the valve 114$^a$, while at least a portion of the flex sensing assembly 156 (e.g., flexible distal extensions 184), is in the process of detachment and may still partially extend through at least some of the coupling members 188, this is for purpose of illustration only. Decoupling of the flex sensing assembly 156 may be performed prior, during or after detachment of the actuation assemblies 150 (in the case of mechanically expandable valve 114$^a$, for example). According to some embodiments, the handle 110$^a$ comprises a mechanism (not shown) configured to facilitate simultaneous detachment and retraction of both the actuation assemblies 150 and the flex sensing assembly 156, preferably via a single knob operable by an operator or user of the handle 110$^a$.

According to some embodiments, the flex sensor 170 comprises a flexible sensor substrate 176, and a variable resistance element 178. The flexible sensor substrate may extend along the entire length between the flex sensor proximal end 172 and the flex sensor distal end 173, while the variable resistance element 178 may extend along a portion of the flex sensor 170, between the flex sensor proximal end 172 and a position that may be proximal to the flex sensor distal end 173. According to some embodiments, the sensor distal portion 182 comprises a portion of the flexible sensor substrate 176, but is devoid of a variable resistance element 178.

According to some embodiments, the variable resistance element 178 is attached to or embedded in the flexible sensor substrate 176. For example, the flexible sensor substrate 176 may include a silicon or rubber casing, or and the variable resistance element 178 may be molded in the substrate casing 176 to protect it from the corrosive environment inside the vascular system, by sealing it from body fluids. According to some embodiments, the variable resistance element 178 includes terminals or other electrical connectors, configured to electrically connect, at interface 164, with the corresponding communication channel 160.

According to some embodiments, the processing unit at the handle 110 is configured to apply voltage, delivered via the communication channels 160 and through the terminals at interface 164, to the variable resistance elements 178 of the flex sensors 170, and to measure electrical resistance. A relationship between the degree of flex angle (e.g., $\alpha_1$, $\alpha_2$, $\gamma$) and the resistance (or alternatively, the optical signals) can be developed and used in software included in the control unit 111$^a$.

According to some embodiments, the flexible sensor substrate 176 is provided in the form of a polymer sheet or elongated strip, and may include polyamide or any other type of an elastomer.

According to some embodiments, the variable resistance element 178 is provided in the form of a strain gauge or other type of a flexible potentiometer, configured to vary its electrical resistivity in response to the extent of bending applied thereto. Changes in resistivity produce a corresponding changes in voltage that can be processed by the control unit 111$^a$, to determine change in valve diameter.

Figure 12A:
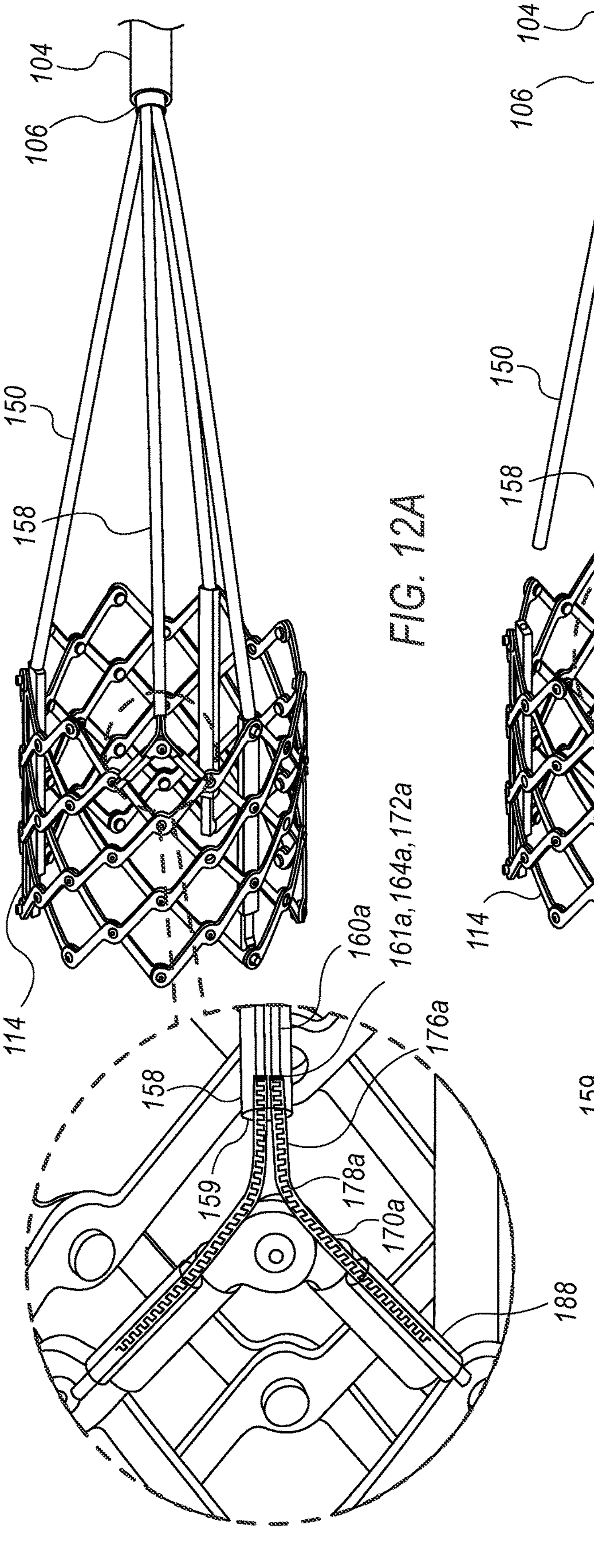
FIGS. 12A-12B show different states of a flex sensing assembly equipped with flex sensors that include strain gauges, according to some embodiments.
Figure 12B:
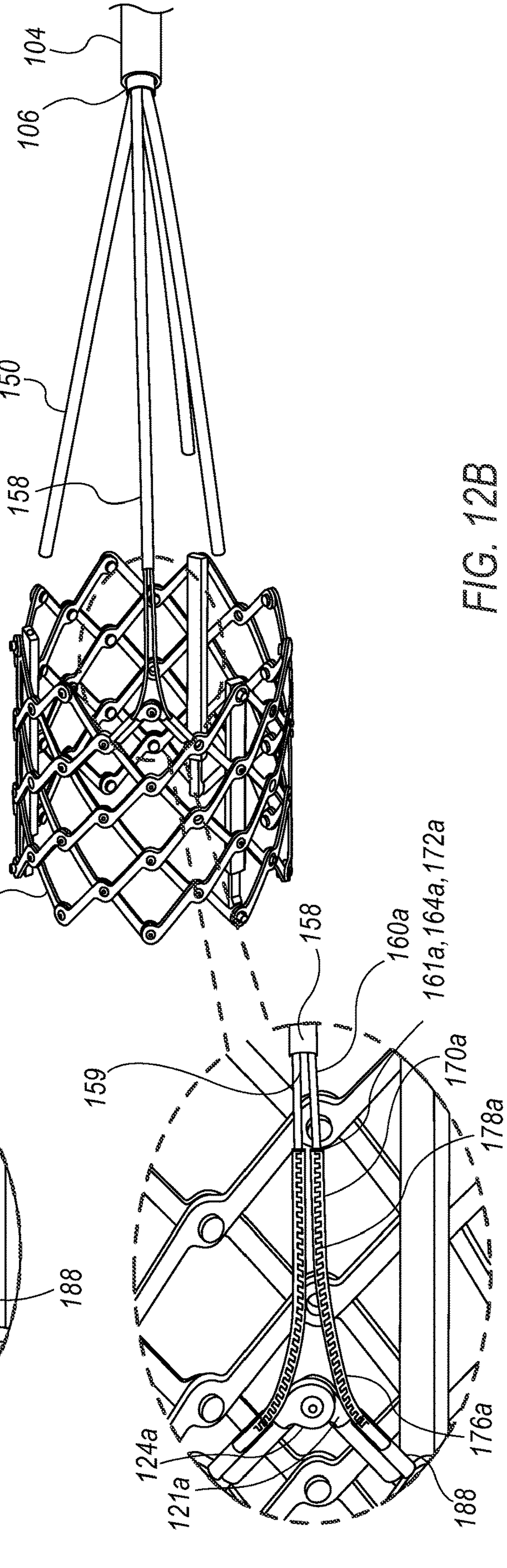

FIGS. 12A-B show an exemplary embodiment of a flex sensor 170 comprising a variable resistance element 178 in the form of a strain gauge, disposed along a portion of the sensor substrate 176. It will be clear that while a configuration of two flex sensors 170 coupled to two intersecting struts 121 is shown, the embodiments are similarly applicable for a single flex sensor 170 (according to the configurations shown in FIGS. 6A-8, for example), or more than two flex sensors. In order to avoid undue clutter from having too many reference numbers and lead lines on a particular drawing, numerals are assigned only to some components in FIGS. 12A-B, for example—only to the first flex sensor 170*a*, first communication channel 160*a*, and so on.

According to some embodiments, the strain gauge 178, as shown in FIGS. 12A-B, is provided with a meandering structure, which may advantageously increase resistance variation under flex thereof.

According to some embodiments, the coupling member 188 may include a tubular member, as shown in FIG. 11A, through which the flex sensor 170 may slide backward and forward. While shown in combination with a flex sensor 170 having a strain gauge 178, it will be clear that this is for illustrative purpose only, and that a tubular coupling member 188 may be employed in combination with any other embodiment of flex sensors disclosed herein.

As shown in FIG. 12B, during retraction of the flex sensing assembly 156, the flex sensors 170 are pulled through the respective coupling members 188, for example, through the tubular members 188. If the sensor distal portions 182 are naturally curved, such curves may be easily straightened as the sensor distal portions 182 are pulled through tubular coupling members 188, as shown in FIG. 12B. While FIG. 12B illustrates a state in which the actuation assemblies 150 are detached and spaced away from the valve 114$^a$, while at least a portion of the flex sensing assembly 156 (e.g., sensor distal portions 182), is in the process of decoupling and may still partially extend through at least a portion of tubular members 188, this is for purpose of illustration only, and decoupling of the flex sensing assembly 156 may be performed prior, during or after detachment of the actuation assemblies 150 (in the case of mechanically expandable valve 114[a], for example).

According to some embodiments, the variable resistance element 178 is provided in the form of a conductive material layer, disposed over at least a portion of the flexible sensor substrate 176 and configured to change its resistance with the degree of flex applied thereto. The conductive material layer can include graphite in combination with a binder. According to some embodiments, the variable resistance element 178 is provided in the form of conductive ink. The material of the variable resistance element 178 may be sprayed, rolled, silk-screened, brushed or otherwise printed onto the flexible sensor substrate 176.

Figure 13A:
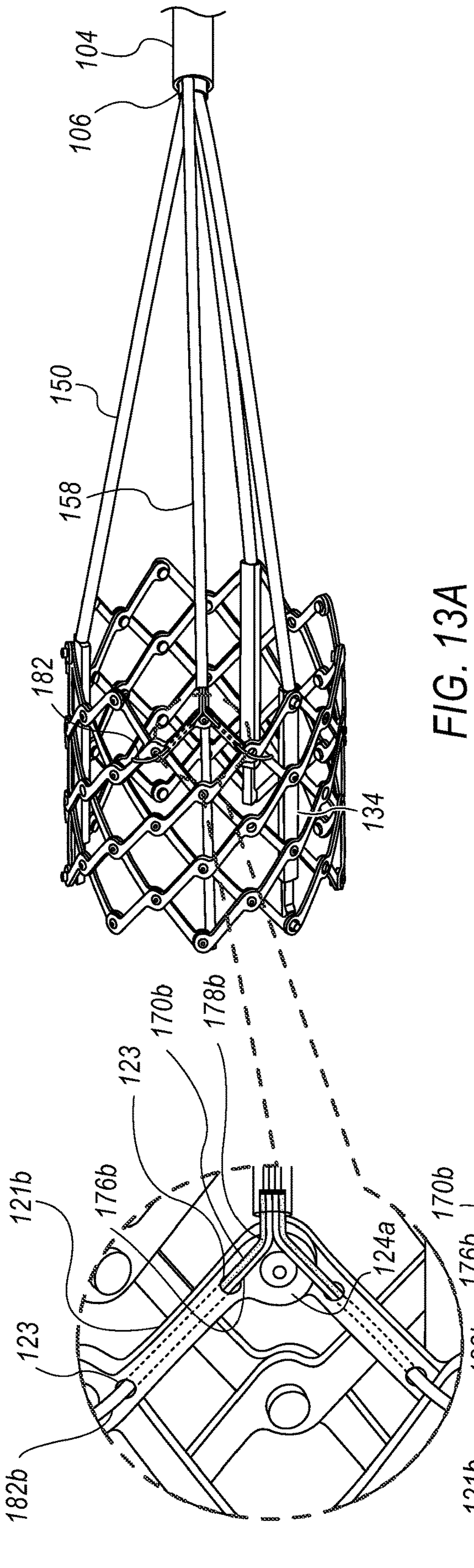
FIGS. 13A-13B show different states of a flex sensing assembly equipped with flex sensors that include conductive material layers, according to some embodiments.
Figure 13B:
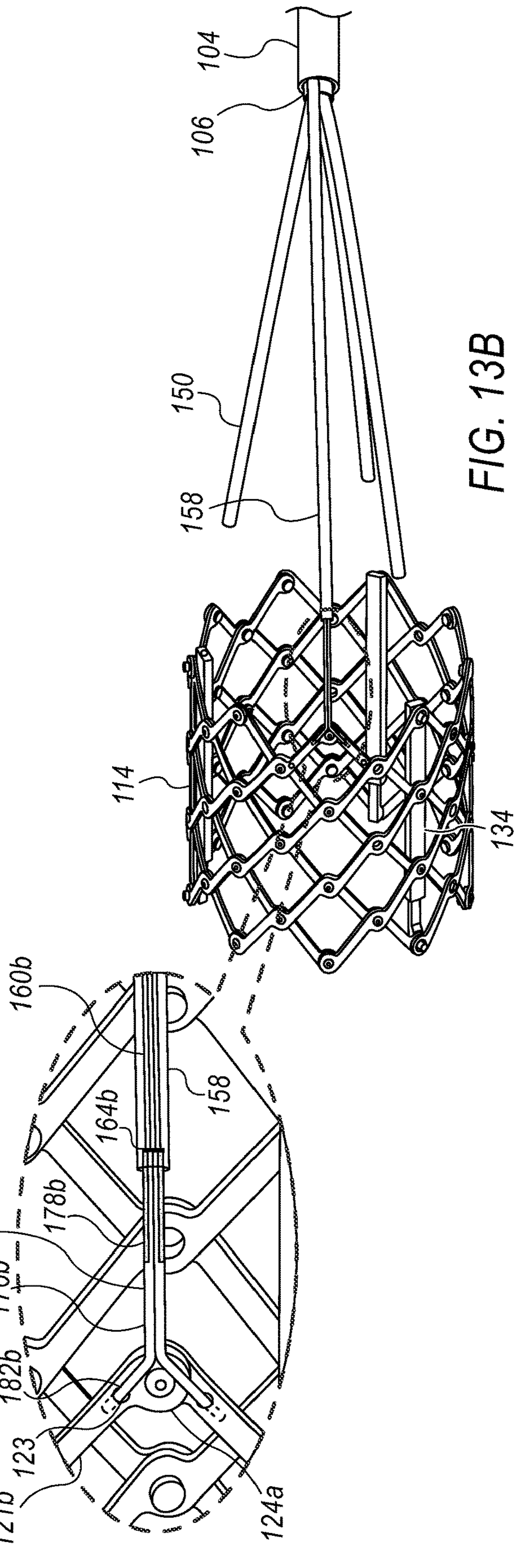

FIGS. 13A-B show an exemplary embodiment of a flex sensor 170 comprising a variable resistance element 178 in the form of a conductive material layer, disposed over a portion of the sensor substrate 176. It will be clear that while a configuration of two flex sensors 170 coupled to two intersecting struts 121 is shown, the embodiments are similarly applicable for a single flex sensor 170 (according to the configurations shown in FIGS. 6A-8, for example), or more than two flex sensors. In order to avoid undue clutter from having too many reference numbers and lead lines on a particular drawing, numerals are assigned only to some components in FIGS. 13A-B, for example—only to the second flex sensor 170*b*, second communication channel 160*b*, and so on.

The conductive material layers 178 may be electrically coupled to the respective communication channels 160 at the interfaces 164, as shown in FIG. 13A.

According to some embodiments, the coupling members 188 are provided as geometrical features integrally formed with components of the prosthetic valve 114. According to some embodiments, as shown in FIG. 11A, the struts 121 configured to interact with the flex sensing assembly 156 are provided with at least one strut aperture 123, and preferably at least two strut apertures 123 formed along each strut 121 to which a flex sensor 170 may be coupled. In the illustrated embodiment, each flex sensor 170 may extend into one strut aperture 123, for example, at a proximal position in the vicinity of the intersection junction 124, and out of a subsequent junction provided along the same strut 121.

In some applications, the strut apertures 123 are through-holes, enabling the flex sensor 170 to extend through each apertures from one side of the strut 121 to the other side, such that at least a portion of the flex sensor 170 is disposed along an inner surface of the strut 121 (i.e., a surface facing radially inward), and at least a portion of the flex sensor 170 is disposed along an outer surface of the strut 121 (i.e., a surface facing radially outward).

In some applications, the strut 121 is provided with an internal channel (not numbered) extending between two strut aperture 123. In such applications, the flex sensor 170 may be inserted into the strut channel through one strut aperture 123, and exit from the channel through another, such that at least a portion of the flex sensor 170 is disposed within the internal strut channel.

While shown in combination with a flex sensor 170 having a conductive material layer 178, it will be clear that this is for illustrative purpose only, and that a struts 121 with strut apertures 123 may be employed in combination with any other embodiment of flex sensors disclosed herein.

As shown in FIG. 13B, during retraction of the flex sensing assembly 156, the flex sensors 170 are pulled through the respective strut apertures 123. If the sensor distal portions 182 are naturally curved, such curves may be easily straightened as the sensor distal portions 182 are pulled through strut apertures 123. While FIG. 13B illustrates a state in which the actuation assemblies 150 are detached and spaced away from the valve 114, while at least a portion of the flex sensing assembly 156 (e.g., sensor distal portions 182), is in the process of decoupling and may still partially extend through at least some of the strut apertures 123, this is for purpose of illustration only, and decoupling of the flex sensing assembly 156 may be performed prior, during or after detachment of the actuation assemblies 150 (in the case of mechanically expandable valve 114[a], for example).

According to some embodiments, the flex sensing assembly 156 further comprises a flexible elongated member 186, extending distally from the handle 110 to the flexible distal extension 184, configured to couple at least two flexible distal extension 184 to each other, and to allow separation thereof upon being pulled in a proximally oriented direction 14.

FIGS. 14A-E shows different stages of utilizing a flex sensing assembly 156 equipped with a flexible elongated member 186, according to some embodiments. The flex sensing assembly 156 comprises two flexible distal extensions 184, which are similar in structure and function to the flexible distal extensions 184 described in conjunction with FIGS. 11A-B, except that each flexible distal extension 184 may further include a distal loop 185. The first distal loop 185*a* of the first flexible distal extensions 184*a* may be engaged with the second distal loop 185*b* of the second flexible distal extensions 184*b*, respectively, by the flexible elongated member 186 extending through both.

The flexible elongated member 186 may be provided as a flexible string, suture, wire, cable, and the like, and may extend through the delivery shaft 106, through the sensor shaft 158, and/or through another dedicated shaft (not shown).

Figure 14A:
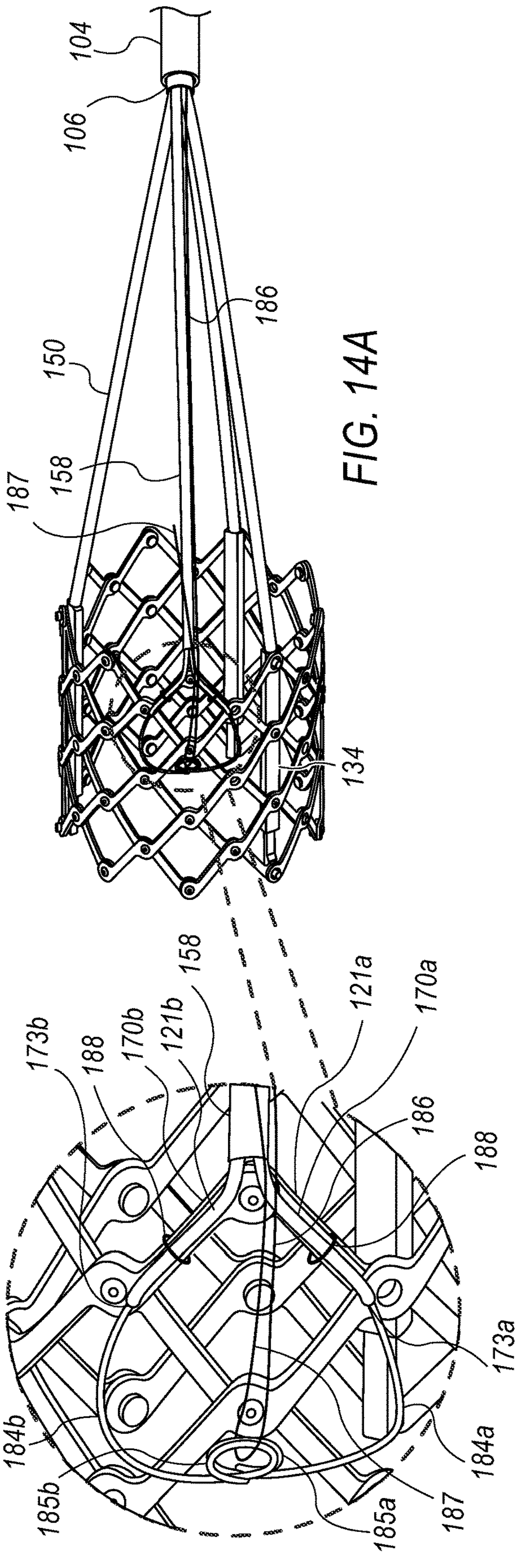
FIGS. 14A-E shows different stages of utilizing a flex sensing assembly equipped with a flexible elongated member, according to some embodiments.

In a first stage shown in FIG. 14A, the flexible elongated member 186 extends through the open space contoured by each of the first distal loop 185*a* and second distal loop 185*b*, which may be aligned with each other. The flexible elongated member 186 may extend distally from the handle 110 to the distal loops 185, and bend over through the loops 185, having a flexible member end portion 187 extending proximally therefrom.

Figure 14B:
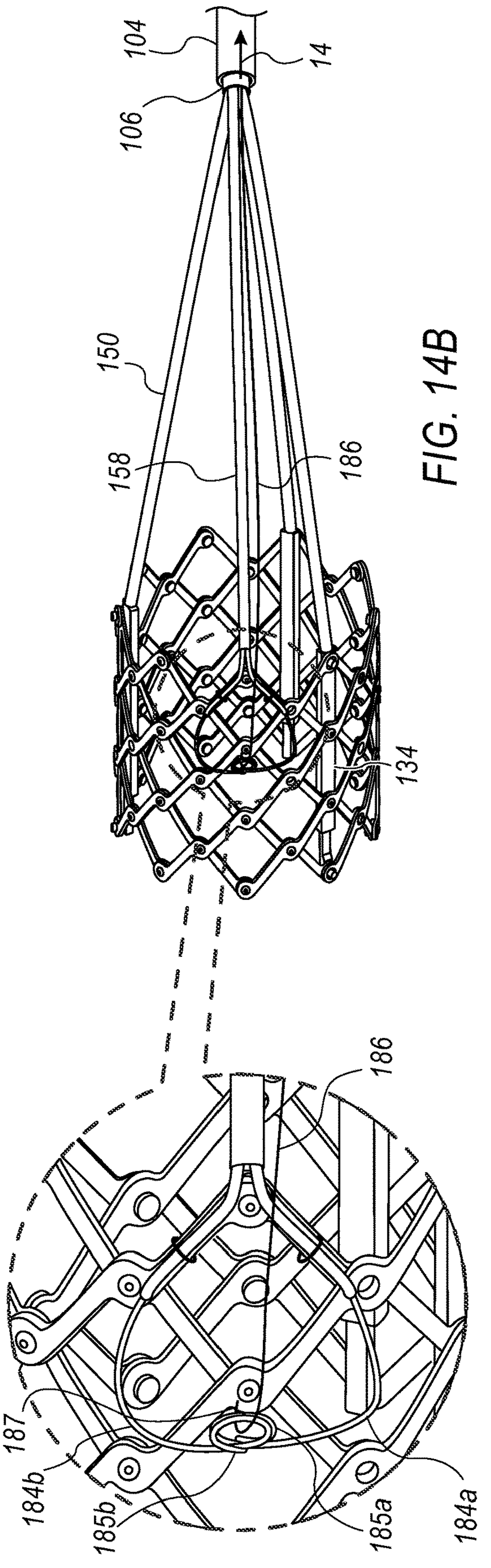

In order to initiate retraction of the flex sensing assembly 156, the flexible elongated member 186 may be pulled in a proximally oriented direction, as shown in FIG. 14B, such that the bent over flexible member end portion 187 becomes shorter, until it is fully withdrawn from the loops 185. The handle 110 may include a controllable mechanism for pulling the flexible elongated member 186.

Figure 14C:
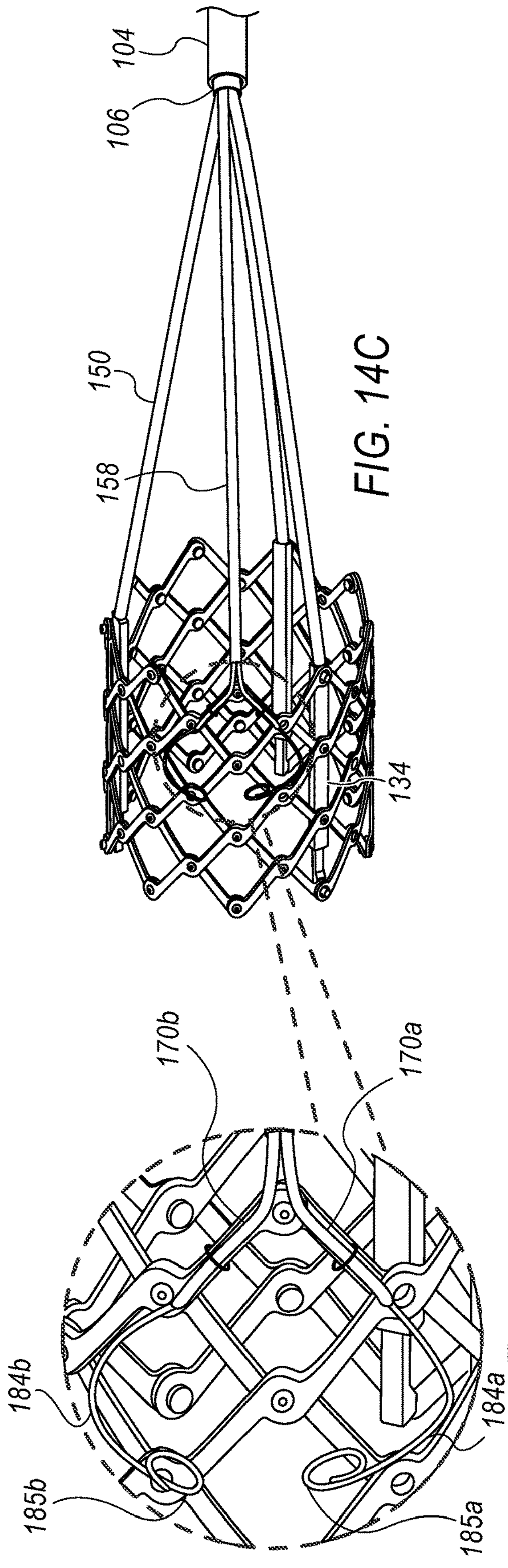
Figure 14D:
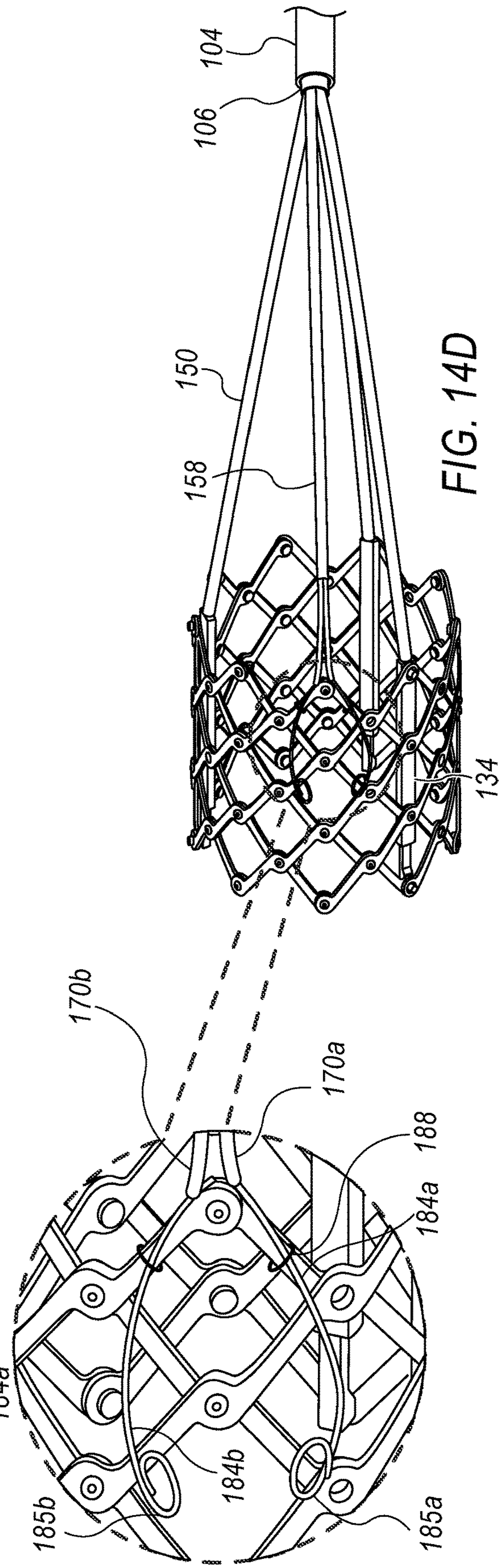
Figure 14E:
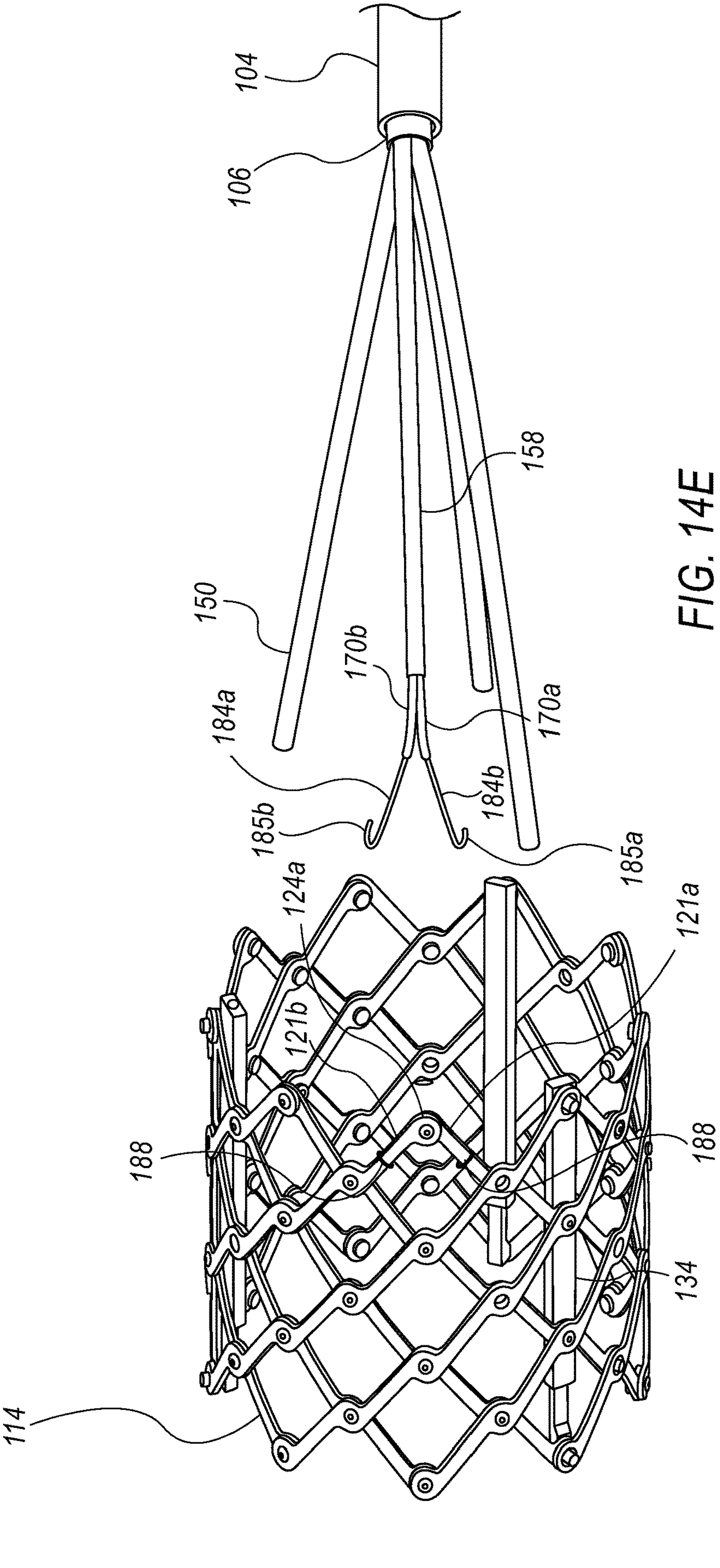

As shown in FIG. 14C, once the flexible elongated member 186 is completely withdrawn, the first distal loop 185*a* and the second distal loop 185*b* are no longer coupled to each other, allowing the flex sensors 170 to be retracted, along with the distal extensions 184. A flex sensing assembly 156 equipped with a flexible elongated member 186 may be utilized in combination with coupling members 188 according to any of the previous embodiments. FIG. 14E shows both the actuation arm assemblies 150 and the flex sensing assembly 156, detached and spaced away from the prosthetic valve 114.

According to some embodiments, the distal loops 185 are open-ended loops, formed by pre-shaping the end portions of the distal extensions 184 to resiliently form a loop-shaped configuration, while the end of the distal extensions 184 remain free ended (i.e., unconnected to other regions thereof). Open-ended distal loops 185 (as shown in FIGS. 14A-E) may be easily straightened, as the distal extensions 184 are pulled through coupling members 188, such as suture loops or bands 188. According to alternative embodiments, the distal loops 185 are close-ended loops (not shown), which are flexible enough to be able to contract while being pulled through coupling members 188, such as suture loops or bands 188.

An advantage conferred by the delivery assemblies and the methods disclosed herein, is that they enable continuous real-time diameter monitoring, thereby providing valuable feedback to the clinician with respect to the valve expansion within the native anatomy. This valuable information may assist in preventing, or at least reducing, potential trauma to a tissue (e.g., the annulus). The clinician can continuously readjust the diameter of the prosthetic valve 114 as necessary, until the prosthetic valve 114 is expanded to a diameter that best fits the native annulus. For example, a diameter which is sufficient to anchor the prosthetic valve 114 in place against the surrounding tissue, with little or no paravalvular leakage, and without over-expanding the prosthetic valve 114 so as to avoid, or reduce the risk of, native annulus rupture.

A prosthetic valve 114 of the current disclosure may include any prosthetic valve configured to be mounted within the native aortic valve, the native mitral valve, the native pulmonary valve, and the native tricuspid valve. While a delivery assembly 100 described in the current disclosure, includes a delivery apparatus 102 equipped with a flex sensing mechanism 156 and a prosthetic valve 114, it should be understood that the delivery apparatus 102 equipped with a flex sensing mechanism 156 according to any embodiment of the current disclosure can be used for implantation of other prosthetic devices aside from prosthetic valves, such as stents or grafts.

While the embodiments are described and illustrated throughout FIGS. 1-14E for use with a mechanically expandable valve $114^a$, it will be clear that flex sensing assemblies 156 according to any of the embodiments disclosed herein may be similarly used in combination with other valve types, such as balloon expandable valves or self-expandable valves. However, conventional balloon-expandable valves and self-expandable valves are typically inflated or expanded during a short time period (e.g., in a burst), in a manner which provides limited control of valve expansion. In contrast, utilization of flex sensing assemblies 156 in combination with mechanically expendable valves $114^a$ is advantageous since the mechanical expansion mechanism (for example—as described in conjunction with FIGS. 4A-C) provides a higher degree of control over the rate and extent of valve expansion, enabling the clinician to adjust expansion diameter, responsive to real-time feedback provided by the flex sensing assembly 156.

Recently, balloon expandable valves that can be expanded within a range of functional sizes have been developed, such as disclosed in U.S. Patent Application Publication No. 2018/0028310, which is incorporated herein by reference. For the implantation of such prosthetic valves, the physician conventionally selects an appropriate volume of the inflation fluid corresponding to a selected prosthetic valve diameter from a range of fill volumes. Using a conventional inflation syringe, it can be difficult for the physician to draw the precise amount of inflation fluid into the syringe that is required to expand a prosthetic valve to a desired size if the required volume does not correspond with one of the volume indicators provided on the syringe. Moreover, the amount of inflation fluid is not necessarily correlated with a specific expansion diameter, as the balloon may extend longitudinally as well as expand diametrically, making it hard to predict radial expansion based solely on a known amount of fluid inflation. Thus, the valve expansion mechanism is herein modified to allow more controlled inflation methods.

Additionally, in order to take advantage of any of the flex sensing assemblies described hereinabove in conjunction with FIGS. 5A-14E, for use with balloon expandable valves, the expansion mechanism is herein modified to allow the balloon to be inflated and/or deflated in a gradual and controllable manner, thereby allowing the clinician to adjust balloon inflation according to the measured expansion diameter.

Figure 15:
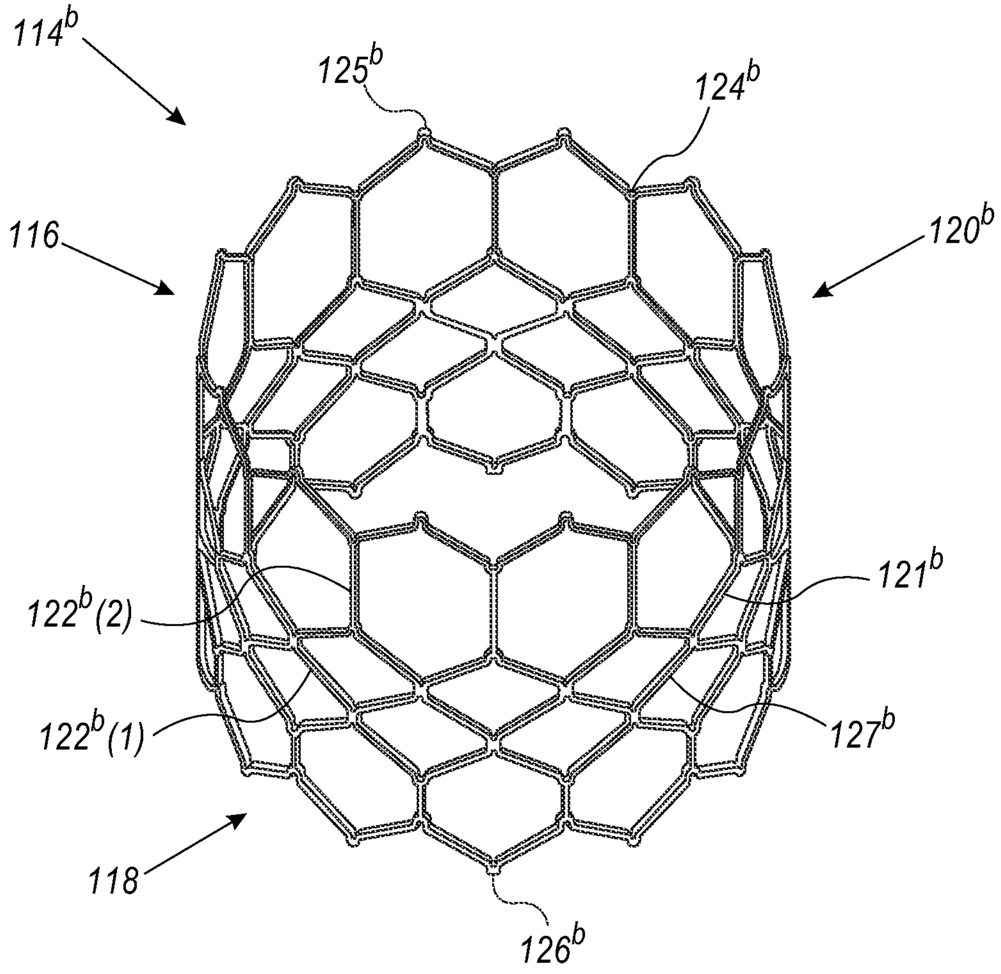
FIG. 15 shows a view in perspective of a frame of a balloon expandable valve, according to some embodiments.

FIG. 15 shows an example of a frame $120^b$ of a balloon expandable valve $114^b$. The frame $120^b$ comprises a plurality of struts $121^b$ that can include angled strut portions $122^b$(1) and vertical strut portions $122^b$(2). In such embodiments, the struts $121^b$ may be pivotable or bendable relative to each other, so as to permit frame expansion or compression. For example, the frame $120^b$ can be formed from a single piece of material, such as a metal tube, via various processes such as, but not limited to, laser cutting, electroforming, and/or physical vapor deposition, while retaining the ability to collapse/expand radially in the absence of hinges and like.

Figure 16:
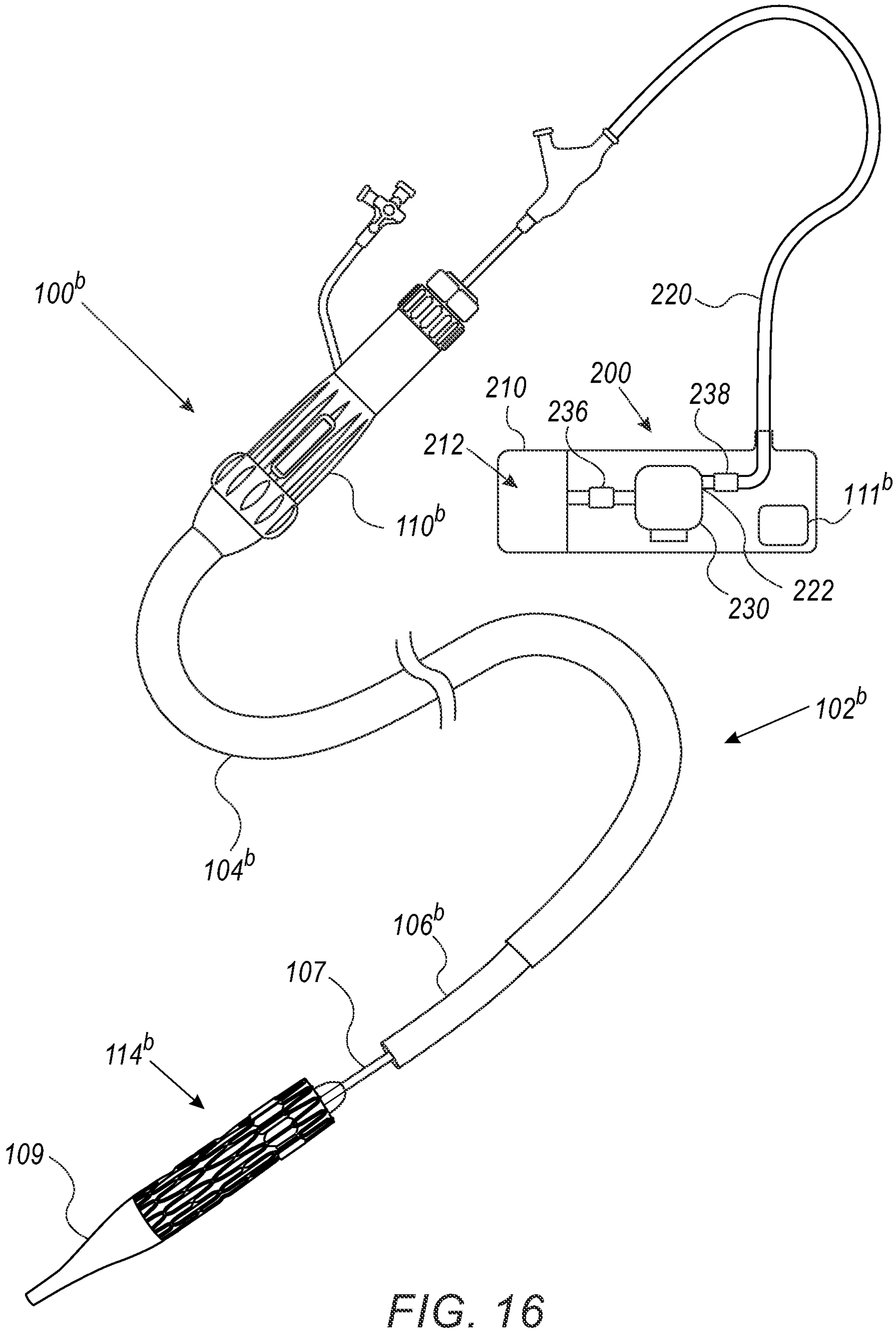
FIG. 16 shows a view in perspective of a delivery assembly for delivery and implantation of a balloon expandable valve, according to some embodiments.
Figure 17A:
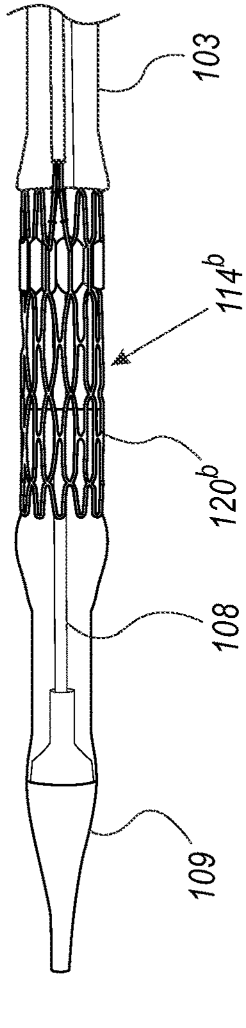
FIGS. 17A-17B show different configurations of the balloon expandable valve of FIG. 16.

FIG. 16 shows an example of a delivery assembly $100^b$ comprising a delivery apparatus $102^b$ for delivery and implantation of balloon expandable valve $114^b$. According to some embodiments, the delivery apparatus $102^b$ includes a balloon catheter 107 having an inflatable balloon 105 (shown, for example, in an inflated state in FIG. 17B) mounted on its distal end. The balloon expandable prosthetic valve $114^b$ can be carried in a crimped state over the inflatable balloon 105, as shown in FIG. 17A. The delivery apparatus $102^b$ can include a delivery shaft $106^b$ and/or an outer shaft $104^b$ that in some cases, can concentrically extend over the balloon catheter 107. The delivery apparatus $102^b$ can additionally include a nosecone 109 attached to a distal end of a nosecone shaft 108, and a distal end of the inflatable balloon 105 can extend over the nosecone 109.

The proximal ends of the balloon catheter 107, and when present—the delivery shaft $106^b$ and/or the outer shaft $104^b$, can be coupled to the handle $110^b$. During delivery of the prosthetic valve $114^b$, the handle $110^b$ can be maneuvered by an operator (e.g., a clinician or a surgeon) to axially advance or retract components of the delivery apparatus $102^b$, such as the nosecone shaft 108, the balloon catheter 107, the delivery shaft $106^b$ and/or the outer shaft $104^b$, through the patient's vasculature, as well as to inflate the balloon 105 mounted on the balloon catheter 107, so as to expand the prosthetic valve $114^b$, and to deflate the balloon and retract the delivery apparatus $102^b$ once the prosthetic valve $114^b$ is mounted in the implantation site.

According to some embodiments, the delivery assembly $100^b$ further comprises an inflation fluid system 200. The inflation fluid system 200 can comprise: a reservoir 210 that can contain a predetermined volume of inflation fluid 212; a fluid flow channel 220 defined between a proximal end 222 and a distal end 224; and a pump 230. Distal end 224 can be in fluid communication with an inlet port 225 of the balloon 105. The inlet port 225 of the balloon 105 can be located at the proximal end thereof. The inflation fluid 212 can be liquid, and can further comprise saline.

The term "fluid communication", as used herein, means that fluid can flow between components in fluid communication with each other. The fluid communication can be accomplished via a direct connection between openings of the respective components or via additional components connected therebetween.

According to some embodiments, the pump 230 can be in fluid communication with both the reservoir 210 and the proximal end 222 of the fluid flow channel 220. A control input of the pump 230 can be in communication with a control unit 111$^b$. Control unit 111$^b$ can be positioned within the inflation fluid system 200, within the handle 110$^b$ or at any other suitable location. According to some embodiments, control unit 111$^b$ can comprises a plurality of components, with some of the components being positioned within the inflation fluid system 200, some of the components being positioned within the handle 110$^b$ and/or some of the components being positioned in other suitable locations.

Control unit 111$^b$ can include a central processing unit (CPU), a microprocessor, a microcomputer, a programmable logic controller, an application-specific integrated circuit (ASIC) and/or a field-programmable gate array (FPGA), without limitation. According to some embodiments, the control unit 111$^b$ can further comprise a memory. According to some embodiments, selected data, such as raw signal data or calculated data, may be stored in the memory. According to some embodiments, the control unit 111$^b$ can be configured to log data during the implantation procedure in the memory. According to some embodiments, the control unit 111$^b$ can be configured to transmit to a remote device, logged data from the memory, and/or real-time data.

According to some embodiments, a flow meter 236 and/or a pressure sensor 238 is provided. The flow meter 236 can be coupled between the pump 230 and the reservoir 210, as shown. The pressure sensor 238 can be coupled between the pump 230 and the balloon 105, as shown. Although the pressure sensor 238 is illustrated as being near pump 230, this is not meant to be limiting in any way, and the pressure sensor 238 can be positioned anywhere along the fluid path, including within the balloon 105. Each of the flow meter 236 and the pressure sensor 238 can be in communication with control unit 111$^b$. The control unit 111$^b$ can control the pump 230 to adjust the flow of the inflation fluid 212. Adjustment of the flow of the inflation fluid 212 can include adjustment of the flow rate and/or the amount of inflation fluid 212 that flows into the balloon 105.

The flow adjustment of control unit 111$^b$ can be responsive to a user input, such as the amount of inflation fluid 212 to be injected into the balloon 105. Additionally, or alternately, the flow adjustment of control unit 111$^b$ can be responsive to the flow meter 236 and/or the pressure sensor 238, such that the flow of the inflation fluid 212 remains within predetermined parameters. Additionally, or alternately, the flow adjustment of control unit 111$^b$ can be responsive to additional sensors coupled to the valve and/or balloon, as will be described below. According to some embodiments, the control unit 111$^b$ can further control the pump 230 to reverse the flow of the inflation fluid 212, thereby removing some, or all, of the inflation fluid 212 from the balloon 105.

According to some embodiments, the pressure sensor 238 measures the pressure of the inflation fluid 212 flowing into the balloon 105. The pressure sensor 238 can comprise dedicated circuitry for operation and/or for pressure measurement. Alternatively, or additionally, the pressure sensor 238 can be operated in cooperation with the control unit 111$^b$. The measurement can be performed while the inflation fluid 212 is flowing into the balloon 105 and/or when the control unit 111$^b$ controls the pump 230 to cease the flow of the inflation fluid 212. Control unit 111$^b$ can compare the measured pressure of the inflation fluid 212 to a predetermined maximum pressure threshold value.

According to some embodiments, the control unit 111$^b$ can be configured to control the pump 230 to adjust the flow of the inflation fluid 212 responsive to an outcome of the comparison. Responsive to the measured pressure being greater than the predetermined maximum pressure threshold value, the control unit 111$^b$ can control the pump 230 to cease the flow of the inflation fluid 212 and/or control the pump 230 to reverse the flow of the inflation fluid 212 thereby reducing the pressure. The measured pressure can be output at a user display and the control unit 111$^b$ can be configured to adjust the flow of the inflation fluid responsive to a respective user input.

According to some embodiments, the control unit 111$^b$ can compare the measured pressure to a predetermined minimum pressure threshold value. According to some embodiments, the predetermined minimum pressure threshold value can be substantially the same of the predetermined maximum pressure threshold value. The control unit 111$^b$ can be configured to control the pump 230 to adjust the flow of the inflation fluid 212 responsive to an outcome of the comparison. Responsive to the measured pressure being less than the predetermined minimum pressure threshold value, the control unit 111$^b$ can control the pump 230 to increase the flow rate of the inflation fluid 212, and/or the amount of inflation fluid 212 flowing into the balloon 105, thereby increasing the pressure.

Expansion of the valve 114$^b$ against the surrounding tissue may pose a variety of risks associated with a mismatch between the valve's expansion diameter and the surrounding tissue. One complication is related to valve over-expansion, which may exert excessive radial forces on the surrounding anatomy, resulting in potential damage to the tissue or even annular rupture. On the other hand, valve under-expansion might increase the risk of aortic valve or mitral valve regurgitation. Inappropriate expansion may also result in unfavorable hemodynamic performance across the valve 114$^b$, such as increased pressure gradients or flow disturbances resulting from diameter mismatch, which may be associated with increased risk of thrombus formations.

Advantageously, the control unit 111$^b$, in cooperation with the pressure sensor 238, can monitor the pressure of the inflation fluid 212, which exhibits a direct relationship to the radial forces on the surrounding tissue, and control the pump 230 to maintain the pressure within a desired predetermined range. This can avoid the deleterious effects of annular rupture, inferior hemodynamic performance and valve regurgitation, arising due to either over-expansion or under-expansion, respectively, of the valve 114$^b$.

FIG. 17A shows the valve 114$^b$ mounted on the balloon catheter 107 in a crimped configuration for delivery into the body. The balloon catheter 107 comprises the inflatable balloon 105 for expanding the valve within the patient's body, the crimped valve 114$^b$ being positioned over the deflated balloon 105 during delivery. According to some embodiments, the delivery apparatus 102$^b$ further comprises a pusher 103 that can be used to facilitate passage of the valve 114$^b$ through a shaft (e.g., an outer shaft 104$^b$) of the delivery assembly 100$^b$.

Figure 17B:
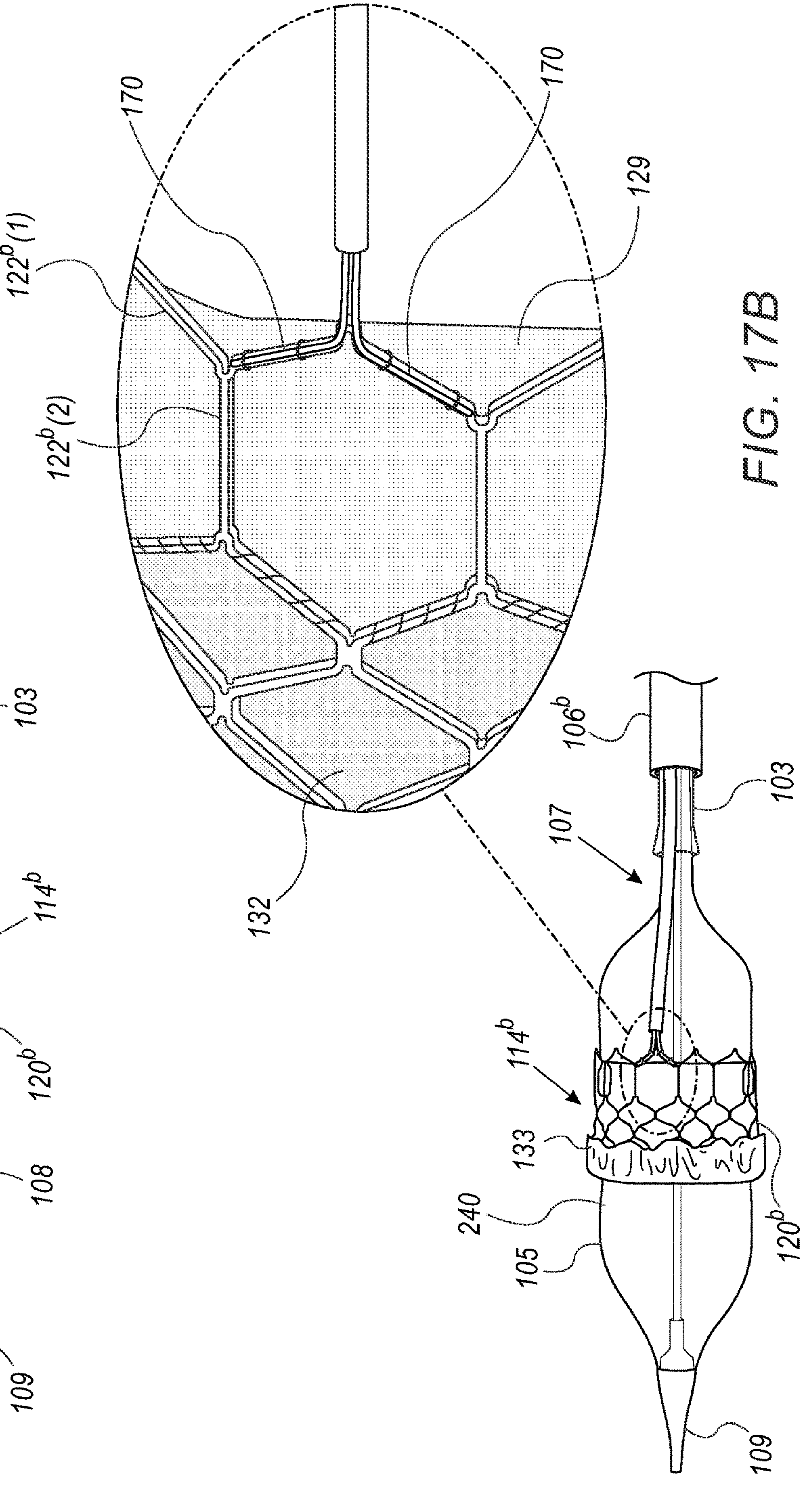

FIG. 17B shows the balloon 105 in an inflated state, causing the prosthetic valve 114$^b$ to radially expand into contact with the surrounding anatomy (e.g., into contact with the aortic annulus, in the case of aortic valve replacement procedures). The balloon catheter 107 is shown protruding through the pusher 103 and the valve 114$^b$. In some occasions, the frame 120$^b$ may be slightly over-expanded to account for any spring-back in the material. The pusher 103 can be utilized to push the frame 120 over the balloon 105 in configurations in which the crimped balloon is positioned proximal to the balloon during delivery to the implantation site, for example to reduce overall crimp profile during such delivery through the patient's vasculature.

Once the valve 114$^b$ is fully expanded, the balloon 105 is deflated and remove along with the remainder of the delivery apparatus 102$^b$. Because the frame 120$^b$ is plastically-deformable, it substantially retains its expanded state. According to some embodiments, the balloon 105 can be deflated by control unit 111$^b$ controlling the pump 230 to reverse the flow of the inflation fluid 212 thereby emptying the balloon 105 of the inflation fluid 212. Furthermore, the control unit 111$^b$ can control the pump 230 to remove only a portion of the inflation fluid 212 from within the balloon 105, as will be described below.

According to some embodiments, at least one diameter sensor is provided. The output of the at least one diameter sensor is responsive to the radial diameter of the inflatable balloon 105 and/or the frame 120$^b$. The control unit 111$^b$ is in communication with the at least one diameter sensor and can determine an indication of the radial diameter of the inflatable balloon 105 and/or the frame 120$^b$, as described below. As described below, the indication of the radial diameter can comprise the difference between an initial radial diameter and a present radial diameter. The term "initial radial diameter", as used herein, means the radial diameter of the inflatable balloon 105 and/or frame 120$^b$ at a predetermined time. The term "present radial diameter", as used herein, means the radial diameter of the inflatable balloon 105 and/or frame 120$^b$ measured for performing the comparison to the initial radial diameter. Therefore, the indication of the radial diameter can comprise a change in the radial diameter over a plurality of measurements. According to some embodiments, the at least one diameter sensor can comprise, as described below: at least one flex sensor; at least one radially translatable member and a linear displacement sensor; and/or a strain gauge.

According to some embodiments, at least one flex sensor 170 is provided, the at least one flex sensor 170 coupled to at least one strut of the frame 120$^b$. According to some embodiments, at least a pair of flex sensors 170 are provided, a first of the pair of flex sensors 170 coupled to a first strut of the frame 120$^b$ and a second of the pair of flex sensor 170 coupled to a second strut of the frame 120$^b$, the first and second struts intersecting each other. As described above, control unit 111$^b$ can monitor the output of the at least one flex sensor 170 to determine how much the at least one flex sensor 170 has been flexed. From this information, the control unit 111$^b$ can determine the opening angle of the at least one strut and can further determine the radial diameter of the frame 120$^b$ when expanded, as described above.

According to some embodiments, at least one radially translatable member is provided, juxtaposed with an outer surface 240 of the balloon 105. The at least one radially translatable member can comprise one or more sutures, strings, wires and/or other flexible, inelastic members configured to have sufficient rigidity such that the members do not bend, buckle, or stretch or compress axially when a proximal or distal force is applied thereto during normal use.

Figure 18A:
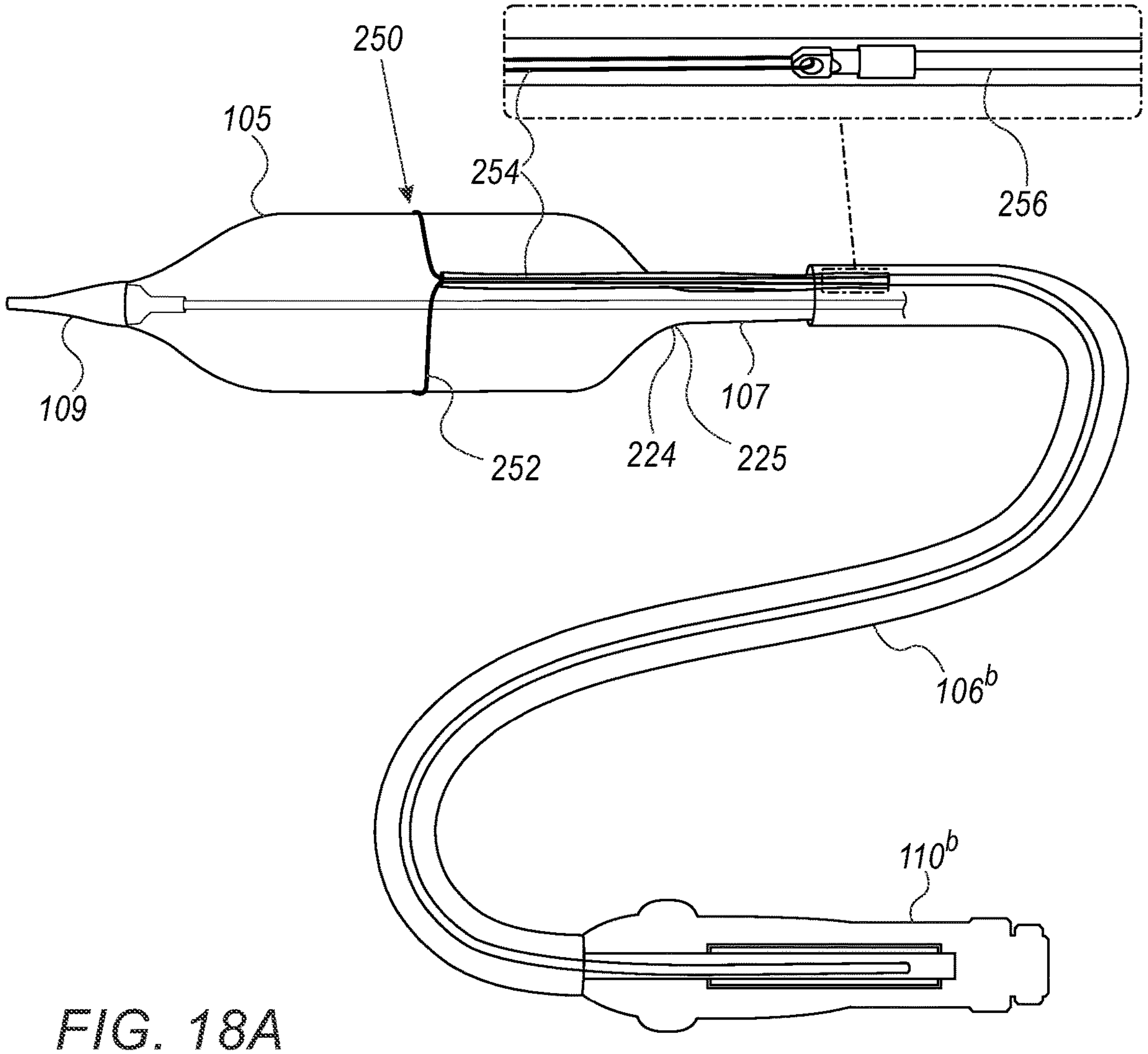
FIGS. 18A-18B show a side view of a first embodiment of a radially translatable member coupled to a linear displacement sensor.

FIG. 18A shows the balloon 105 in an inflated state, and further shows a radially translatable member 250 comprising a loop shaped balloon portion 252 and a connection portion 254. For ease of illustration and explanation, prosthetic valve 114$^b$ is not shown in FIG. 18A, but would be positioned around the balloon 105. The balloon portion 252 surrounds the outer surface 240 of the balloon 105 and the connection portion 254 extends from the balloon portion 252 and is coupled to an input of a linear displacement sensor 260, shown in FIG. 18B. An output of the linear displacement sensor 260 is in communication with control unit 111$^b$. The coupling of connection portion 254 to linear displacement sensor does not have to be direct. According to some embodiments, connection portion 254 is connected to a cable 256, cable 256 being connected to the input of linear displacement sensor 260. As shown, cable 256 can be coupled to the linear displacement sensor 260.

Figure 18B:
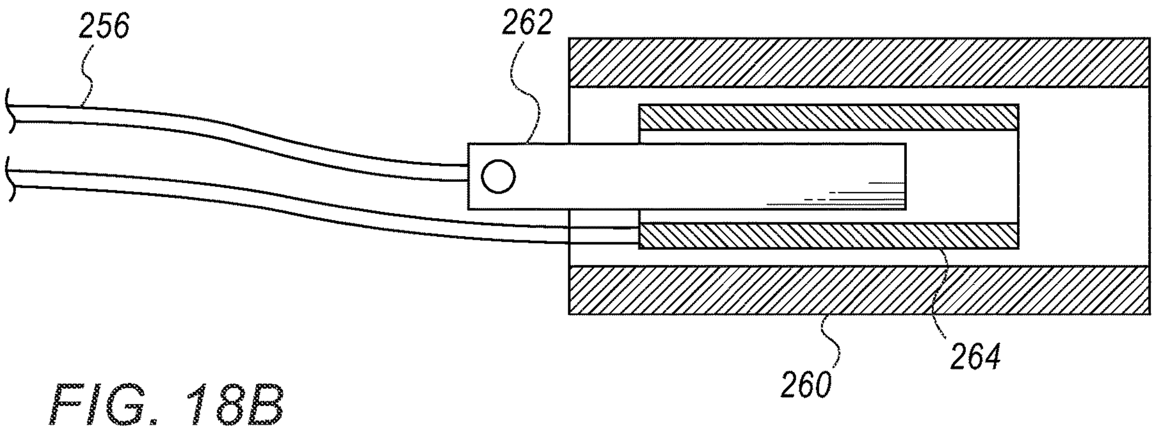

As shown in FIG. 18B, the linear displacement sensor 260 can be implemented using a linear variable differential transformer (LVDT) sensor, which can comprise a transformer core 262 within a tube 264, as known to those skilled in the art. The tube can support the coils (not shown) of the LVDT. Cable 256, or connection portion 254, can be coupled to the core 262 or the tube 264, to generate relative motion between core 262 and tube 264. Core 262 can further be in electrical communication with control unit 111$^b$ (not shown). Alternatively, or additionally, the linear displacement sensor 260 can be implemented using a potentiometer, as known to those skilled in the art.

The linear displacement sensor 260 can comprise dedicated circuitry for the operation thereof and/or to determine the amount of relative motion applied thereto. Alternatively, or additionally, the control unit 111$^b$ can operate the linear displacement sensor 260 and/or to determine the amount of relative motion applied thereto. The connection portion 254 can be inserted through an aperture at an end of cable 256. The linear displacement sensor 260 can be positioned within the inflation fluid system 200, within the handle 110$^b$ or within any other suitable location.

Figure 19:
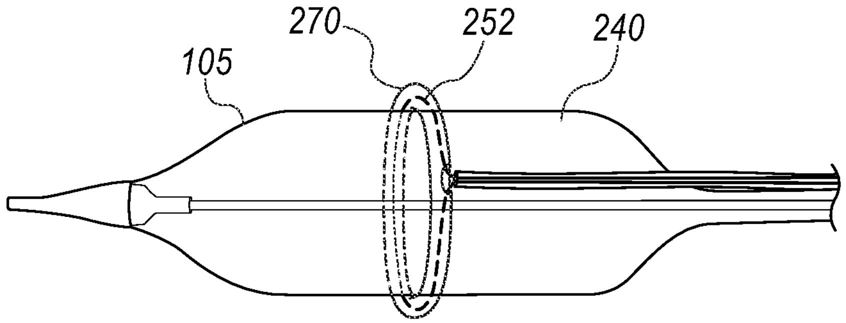
FIG. 19 shows a side view of the first embodiment of the radially translatable member of FIGS. 18A-18B positioned within a sleeve.

FIG. 19 shows the balloon 105 in an inflated state, where the balloon portion 252 of the radially translatable member 250 surrounds the outer surface 240 of the balloon 105. For ease of illustration and explanation, prosthetic valve 114$^b$ is not shown in FIGS. 19-20, but would be positioned around the balloon 105. The balloon portion 252 can be positioned within a sleeve, which can be a stand-alone sleeve, such as the illustrated circumferential sleeve 270. The circumferential sleeve 270 can be disposed around the outer surface 240 of the balloon 105 and can attached thereto by gluing, suturing, or other suitable attachment mechanism. Alternatively, circumferential sleeve 270 can be an integral part of the outer surface 240 of the balloon 105. Circumferential sleeve 270 can support the balloon portion 252 so as to maintain a generally fixed position of the balloon portion 252 in relation to the balloon 105.

Figure 20:
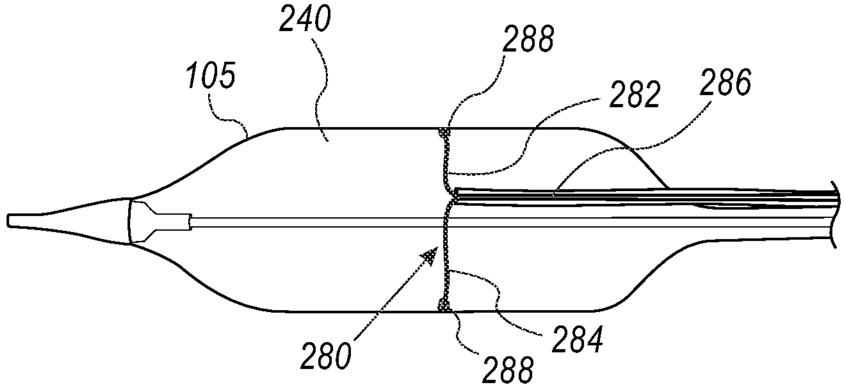
FIG. 20 shows a side view of a second embodiment of a radially translatable member.

FIG. 20 shows the balloon 105 in an inflated state, with a radially translatable member 280 juxtaposed with the outer surface 240 of the balloon 105. According to some embodiments, radially translatable member 280 comprises: a first balloon portion 282; a second balloon portion 284; and a connection portion 286. Each of the first balloon portion 282 and the second balloon portion 284 extends from the connection portion 286. As described above, first balloon portion 282 and/or second balloon portion 284 can be positioned within a sleeve, such as sleeve 270. The connection portion 286 can be inserted through the rod 256 (not shown in FIG. 20).

According to some embodiments, each of the first balloon portion 282 and the second balloon portion 284 extends in a respective direction, the direction of extension of the second balloon portion 284 generally opposing the direction of extension of the first balloon portion 282. Particularly, when looking towards nosecone 109, the first balloon portion 282 can extend radially about the outer surface 240 of the balloon 105 in a generally clockwise direction and the second balloon portion 284 can extend radially about the outer surface 240 of the balloon 105 in a generally counterclockwise direction, or vice versa.

According to some embodiments, each of the first balloon portion 282 and the second balloon portion 284 exhibits a respective distal end 288. Each respective distal end 288 can be secured to the outer surface 240 of the balloon 105, such as by being glued thereto. According to some embodiments, the connection portion 286 can be a single element connecting the first balloon portion 282 to the second balloon portion 284. Alternatively, the connection portion 286 comprises a pair of elements, each of the pair of elements connected to a respective one of the first balloon portion 282 and the second balloon portion 284. As described above in relation to the connection portion 254 of the radially translatable member 250, the connection portion 286 can be coupled to the linear displacement sensor 260.

As the balloon 105 expands, the radially translatable member is radially translated by the radial expansion of the balloon and as a result the respective connection portion is linearly translated. For example, the expansion of the balloon 105 moves the balloon portion 252 of the radially translatable member 250 radially and as a result the connection portion 254 is pulled linearly. In another example, the expansion of the balloon 105 moves the first balloon portion 282 and the second balloon portion 284 of the radially translatable member 280 radially and as a result the connection portion 286 is pulled linearly.

Responsive to an output of the linear displacement sensor, which senses the amount of linear translation experienced by the connection portion 286, i.e. how much the connection portion 286 was linearly translated, the control unit 111$^b$ can determine how much the balloon 105 expanded. Particularly, the amount of linear translation of the connection portion exhibits a predetermined relationship with the amount of radial translation of the respective balloon portion/s, thereby the control unit 111$^b$ can determine the distance that the balloon 105 has radially expanded. Utilizing the determined amount of radial expansion, the control unit 111$^b$ can then determine how much the frame 120$^b$ has expanded. The control unit 111$^b$ can further determine the radial diameter of the frame 120$^b$.

The control unit 111$^b$ can then compare the determined information to predetermined parameters, such as the maximum expansion allowed and/or the maximum radial diameter allowed. As described above, the information can be determined responsive to a linear displacement sensor and/or at least one flex sensor. Responsive to an outcome of the comparison, the control unit 111$^b$ can then control the pump 230 to adjust the flow of the inflation fluid 212. According to some embodiments, the control unit 111$^b$ can control the pump 230 to stop the flow of the inflation fluid 212 into the balloon 105 when the determined expansion amount and/or the determined radial diameter has reached the respective maximum value. Furthermore, the control unit 111$^b$ can control the pump 230 to slow the flow rate of the inflation fluid 212 as the determined expansion amount and/or the determined radial diameter approaches the respective maximum value.

Figure 21:
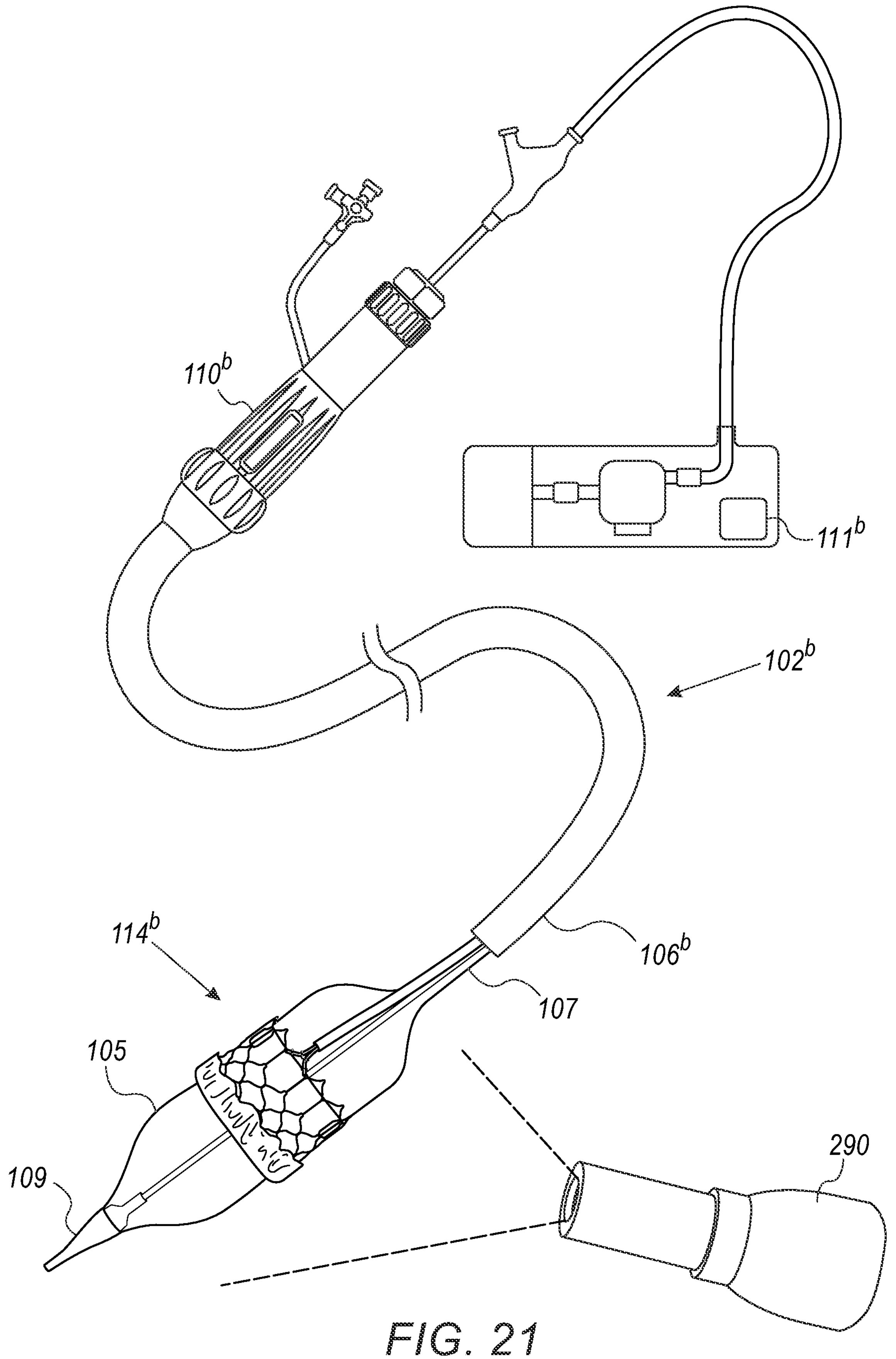
FIG. 21 shows the delivery assembly of FIG. 16, further comprising an imager, according to some embodiments.

FIG. 21 shows an example of an imager 290 as part of delivery assembly 100$^b$. Imager 290 can be in communication with the control unit 111$^b$. According to some embodiments, the imager 290 can comprise an x-ray imager. The x-ray imager can comprise a static imager and/or a fluoroscopy imager. According to some embodiments, imager 290 can image any relevant portion of valve 114$^b$. Responsive to the acquired images, control unit 111$^b$ can determine: the amount that the frame 120$^b$ and/or the balloon 105 has expanded; and/or the radial diameter of the frame 120$^b$ and/or the balloon 105. As described above, the radial diameter of the balloon 105 and the expansion amount of the balloon 105 are each indicative of the radial diameter of the frame 120$^b$.

According to some embodiments, the imager 290 can directly image the frame 120$^b$, which is typically composed of a material that exhibits a high radiation absorption coefficient. The images can be analyzed by control unit 111$^b$ and/or an additional computer to determine the expansion amount and/or the radial diameter of the frame 120$^b$. Alternatively, or additionally, a plurality of radiopaque markers 292 are deposited on predetermined locations of the frame 120$^b$ and/or the balloon 105. For example, a frame can be made of a non-metallic (e.g., polymeric) material which is not necessarily radiopaque, in which case radiopaque markers 292 may be added thereto.

Figure 22A:
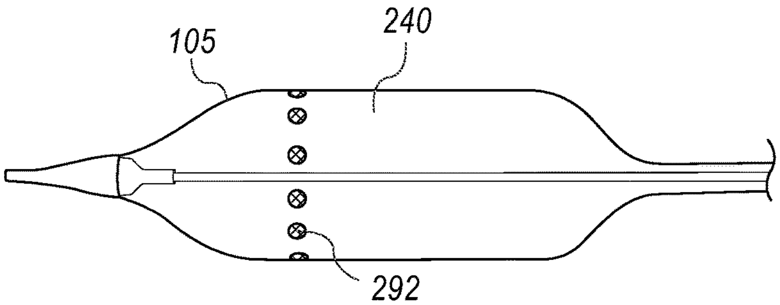
FIG. 22A shows radiopaque markers positioned on an inflatable balloon, according to some embodiments.
Figure 22B:
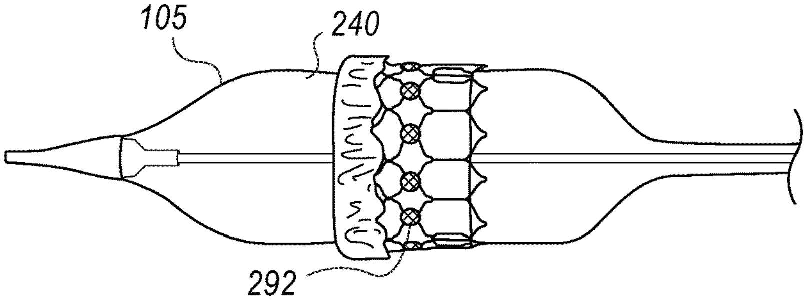
FIG. 22B shows radiopaque markers positioned on the frame of a prosthetic valve, according to some embodiments.

As shown in FIGS. 22A and 22B, the radiopaque markers 292 can be deposited with predetermined spacings therebetween. According to some embodiments, the radiopaque markers 292 can be deposited on the outer surface 240 of the balloon 105 and/or within the interior of the balloon 105. In embodiments where the radiopaque markers 292 are deposited on the frame 120$^b$, the radiopaque markers 292 can be secured to predetermined struts 121$^b$. Alternatively, or additionally, one or more radiopaque bands can be positioned to surround the frame 120$^b$ and/or the balloon 105. Alternatively, or additionally, one or more predetermined locations of the frame 120$^b$ and/or the balloon 105 can be coated with a radiopaque coating.

The images received from imager 290 can then be analyzed to identify the radiopaque markers 292, band/s and/or coatings, and to determine therefrom the expansion amount and/or the radial diameter of the frame 120$^b$ and/or the balloon 105. According to some embodiments, the expansion amount of the frame 120$^b$ and/or the balloon 105 can be determined by identifying changes in the distances between adjacent radiopaque markers 292. Particularly, as the balloon 105 and/or the frame 120$^b$ expands, the distance between adjacent radiopaque markers 292 increases.

Figure 23:
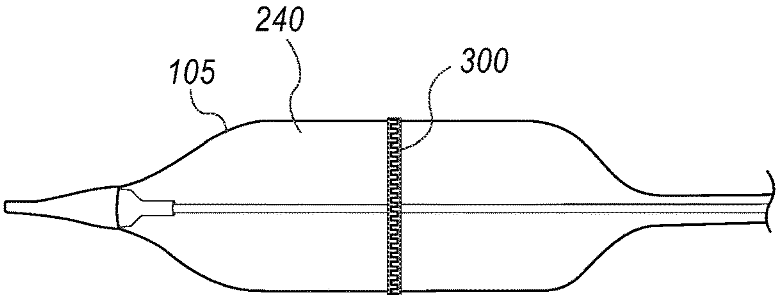
FIG. 23 shows a side view of an inflatable balloon with a strain gauge, according to certain embodiments.

FIG. 23 shows the balloon 105 in an inflated state, with a strain gauge 300 juxtaposed with the outer surface 240 of the balloon 105. According to some embodiments, the strain gauge 300 can be elongated, and can further be disposed circumferentially on the balloon 105. According to some embodiments, the length of the elongated strain gauge 300 can be shorter than the circumference of the outer surface 240. The strain gauge 300 can be in communication with the control unit 111$^b$ (not shown). The communication can be accomplished via a retractable communication channel (not shown), as described above in relation to communication channel 160. According to some embodiments, the operation of the strain gauge 300 can be performed in cooperation with the control unit 111$^b$. The strain gauge 300 can be an electronic strain gauge, i.e. electrical properties thereof change responsive to the strain applied thereto. Alternatively, or additionally, the strain gauge 300 can be an optical strain gauge, i.e. optical properties thereof change responsive to the strain applied thereto.

It is to be noted that strain gauge 300 is shown in FIG. 25 to circumscribe the balloon 150 by way of illustration and not limitation, and that the length of the strain gauge 300 in the circumferential direction can be any suitable length, which can be significantly shorter than the perimeter of the balloon 105, yet long enough to provide a significant indication of the increase in diameter of the balloon during inflation (or deflation) thereof, when juxtaposed over the balloon's external surface in the circumferential direction. According to some embodiments, the strain gauge 300 is glued or sutured to the outer surface of the balloon 105.

As the balloon 105 is inflated, the output of the strain gauge 300 changes responsive to the strain applied thereto, i.e. responsive to the strain applied to the balloon 105. The output of the strain gauge 300 thus provides an indication of the diameter of the balloon 105. As described above, the diameter of the balloon 105 provides an indication of the diameter of the frame 120$^b$. Additionally, the control unit 111$^b$ can track the changes in the output of the strain gauge 300 to determine the amount of inflation/expansion of the balloon 105 and/or the frame 120$^b$. Although the above has been described in relation to an embodiment where the strain gauge 300 is juxtaposed with the balloon 105, this is not meant to be limiting in any way. According to some embodiments (not shown), the strain gauge 300 can be disposed on the frame 120$^b$ and thus the diameter of the frame 120$^b$ can be measured directly.

Although the above has been described in relation to an illustrated embodiment where a single strain gauge 300 is provided, this is not meant to be limiting in any way, and a plurality of strain gauges 300 can be provided. In such an embodiment, each strain gauge 300 is circumferentially disposed on the balloon 105 over a respective circumferential cross-section.

As described above, responsive to the determined expansion amount and/or radial diameter of the balloon 105 and/or the frame 120$^b$, the control unit 111$^b$ can control the pump 230 to adjust the flow of the inflation fluid 212 into, and/or out of, the balloon 105. Advantageously, the pump 230 allows the balloon 105 to be controllably expanded, thereby providing more accurate deployment of the balloon expandable valve 114$^b$. The additional linear displacement sensor 260 and/or the imager 290, in combination with the control unit 111$^b$, provide further accuracy to the deployment of the balloon expandable valve 114$^b$.

As described above, the control unit 111$^b$, in cooperation with the pressure sensor 238, can monitor the pressure of the inflation fluid 212, which exhibits a direct relationship to the radial forces on the surrounding tissue, and control the pump 230 to maintain the pressure within a desired predetermined range. According to some embodiments, the control unit 111$^b$ can determined both the pressure and the radial diameter of the balloon 105 and/or the frame 120$^b$. For example, the control unit 111$^b$ can compare changes in the pressure to changes in the diameter. If the pressure rises without a similar increase in diameter, it can be an indication that pressure against the tissue is increasing while the balloon 105 has reached its maximum (or near maximum) expandible parameters, and should not be expanded further as any further. Similarly, if the diameter increases without an increase in pressure, it can be an indication that the balloon 105 has not yet reached its maximum expandible parameters and should thus may be safely expanded further. According to some embodiments, the control unit 111$^b$ compares a predetermined function of the difference between the increase in pressure and the increase in diameter to a predetermined threshold. The predetermined function can be a derivative of a curve plotted from: the increase values of the pressure and diameter; and/or the absolute values thereof. Responsive to an outcome of the comparison, the control unit 111$^b$ can control the pump 230 to adjust the flow of the inflation fluid 212, e.g. to cease the flow of the inflation fluid 212 into the balloon 105.

It is known from material science that stress-strain curves describe the relationship between stress and strain, and are typically obtained by gradually applying a load (i.e., force) to a material and measuring the deformation caused thereto as a result of the applied load. Certain materials exhibit a behavior, in which the strain initially increases in a proportional ratio to the increase in the stress applied to the material (the linear elastic region). After a certain critical point (i.e., yield strength), the stress increase can cause the material to undergo plastic deformation and/or to suffer failure (e.g., fracture).

Is it contemplated that arterial and annular tissues (e.g., at a native heart valve) can exhibit certain similar behaviors, as described in stress-strain curves. For example, upon the initial application of a radial expanding force (i.e., stress) to the tissue, and more specifically to the annulus, the annular diameter can increase in a proportional ratio to the increase in the radial force applied thereto (an elastic region). After reaching a certain critical diameter, the tissue is expanded or stretched beyond its physiological limit, and therefore increasing the application of radial forces thereto can cause the tissue to sustain irreversible plastic deformation and/or suffer critical damage (e.g., rupture).

According to some embodiments, the present invention is able to produce measurements which are indicative of both the prosthetic valve's or balloon's expansion diameter and the radial forces exerted thereby on the surrounding tissue, within the desired implantation site, such as the site of malfunctioning native valve within the heart. By simultaneously measuring the valve's or balloon's expansion diameter and the forces exerted thereby on the surrounding tissue, it is possible to identify the critical expansion diameter, in which a diameter larger than the critical diameter will exert increasing radial forces thereto, which can result in critical damage to the surrounding tissue. Advantageously, the present invention enables to identify the critical diameter, thus enabling to expand the valve to a diameter optionally equal to or smaller than the critical diameter, in order to prevent possible tissue damage.

Although the above has been described in relation to a balloon configured to expand a prosthetic valve, this is not meant to be limiting in any way. According to some embodiments, the above systems can be utilized with an inflatable balloon arranged to expand any suitable type of stent. According to some embodiments, the above systems can be utilized with an inflatable balloon configured to be used without an expandable valve, or other stent, such as during valvuloplasty procedures, pre-ballooning procedures and post-ballooning procedures. In such embodiments, the control unit 111$^b$ can be configured to control the operation of the pump 230 responsive to the expanded radial diameter of the balloon 105 and/or the pressure of the inflation fluid 212.

Figure 24A:
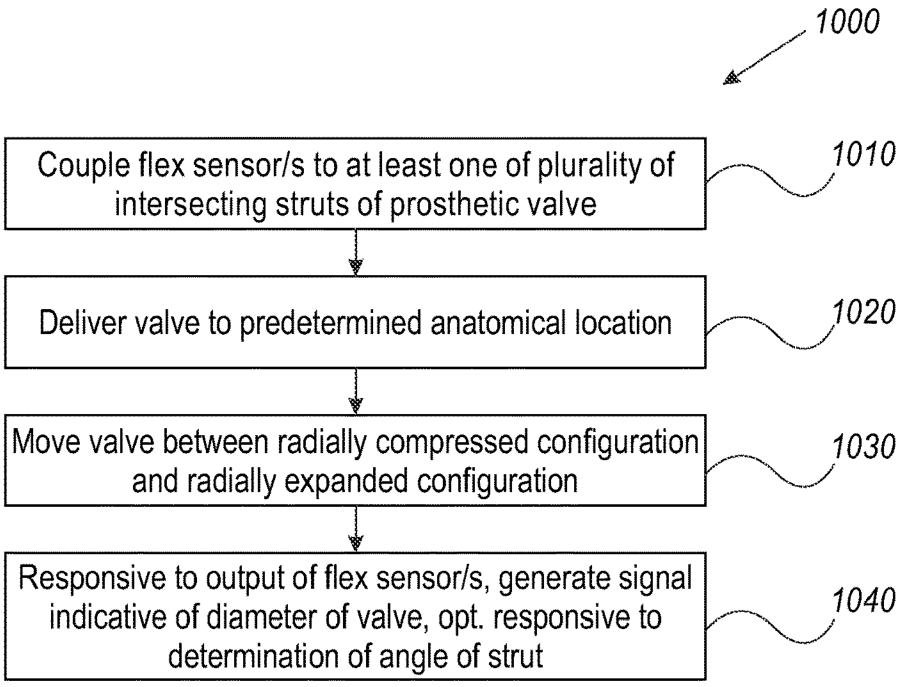
FIGS. 24A-24C show high level flow charts of various deployment methods for a prosthetic valve, utilizing at least one flex sensor, according to some embodiments.

FIG. 24A shows a high level flow chart of a delivery method 1000 for a prosthetic valve, in accordance with some embodiments. The delivery method 1000 can include a step 1010, where at least one flex sensor is coupled to at least one of a plurality of intersecting struts of a prosthetic valve. According to some embodiments, the at least one flex sensor comprises at least a pair of flex sensors, each of the pair of flex sensors coupled to a respective one of a pair of the plurality of struts. The pair of the plurality of struts can intersect each other.

The delivery method 1000 can further include a step 1020, where the prosthetic valve of step 1010 is delivered to a predetermined anatomical location. According to some embodiments, the prosthetic valve is delivered through the aorta to a target implantation site, such as a defective heart valve (e.g., the native aortic valve). The delivery method 1000 can further include a step 1030, where the delivered valve of step 1020 is moved between a radially compressed configuration and a radially expanded configuration. In the radially compressed configuration, the delivered valve can be crimped to have a minimal radial diameter. The radially expanded configuration can include a range of radial diameters of the delivered valve. Movement between the radially compressed configuration and the radially expanded configuration can be performed by linear forces applied to the struts of the valve and/or by inflating a balloon positioned within a frame of the delivered valve.

The delivery method 1000 can further include a step 1040. In step 1040, responsive to an output of the at least one flex sensor of step 1010, a signal indicative of the radial diameter of the valve is generated. According to some embodiments, an opening angle of one or more struts is measured responsive to the output of the at least one flex sensor, and the radial diameter of the valve is determined responsive to the measured opening angle.

Figure 24B:
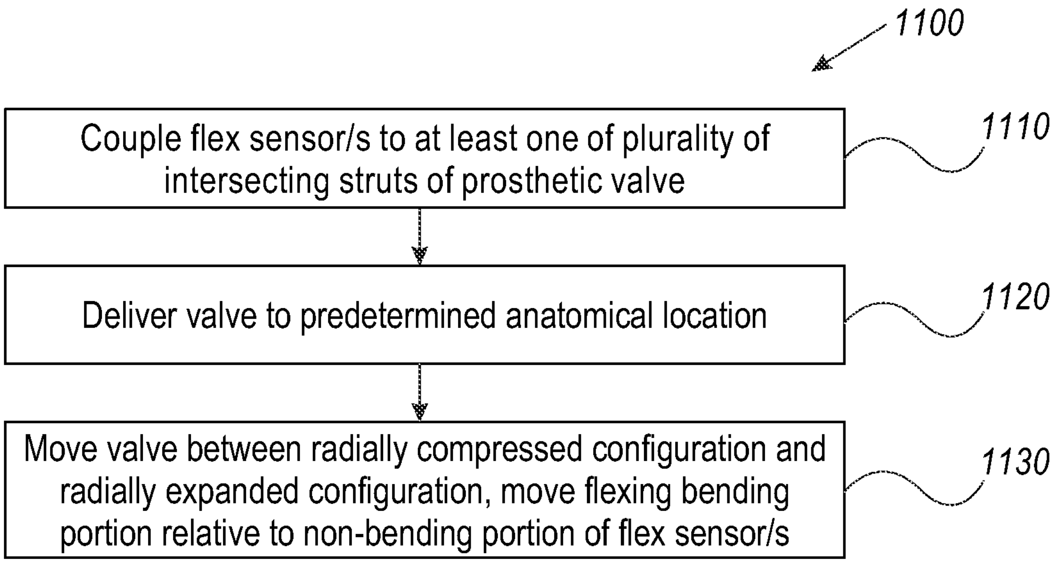

FIG. 24B shows a high level flow chart of a delivery method 1100 for a prosthetic valve, in accordance with some embodiments. The delivery method 1100 can include a step 1110, where at least one flex sensor is coupled to at least one of a plurality of intersecting struts of a prosthetic valve. According to some embodiments, the at least one flex sensor comprises at least a pair of flex sensors, each of the pair of flex sensors coupled to a respective one of a pair of the plurality of struts. The pair of the plurality of struts can intersect each other.

The delivery method 1100 can further include a step 1120, where the prosthetic valve of step 1110 is delivered to a predetermined anatomical location. According to some embodiments, the prosthetic valve is delivered in a transfemoral approach, through the aorta to a target implantation site, such as a defective heart valve. The delivery method 1100 can further include a step 1130, where the delivered valve of step 1020 is moved between a radially compressed configuration and a radially expanded configuration. In the radially compressed configuration, the delivered valve can be crimped to have a minimal radial diameter. The radially expanded configuration can include a range of radial diameters of the delivered valve.

Movement between the radially compressed configuration and the radially expanded configuration can be performed by linear forces applied to the struts of the valve and/or by inflating a balloon positioned within a frame of the delivered valve. The radial expansion of the valve during the movement to the radially expanded configuration flexes a bending portion of the at least one flex sensor relative to a non-bending portion of the at least one flex sensor. Particularly, according to some embodiments, each of the at least one flex sensor is coupled to the valve such that a first portion of the respective flex sensor bends as the respective strut opens outwards during the expansion and a second portion of the respective flex sensor does not bend when the respective strut opens.

According to some embodiments, responsive to an output of the at least one flex sensor, a signal indicative of the radial diameter of the valve is generated. According to some embodiments, an opening angle of one or more struts is measured responsive to the output of the at least one flex sensor, and the radial diameter of the valve is determined responsive to the measured opening angle. The opening angle can be determined responsive to the determined angle between the bending portion and the non-bending portion of the at least one flex sensor.

Figure 24C:
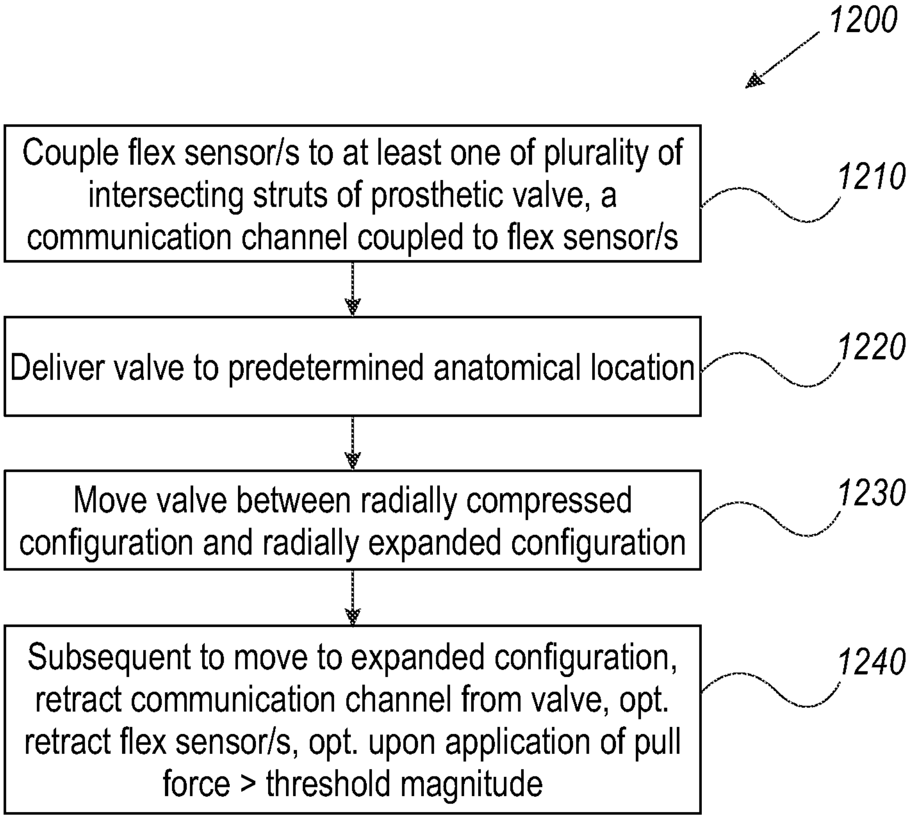

FIG. 24C shows a high level flow chart of a delivery method 1200 for a prosthetic valve, in accordance with some embodiments. The delivery method 1200 can include a step 1210, where at least one flex sensor is coupled to at least one of a plurality of intersecting struts of a prosthetic valve. According to some embodiments, the at least one flex sensor comprises at least a pair of flex sensors, each of the pair of flex sensors coupled to a respective one of a pair of the plurality of struts. The pair of the plurality of struts can intersect each other.

According to some embodiments, at least one communication channel can be coupled to the at least one flex sensor. The at least one communication channel can be coupled to an output of the at least one flex sensor. For example, a flex sensor can comprise an output composed of a pair of electrical leads, the communication channel being coupled to the pair of electrical leads. The at least one communication channel can provide electrical and/or optical communication between an output of the at least one flex sensor and a control unit. According to some embodiments, the at least one communication channel can be detachably coupled to the at least one flex sensor. According to some embodiments, a plurality of flex sensors and a plurality of communication channels can be provided, each of the plurality of communication channels coupled to a respective one of the plurality of flex sensors.

The delivery method 1200 can further include a step 1220, where the prosthetic valve of step 1210 is delivered to a predetermined anatomical location. According to some embodiments, the prosthetic valve is delivered through the aorta to a defective heart valve. The delivery method 1200 can further include a step 1230, where the delivered valve of step 1220 is moved between a radially compressed configuration and a radially expanded configuration. In the radially compressed configuration, the delivered valve can be crimped to have a minimal radial diameter. The radially expanded configuration can include a range of radial diameters of the delivered valve. Movement between the radially compressed configuration and the radially expanded configuration can be performed by linear forces applied to the struts of the valve and/or by inflating a balloon positioned within a frame of the delivered valve.

The delivery method 1200 can further include a step 1240. In step 1240, subsequent to the valve moving to an expanded configuration of step 1220, the at least one communication channel of step 1210 can be retracted from the valve. According to some embodiments, the at least one communication channel can be detached from the at least one flex sensor and retracted from the valve. According to some embodiments, the at least one flex sensor can be retracted from the valve, with the at least one communication channel still coupled thereto. According to some embodiments, the at least one communication channel can be detachable from the at least one flex sensor upon application of a pull force on the at least one communication channel responsive to the magnitude of the pull force being higher than a predetermined threshold magnitude.

According to some embodiments, responsive to an output of the at least one flex sensor, a signal indicative of the radial diameter of the valve is generated. According to some embodiments, an opening angle of one or more struts is measured responsive to the output of the at least one flex sensor, and the radial diameter of the valve is determined responsive to the measured opening angle. The opening angle can be determined responsive to the determined angle between the bending portion and the non-bending portion of the at least one flex sensor.

Figure 25A:
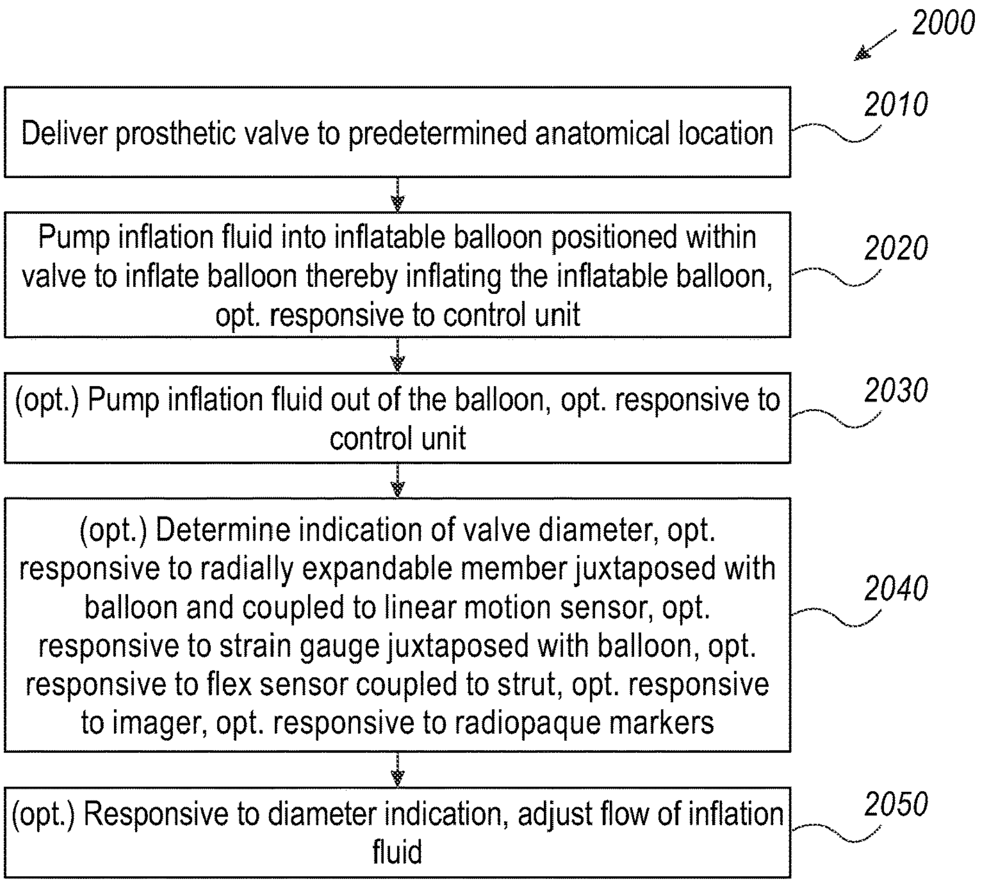
FIGS. 25A-25B show high level flow charts of various deployment methods for a prosthetic valve, utilizing a pump-inflatable balloon, according to some embodiments.

FIG. 25A shows a high level flow chart of a delivery method 2000, in accordance with some embodiments. The delivery method 2000 can include a step 2010, where an inflatable balloon, positioned within a prosthetic valve is delivered to a predetermined anatomical location. The prosthetic valve can be delivered through the aorta to a target implantation site, such as a defective heart valve.

According to some embodiments, the delivery method 2000 can include a step 2020. In step 2020, inflation fluid can be pumped by a pump into the inflatable balloon of step 2010, thereby inflating the inflatable balloon. The inflation of the inflatable balloon expands the expandable prosthetic valve. According to some embodiments, the pump can be controlled by a control unit.

According to some embodiments, the delivery method 2000 can further include a step 2030. In step 2030, the pump can be controlled to pump at least a portion of the inflation fluid out of the inflatable balloon. Pumping the inflation fluid out of the inflatable balloon can be responsive to the control unit of step 2020. According to some embodiments, pumping the inflation fluid of the inflatable balloon is performed after expansion of the expandable prosthetic valve.

According to some embodiments, the delivery method 2000 can further include a step 2040. In step 2040, an indication of the radial diameter of the prosthetic valve can be determined. The indication of the diameter of the prosthetic valve can be determined responsive to a determination of the radial diameter of the inflatable balloon. According to some embodiments, the diameter indication can be determined responsive to at least one radially expandable member juxtaposed with an outer surface of the inflatable balloon and coupled to a linear motion sensor, such that the linear motion sensor measures the amount of radial expansion of the radially expandable member. According to some embodiments, the diameter indication can be determined responsive to at least one strain gauge juxtaposed with an outer surface of the inflatable balloon. According to some embodiments, the diameter indication can be determined responsive to at least one flex sensor coupled to at least one of a plurality of interconnecting struts of the prosthetic valve. According to some embodiments, the diameter indication can be determined responsive to images of an imager that images the prosthetic valve and/or the inflatable balloon. The imager can image radiopaque markers positioned on a frame of the prosthetic valve and/or the inflatable balloon. According to some embodiments, pumping the inflation fluid out of the inflatable balloon can be responsive to the determination of the radial diameter of the inflatable balloon and/or the prosthetic valve.

According to some embodiments, the indication of the diameter of the prosthetic valve can comprise an indication of the diameter of the inflatable balloon. For example, the indication of the diameter of the prosthetic valve can be the measured diameter of the inflatable balloon. Alternatively, the indication of the diameter of the prosthetic valve can be another indication of the radial diameter of the inflatable balloon. For example, the indication of the radial diameter of the inflatable balloon can comprise the difference between an initial radial diameter of the inflatable balloon and the inflated radial diameter of the inflatable balloon. Therefore, the indication of the radial diameter of the inflatable balloon can comprise a change in the radial diameter of the inflatable balloon over a plurality of measurements. Similarly, the indication of the radial diameter of the prosthetic valve can comprise a change in the radial diameter of the prosthetic valve and/or the inflatable balloon over a plurality of measurements.

According to some embodiments, the delivery method 2000 can further include a step 2050. In step 2050, responsive to the determined radial diameter indication of step 2040, the flow of the inflation fluid of step 2020 into, and/or out of, the inflatable balloon is adjusted. The determined radial diameter indication can be compared to one or more predetermined radial diameter threshold values, and the flow of the inflation fluid can be adjusted responsive to an outcome of the comparison.

Figure 25B:
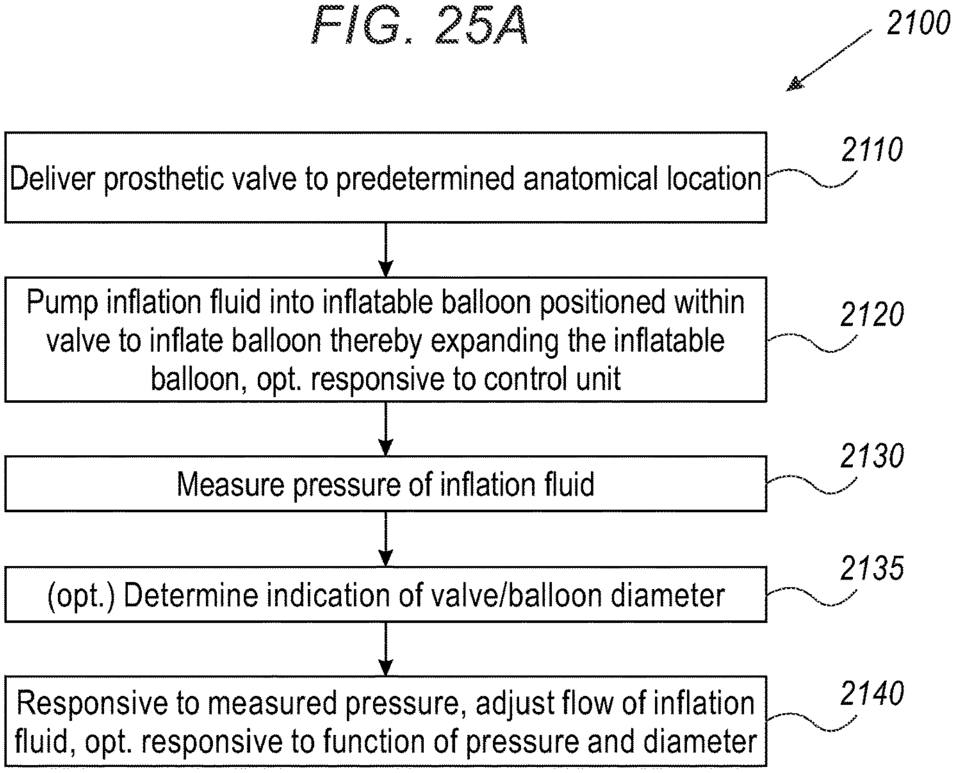

FIG. 25B shows a high level flow chart of a delivery method 2100, in accordance with some embodiments. The delivery method 2100 can include a step 2110, where an inflatable balloon, positioned within a prosthetic valve is delivered to a predetermined anatomical location. According to some embodiments, the prosthetic valve is delivered through the aorta to a defective heart valve.

According to some embodiments, the delivery method 2100 can further include a step 2120. In step 2120, inflation fluid can be pumped by a pump into the inflatable balloon of step 2110, thereby inflating the inflatable balloon. The inflation of the inflatable balloon expands the expandable prosthetic valve. According to some embodiments, the pump can be controlled by a control unit.

According to some embodiments, the delivery method 2200 can further include a step 2130. In step 2130, the pressure of the inflation fluid of step 2120 flowing into the inflatable balloon can be measured. The pressure can be measured by a pressure sensor positioned within the inflation fluid flow. The pressure sensor can be positioned between the pump and the inflatable balloon, and/or within the inflatable balloon.

According to some embodiments, the delivery method 2200 can further include a step 2135. In step 2135, an indication of the radial diameter of the prosthetic valve, and/or the inflatable balloon, can be determined, as described above in relation to step 2040 of method 2000.

According to some embodiments, the delivery method 2100 can further include a step 2140. In step 2140, responsive to the measured pressure of step 2130, the flow of the inflation fluid of step 2120 can be adjusted. According to some embodiments, the measured pressure of step 2130 can be compared with one or more predetermined pressure threshold values and the flow of the inflation fluid can be adjusted responsive to an outcome of the comparison.

According to some embodiments, a predetermined function of the increase in pressure and the increase in diameter can be determined, and the flow of the inflation fluid can be adjusted responsive to the predetermined function. The predetermined function can be compared to a predetermined threshold, and the flow of the inflation fluid can be adjusted responsive to an outcome of the comparison. According to some embodiments, the predetermined function can be a derivative of a curve plotted from: the increase values of the pressure and diameter; and/or the absolute values thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although the invention is described in conjunction with specific embodiments thereof, it is evident that numerous alternatives, modifications and variations that are apparent to those skilled in the art may exist. It is to be understood that the invention is not necessarily limited in its application to the details of construction and the arrangement of the components and/or methods set forth herein. Other embodiments may be practiced, and an embodiment may be carried out in various ways. Accordingly, the invention embraces all such alternatives, modifications and variations that fall within the scope of the appended claims.

The invention claimed is:

1. A delivery assembly, comprising:

a prosthetic valve movable between a radially compressed configuration and a radially expanded configuration, the prosthetic valve comprising a plurality of intersecting struts and at least one coupling member;

a delivery apparatus comprising:

a handle;

a sensor shaft extending distally from the handle;

at least one flex sensor configured to be removably coupled to at least one of the plurality of struts;

a control unit in communication with the at least one flex sensor and configured to generate a signal indicative of a diameter of the prosthetic valve based at least in part on an output of the at least one flex sensor;

at least one communication channel configured to detachably couple with the at least one flex sensor and allow communication between the at least one flex sensor and the control unit;

wherein the at least one coupling member is coupled to a first strut of the plurality of intersecting struts; and wherein the at least one flex sensor is configured to be coupled to the at least one coupling member and slide within the at least one coupling member relative to the first strut during valve expansion or compression.

2. The delivery assembly of claim 1, wherein the delivery apparatus further comprises:

a control unit in communication with the at least one flex sensor; and at least one communication channel detachably coupled to the at least one flex sensor and configured to allow communication between the at least one flex sensor and the control unit, wherein the control unit is configured to generate a signal indicative of a diameter of the prosthetic valve based at least in part on an output of the at least one flex sensor.

3. The delivery assembly of claim 2, wherein the at least one communication channel is axially movable within the sensor shaft.

4. The delivery assembly of claim 1, wherein the at least one flex sensor comprises a non-bending portion and a bending portion configured to flex relative to the non-bending portion.

5. The delivery assembly of claim 4, wherein the bending portion of the at least one flex sensor is configured to bend about a distal end of the sensor shaft.

6. The delivery assembly of claim 4, wherein the non-bending portion of the at least one flex sensor is coupled to at least one actuator assembly of the prosthetic valve.

7. The delivery assembly of claim 1, wherein the prosthetic valve further comprises at least one actuator assembly, wherein the delivery apparatus further comprises an actuation member releasably coupled to the at least one actuator assembly, and wherein the actuation member is configured to move the prosthetic valve between the radially compressed state and the radially expanded state.

8. The delivery assembly of claim 1, wherein the at least one coupling member comprises at least one of: a suture, a band, a tube, or a sleeve.

9. The delivery assembly of claim 1, wherein the at least one flex sensor is slidable relative to the at least one coupling member upon application of a force exceeding the frictional force applied by the at least one coupling member on the at least one flex sensor.

10. The delivery assembly of claim 1, further comprising:

an inflatable balloon positioned within the prosthetic valve;

a reservoir containing a predetermined volume of inflation fluid;

a pump in fluid communication with the reservoir; and a fluid flow channel, a distal end of the fluid flow channel in fluid communication with an opening of the inflatable balloon and a proximal end of the fluid flow channel in fluid communication with the pump, wherein inflation of the inflatable balloon is configured to cause movement of the prosthetic valve between the radially compressed configuration and the radially expanded configuration; and wherein the pump is configured to generate flow of the inflation fluid into the inflatable balloon via the fluid flow channel.

11. The delivery assembly of claim 10, wherein the flow of the inflation fluid is based at least in part the signal indicative of the diameter of the prosthetic valve.

12. The delivery assembly of claim 11, wherein the at least one communication channel extends through the detachable shaft and is axially movable within the detachable shaft.

13. The delivery assembly of claim 11, wherein the at least one communication channel is detachable from the at least one flex sensor upon application of a pull force on the at least one communication channel greater than a predetermined threshold.

14. The delivery assembly of claim 11, wherein the sensor housing comprises a proximal threaded end, wherein the detachable shaft comprises a distal threaded end, wherein the distal threaded end of the detachable shaft is configured to engage with the proximal threaded end of the sensor housing.

15. The delivery assembly of claim 11, wherein the at least one flex sensor is an optic flex sensor configured to generate an optic signal, wherein the at least one communication channel is an optic conductor.

16. The delivery assembly of claim 11, further comprising:

an inflatable balloon positioned within the prosthetic valve;

a reservoir containing a predetermined volume of inflation fluid;

a pump in fluid communication with the reservoir; and a fluid flow channel, a distal end of the fluid flow channel in fluid communication with an opening of the inflatable balloon and a proximal end of the fluid flow channel in fluid communication with the pump, wherein inflation of the inflatable balloon is configured to cause movement of the prosthetic valve between the radially compressed configuration and the radially expanded configuration; and wherein the pump is configured to generate flow of the inflation fluid into the inflatable balloon via the fluid flow channel.

17. The delivery assembly of claim 16, wherein the delivery apparatus comprises a control unit configured to generate a signal indicative of a diameter of the prosthetic valve based at least in part on an output of the at least one flex sensor, and wherein the flow of the inflation fluid is based at least in part the signal indicative of the diameter of the prosthetic valve.

18. A delivery assembly, comprising:

a prosthetic valve movable between a radially compressed configuration and a radially expanded configuration, the prosthetic valve comprising:

a plurality of intersecting struts;

a sensor housing coupled to at least one of the plurality of struts; and at least one flex sensor coupled to the sensor housing, the at least one flex sensor configured to flex during valve expansion or compression; and a delivery apparatus comprising:

a handle;

a detachable shaft extending distally from the handle; and at least one communication channel configured to detachably couple with the at least one flex sensor and allow communication between the at least one flex sensor and a control unit, wherein the detachable shaft is configured to detachably couple to the sensor housing and isolate the at least one communication channel from ambient flow.

19. A method of delivering a prosthetic valve, the method comprising:

providing a prosthetic valve comprising a plurality of intersecting struts and at least one flex sensor couple to at least one of the plurality of intersecting struts;

providing a delivery apparatus comprising a handle, an actuator, and at least one communication channel;

coupling the at least one communication channel with the at least one flex sensor;

coupling the actuator to an actuation assembly of the prosthetic valve;

delivering the prosthetic valve to a predetermined anatomical location;

actuating, via the actuator, the actuation assembly of the prosthetic valve to cause the prosthetic valve to move between a radially compressed configuration and a radially expanded configuration;

determining an estimated diameter of the prosthetic valve based at least in part on a signal generated by the at least one flex sensor, wherein the signal is indicative of an amount of bend experienced by the at least one flex sensor;

detaching the at least one communication channel from the at least one flex sensor;

detaching the actuator from the actuation assembly of the prosthetic valve.

20. The method of claim 19, wherein the detaching the at least one communication channel from the at least one flex sensor comprises:

detaching a detachable shaft of the delivery apparatus from a sensor housing of the at least one sensor flex sensor, wherein the at least one communication channel extends axially within the detachable shaft, and wherein the at least one sensor flex sensor is housed within the sensor housing.

* * * * *